US009717539B2

(12) United States Patent
Donner et al.

(10) Patent No.: US 9,717,539 B2
(45) Date of Patent: Aug. 1, 2017

(54) IMPLANTS, SYSTEMS, AND METHODS FOR FUSING A SACROILIAC JOINT

(71) Applicant: JCBD, LLC, Fort Collins, CO (US)

(72) Inventors: Edward Jeffrey Donner, Fort Collins, CO (US); Christopher Thomas Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 0 days.

(21) Appl. No.: 14/567,956

(22) Filed: Dec. 11, 2014

(65) Prior Publication Data

US 2015/0094765 A1 Apr. 2, 2015

Related U.S. Application Data

(63) Continuation-in-part of application No. 14/514,221, filed on Oct. 14, 2014, and a continuation-in-part of application No. 14/447,612, filed on Jul. 31, 2014.
(Continued)

(51) Int. Cl.
*A61B 17/70* (2006.01)
*A61B 17/17* (2006.01)
(Continued)

(52) U.S. Cl.
CPC ...... *A61B 17/7055* (2013.01); *A61B 17/1735* (2013.01); *A61B 17/1739* (2013.01);
(Continued)

(58) Field of Classification Search
CPC .......... A61B 17/705–17/7055; A61B 17/1796; A61F 2002/30995
See application file for complete search history.

(56) References Cited

U.S. PATENT DOCUMENTS 4,488,542 A 12/1984 Helland
4,569,338 A 2/1986 Edwards
(Continued)

FOREIGN PATENT DOCUMENTS

AU 1753200 8/2000
CN 2265765 10/1997
(Continued)

OTHER PUBLICATIONS

Baria, Dinah, "Sacroiliac Joint Biomechanics and Effects of Fusion" (2010). Open Access Dissertations. Paper 466. http://scholarlyrepository.miami.edu/oa_dissertations, 179 pages.
(Continued)

*Primary Examiner* — Eduardo C Robert
*Assistant Examiner* — Steven Cotroneo
(74) *Attorney, Agent, or Firm* — Polsinelli PC; Joshua J. Pranckun; Samuel Wade Johnson

(57) ABSTRACT

A sacroiliac joint fusion system including a joint implant, an anchor element and a delivery tool including an implant arm, an anchor arm, and a positioning arm coupling the implant arm and the anchor arm. The implant arm includes an implant shaft extending between a proximal end and a distal end of the implant arm. The anchor arm including an anchor shaft extending between a proximal end and a distal end of the anchor arm. The positioning arm coupled with the implant arm at a first end and coupled with the anchor arm at a second end.

25 Claims, 62 Drawing Sheets

Related U.S. Application Data

(60) Provisional application No. 61/914,409, filed on Dec. 11, 2013, provisional application No. 61/891,330, filed on Oct. 15, 2013, provisional application No. 61/891,345, filed on Oct. 15, 2013, provisional application No. 61/912,494, filed on Dec. 5, 2013, provisional application No. 61/914,409, filed on Dec. 11, 2013, provisional application No. 61/954,594, filed on Mar. 17, 2014, provisional application No. 61/979,857, filed on Apr. 15, 2014, provisional application No. 61/955,126, filed on Mar. 18, 2014, provisional application No. 61/914,409, filed on Dec. 11, 2013, provisional application No. 61/860,185, filed on Jul. 30, 2013.

(51) Int. Cl.
 *A61F 2/30* (2006.01)
 *A61B 90/00* (2016.01)

(52) U.S. Cl.
 CPC .. *A61B 17/7074* (2013.01); *A61B 2090/3966* (2016.02); *A61F 2002/30995* (2013.01)

(56) References Cited

U.S. PATENT DOCUMENTS

| | | |
|---|---|---|
| 4,590,928 A | 5/1986 | Hunt et al. |
| 4,622,959 A | 11/1986 | Marcus |
| 4,714,469 A | 12/1987 | Kenna |
| 4,773,402 A | 9/1988 | Asher et al. |
| 4,794,918 A | 1/1989 | Wolter |
| 4,863,476 A | 9/1989 | Shepperd |
| 4,881,535 A | 11/1989 | Sohngen |
| 4,911,153 A | 3/1990 | Border |
| 4,920,958 A | 5/1990 | Walt et al. |
| 4,950,270 A | 8/1990 | Bowman et al. |
| 5,026,373 A | 6/1991 | Ray et al. |
| 5,052,375 A | 10/1991 | Stark et al. |
| 5,108,397 A | 4/1992 | White |
| 5,112,337 A | 5/1992 | Paulos et al. |
| 5,176,681 A | 1/1993 | Lawes et al. |
| 5,192,327 A | 3/1993 | Brantigan |
| 5,242,444 A | 9/1993 | MacMillan |
| 5,282,861 A | 2/1994 | Kaplan |
| 5,334,192 A | 8/1994 | Behrens |
| 5,334,205 A | 8/1994 | Cain |
| 5,336,225 A | 8/1994 | Zang |
| 5,368,546 A | 11/1994 | Stark et al. |
| 5,368,593 A | 11/1994 | Stark |
| 5,437,674 A | 8/1995 | Worcel et al. |
| 5,443,509 A | 8/1995 | Boucher et al. |
| 5,456,267 A | 10/1995 | Stark |
| 5,480,402 A | 1/1996 | Kim |
| 5,484,389 A | 1/1996 | Stark et al. |
| 5,591,235 A | 1/1997 | Kuslich |
| 5,593,407 A | 1/1997 | Reis |
| 5,607,424 A | 3/1997 | Tropiano |
| 5,609,635 A | 3/1997 | Michelson |
| 5,609,636 A | 3/1997 | Kohrs et al. |
| 5,626,434 A | 5/1997 | Cook |
| 5,658,337 A | 8/1997 | Kohrs et al. |
| 5,669,909 A | 9/1997 | Zdeblick et al. |
| 5,688,284 A | 11/1997 | Chervitz et al. |
| 5,743,914 A | 4/1998 | Skiba |
| 5,772,594 A | 6/1998 | Barrick |
| 5,823,975 A | 10/1998 | Stark et al. |
| 5,888,224 A | 3/1999 | Beckers et al. |
| 5,891,150 A | 4/1999 | Chan |
| 5,919,193 A | 7/1999 | Slavitt |
| 5,928,239 A | 7/1999 | Mirza |
| 5,929,782 A | 7/1999 | Stark et al. |
| 5,993,463 A | 11/1999 | Truwit |
| 6,053,916 A | 4/2000 | Moore |
| 6,056,749 A | 5/2000 | Kuslich |
| 6,063,442 A | 5/2000 | Cohen et al. |
| 6,175,758 B1 | 1/2001 | Kambin |
| 6,184,797 B1 | 2/2001 | Stark et al. |
| 6,236,891 B1 | 5/2001 | Ingle et al. |
| 6,241,771 B1 | 6/2001 | Gresser et al. |
| 6,290,724 B1 | 9/2001 | Marino |
| 6,296,595 B1 | 10/2001 | Stark et al. |
| 6,302,885 B1 | 10/2001 | Essiger |
| 6,322,562 B1 | 11/2001 | Wolter |
| 6,371,123 B1 | 4/2002 | Stark et al. |
| 6,413,278 B1 | 7/2002 | Marchosky |
| 6,432,107 B1 | 8/2002 | Ferree |
| 6,432,140 B1 | 8/2002 | Lin |
| 6,515,593 B1 | 2/2003 | Stark et al. |
| 6,520,990 B1 | 2/2003 | Ray |
| 6,540,707 B1 | 4/2003 | Stark et al. |
| 6,547,795 B2 | 4/2003 | Schneiderman |
| 6,547,823 B2 | 4/2003 | Scarborough et al. |
| 6,558,423 B1 | 5/2003 | Michelson |
| 6,565,605 B2 | 5/2003 | Goble et al. |
| 6,572,622 B1 | 6/2003 | Shäfer et al. |
| 6,579,318 B2 | 6/2003 | Varga et al. |
| 6,607,487 B2 | 8/2003 | Chang et al. |
| 6,635,059 B2 | 10/2003 | Randall et al. |
| 6,641,614 B1 | 11/2003 | Wagner |
| 6,660,224 B2 | 12/2003 | Lefebvre et al. |
| 6,663,669 B1 | 12/2003 | Reiley |
| 6,669,698 B1 * | 12/2003 | Tromanhauser ... A61B 17/1615 606/104 |
| 6,682,563 B2 | 1/2004 | Scharf |
| 6,682,567 B1 | 1/2004 | Schroeder |
| 6,716,245 B2 | 4/2004 | Pasquet et al. |
| 6,723,099 B1 | 4/2004 | Goshert |
| 6,743,256 B2 | 6/2004 | Mason |
| 6,746,451 B2 | 6/2004 | Middleton et al. |
| 6,824,564 B2 | 11/2004 | Crozet |
| 6,827,670 B1 | 12/2004 | Stark et al. |
| 6,835,208 B2 | 12/2004 | Marchosky |
| 6,855,166 B2 | 2/2005 | Kohrs |
| 6,855,167 B2 | 2/2005 | Shimp et al. |
| 6,860,902 B2 | 3/2005 | Reiley |
| 6,872,187 B1 | 3/2005 | Stark et al. |
| 6,875,236 B2 | 4/2005 | Reiley |
| 6,902,567 B2 | 6/2005 | Del Medico |
| 6,908,465 B2 | 6/2005 | von Hoffmann et al. |
| 6,945,448 B2 | 9/2005 | Medlin et al. |
| 6,972,019 B2 | 12/2005 | Michelson |
| 6,974,461 B1 | 12/2005 | Wolter |
| 7,011,660 B2 | 3/2006 | Sherman et al. |
| 7,087,056 B2 | 8/2006 | Vaughan |
| 7,087,058 B2 | 8/2006 | Cragg |
| 7,108,828 B2 | 9/2006 | Lefebvre et al. |
| 7,144,399 B2 | 12/2006 | Hayes et al. |
| 7,163,560 B2 | 1/2007 | Mason |
| 7,192,447 B2 | 3/2007 | Rhoda |
| 7,201,775 B2 | 4/2007 | Gorensek et al. |
| 7,208,222 B2 | 4/2007 | Rolfe et al. |
| 7,217,291 B2 | 5/2007 | Zucherman et al. |
| 7,229,448 B2 | 6/2007 | Goble et al. |
| 7,235,101 B2 | 6/2007 | Berry et al. |
| 7,235,105 B2 | 6/2007 | Jackson |
| 7,247,157 B2 | 7/2007 | Prager et al. |
| 7,255,712 B1 | 8/2007 | Steinberg |
| 7,303,563 B2 | 12/2007 | Poyner et al. |
| 7,331,995 B2 | 2/2008 | Eisermann et al. |
| 7,396,360 B2 | 7/2008 | Lieberman |
| 7,410,501 B2 | 8/2008 | Michelson |
| 7,416,537 B1 | 8/2008 | Stark et al. |
| 7,458,991 B2 | 12/2008 | Wang et al. |
| 7,465,317 B2 | 12/2008 | Malberg et al. |
| 7,520,898 B2 | 4/2009 | Re et al. |
| 7,537,616 B1 | 5/2009 | Branch et al. |
| 7,575,600 B2 | 8/2009 | Zucherman et al. |
| 7,621,939 B2 | 11/2009 | Zucherman et al. |
| 7,635,447 B2 | 12/2009 | Hamman et al. |
| 7,637,954 B2 | 12/2009 | Michelson |
| 7,641,697 B2 | 1/2010 | Reiley |
| 7,648,509 B2 | 1/2010 | Stark |
| 7,666,209 B2 | 2/2010 | Zucherman et al. |

(56) References Cited

U.S. PATENT DOCUMENTS

| | | |
|---|---|---|
| 7,670,383 B1 | 3/2010 | Brown et al. |
| 7,704,279 B2 | 4/2010 | Moskowitz et al. |
| 7,713,290 B2 | 5/2010 | Vaughan |
| 7,740,795 B2 | 6/2010 | Wang et al. |
| 7,771,441 B2 | 8/2010 | Cerundolo |
| 7,789,895 B2 | 9/2010 | Heinz |
| 7,794,465 B2 | 9/2010 | Marik et al. |
| 7,799,081 B2 | 9/2010 | McKinley |
| 7,819,869 B2 | 10/2010 | Godara et al. |
| 7,824,404 B2 | 11/2010 | Godara et al. |
| 7,837,732 B2 | 11/2010 | Zucherman et al. |
| 7,837,734 B2 | 11/2010 | Zucherman et al. |
| 7,846,162 B2 | 12/2010 | Nelson et al. |
| 7,850,690 B2 | 12/2010 | Frigg et al. |
| 7,850,719 B2 | 12/2010 | Gournay et al. |
| 7,850,732 B2 | 12/2010 | Heinz |
| 7,909,871 B2 | 3/2011 | Abdou |
| 7,918,891 B1 | 4/2011 | Curran et al. |
| 7,922,765 B2 | 4/2011 | Reiley |
| 7,963,970 B2 | 6/2011 | Marino et al. |
| 7,972,363 B2 | 7/2011 | Moskowitz et al. |
| 7,972,382 B2 | 7/2011 | Foley et al. |
| 7,985,255 B2 | 7/2011 | Bray et al. |
| 8,034,114 B2 | 10/2011 | Reiley |
| 8,034,115 B2 | 10/2011 | Reiley |
| 8,048,164 B2 | 11/2011 | Reiley |
| 8,070,782 B2 | 12/2011 | McKay |
| 8,075,561 B2 | 12/2011 | Wolter |
| 8,083,796 B1 | 12/2011 | Raiszadeh et al. |
| 8,088,163 B1 | 1/2012 | Kleiner |
| 8,128,666 B2 | 3/2012 | Falahee |
| 8,162,981 B2 | 4/2012 | Vestgaarden |
| 8,187,332 B2 | 5/2012 | McLuen |
| 8,202,305 B2 | 6/2012 | Reiley |
| 8,221,428 B2 | 7/2012 | Trieu |
| 8,231,661 B2 | 7/2012 | Carls et al. |
| 8,308,779 B2 | 11/2012 | Reiley |
| 8,308,794 B2 | 11/2012 | Martinson et al. |
| 8,317,862 B2 | 11/2012 | Troger et al. |
| 8,343,189 B2 | 1/2013 | Assell et al. |
| 8,343,219 B2 | 1/2013 | Allain et al. |
| 8,348,950 B2 | 1/2013 | Assell et al. |
| 8,388,667 B2 | 3/2013 | Reiley |
| 8,414,648 B2 | 4/2013 | Reiley |
| 8,425,570 B2 | 4/2013 | Reiley |
| 8,425,603 B2 | 4/2013 | Reichen et al. |
| 8,439,925 B2 | 5/2013 | Marino et al. |
| 8,444,693 B2 | 5/2013 | Reiley |
| 8,454,618 B2 | 6/2013 | Stark |
| 8,470,004 B2 | 6/2013 | Reiley |
| 8,470,037 B2 | 6/2013 | Re et al. |
| 8,480,755 B2 | 7/2013 | Reiley |
| 8,491,572 B2 | 7/2013 | Martinson et al. |
| 8,491,653 B2 | 7/2013 | Zucherman et al. |
| 8,496,712 B2 | 7/2013 | Reiley |
| 8,501,690 B2 | 8/2013 | Stark |
| 8,518,120 B2 | 8/2013 | Glerum |
| 8,551,171 B2 | 10/2013 | Johnson et al. |
| 8,579,912 B2 | 11/2013 | Isaza et al. |
| 8,585,744 B2 | 11/2013 | Duggal et al. |
| D697,209 S | 1/2014 | Walthall, Jr. et al. |
| 8,623,062 B2 | 1/2014 | Kondrashov |
| 8,778,026 B2 | 7/2014 | Mauldin |
| 8,808,305 B2 | 8/2014 | Kleiner |
| 8,808,336 B2 | 8/2014 | Duggal et al. |
| 8,808,377 B2 | 8/2014 | Donner |
| 8,808,380 B2 | 8/2014 | Fox et al. |
| 8,808,389 B2 | 8/2014 | Reiley |
| 8,821,546 B2 | 9/2014 | Vaughan |
| 8,840,651 B2 | 9/2014 | Reiley |
| 8,894,708 B2 | 11/2014 | Thalgott et al. |
| 8,979,928 B2 | 3/2015 | Donner |
| 8,992,579 B1 | 3/2015 | Gustine et al. |
| 9,044,321 B2 | 6/2015 | Mauldin |
| 9,060,815 B1 | 6/2015 | Gustine et al. |
| 2001/0005796 A1 | 6/2001 | Zdeblick et al. |
| 2001/0018616 A1 | 8/2001 | Schwab |
| 2001/0020143 A1 | 9/2001 | Stark et al. |
| 2002/0029784 A1 | 3/2002 | Stark et al. |
| 2002/0032484 A1 | 3/2002 | Hyde, Jr. |
| 2002/0068977 A1 | 6/2002 | Jackson |
| 2002/0082701 A1 | 6/2002 | Zdeblick et al. |
| 2002/0087161 A1 | 7/2002 | Randall et al. |
| 2002/0147461 A1 | 10/2002 | Aldrich et al. |
| 2002/0147496 A1 | 10/2002 | Belef et al. |
| 2002/0183846 A1 | 12/2002 | Kuslich et al. |
| 2003/0114931 A1 | 6/2003 | Lee et al. |
| 2003/0124486 A1 | 7/2003 | McDevitt |
| 2003/0181981 A1 | 9/2003 | Lemaire |
| 2003/0208202 A1 | 11/2003 | Falahee |
| 2004/0073216 A1 | 4/2004 | Lieberman |
| 2004/0127988 A1 | 7/2004 | Goble et al. |
| 2004/0162558 A1 | 8/2004 | Hegde et al. |
| 2004/0162616 A1 | 8/2004 | Simonton |
| 2004/0186482 A1 | 9/2004 | Kolb et al. |
| 2004/0199256 A1 | 10/2004 | Wang |
| 2004/0220668 A1 | 11/2004 | Eisermann et al. |
| 2004/0228901 A1 | 11/2004 | Trieu |
| 2004/0249675 A1 | 12/2004 | Stark et al. |
| 2004/0260286 A1 | 12/2004 | Ferree |
| 2005/0043660 A1 | 2/2005 | Stark et al. |
| 2005/0101887 A1 | 5/2005 | Stark et al. |
| 2005/0113652 A1 | 5/2005 | Stark et al. |
| 2005/0131539 A1 | 6/2005 | Kohrs |
| 2005/0149192 A1 * | 7/2005 | Zucherman ........ A61B 17/1671 623/17.11 |
| 2005/0154391 A1 | 7/2005 | Doherty et al. |
| 2005/0203515 A1 | 9/2005 | Doherty et al. |
| 2005/0216088 A1 | 9/2005 | McKinley et al. |
| 2005/0240264 A1 | 10/2005 | Tokish, Jr. et al. |
| 2005/0245925 A1 | 11/2005 | Iki et al. |
| 2005/0267482 A1 | 12/2005 | Hyde, Jr. |
| 2005/0273099 A1 | 12/2005 | Baccelli et al. |
| 2006/0054171 A1 | 3/2006 | Dall |
| 2006/0058876 A1 | 3/2006 | McKinley |
| 2006/0069438 A1 | 3/2006 | Zucherman et al. |
| 2006/0085068 A1 | 4/2006 | Barry |
| 2006/0089716 A1 | 4/2006 | Felix |
| 2006/0095134 A1 | 5/2006 | Trieu et al. |
| 2006/0129244 A1 | 6/2006 | Ensign |
| 2006/0147332 A1 | 7/2006 | Jones et al. |
| 2006/0161154 A1 | 7/2006 | McAfee |
| 2006/0167547 A1 | 7/2006 | Suddaby |
| 2006/0229729 A1 | 10/2006 | Gordon |
| 2007/0027543 A1 | 2/2007 | Gimble et al. |
| 2007/0055374 A1 | 3/2007 | Copf, Jr. et al. |
| 2007/0155588 A1 | 7/2007 | Stark et al. |
| 2007/0156241 A1 | 7/2007 | Reiley et al. |
| 2007/0162134 A1 | 7/2007 | Marnay et al. |
| 2007/0179621 A1 | 8/2007 | McClellan, III et al. |
| 2007/0198093 A1 | 8/2007 | Brodke et al. |
| 2007/0225714 A1 | 9/2007 | Gradl |
| 2007/0239164 A1 | 10/2007 | Prager et al. |
| 2007/0265621 A1 | 11/2007 | Matthis et al. |
| 2007/0270879 A1 | 11/2007 | Isaza et al. |
| 2007/0270968 A1 | 11/2007 | Baynham |
| 2007/0276501 A1 | 11/2007 | Betz et al. |
| 2007/0293949 A1 | 12/2007 | Salerni et al. |
| 2007/0299525 A1 | 12/2007 | Binotto |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0039843 A1 | 2/2008 | Abdou |
| 2008/0045968 A1 | 2/2008 | Yu et al. |
| 2008/0065215 A1 | 3/2008 | Reiley |
| 2008/0140082 A1 | 6/2008 | Erdem et al. |
| 2008/0140207 A1 | 6/2008 | Olmos |
| 2008/0154314 A1 | 6/2008 | McDevitt |
| 2008/0154377 A1 | 6/2008 | Voellmicke |
| 2008/0183293 A1 | 7/2008 | Parry et al. |
| 2008/0228276 A1 | 9/2008 | Mathews et al. |
| 2008/0262621 A1 | 10/2008 | Gorek |
| 2008/0281425 A1 | 11/2008 | Thalgott et al. |
| 2008/0288081 A1 | 11/2008 | Scrafton et al. |

(56) References Cited

U.S. PATENT DOCUMENTS

| | | |
|---|---|---|
| 2008/0300685 A1 | 12/2008 | Carls et al. |
| 2009/0018660 A1 | 1/2009 | Roush |
| 2009/0024174 A1 | 1/2009 | Stark |
| 2009/0024217 A1 | 1/2009 | Levy |
| 2009/0043394 A1 | 2/2009 | Zdeblick et al. |
| 2009/0076553 A1 | 3/2009 | Wolter |
| 2009/0088849 A1 | 4/2009 | Armstrong et al. |
| 2009/0105833 A1 | 4/2009 | Hovda et al. |
| 2009/0105834 A1 | 4/2009 | Hovda et al. |
| 2009/0131986 A1 | 5/2009 | Lee et al. |
| 2009/0132035 A1 | 5/2009 | Roth et al. |
| 2009/0149957 A1 | 6/2009 | Burd et al. |
| 2009/0192621 A1 | 7/2009 | Winslow et al. |
| 2009/0216238 A1 | 8/2009 | Stark |
| 2009/0216276 A1 | 8/2009 | Pasquet |
| 2009/0248163 A1 | 10/2009 | King et al. |
| 2009/0259261 A1 | 10/2009 | Reiley |
| 2009/0259316 A1 | 10/2009 | Ginn et al. |
| 2009/0287254 A1 | 11/2009 | Nayet et al. |
| 2009/0306671 A1 | 12/2009 | McCormack et al. |
| 2010/0057204 A1 | 3/2010 | Kadaba |
| 2010/0076443 A1 | 3/2010 | Bertagnoli et al. |
| 2010/0094290 A1 | 4/2010 | Vaidya |
| 2010/0100135 A1 | 4/2010 | Phan |
| 2010/0106200 A1 | 4/2010 | Stark |
| 2010/0121160 A1 | 5/2010 | Stark et al. |
| 2010/0137910 A1 | 6/2010 | Cawley et al. |
| 2010/0137919 A1 | 6/2010 | Wolter |
| 2010/0152785 A1 | 6/2010 | Forton et al. |
| 2010/0179552 A1 | 7/2010 | Wolter |
| 2010/0185292 A1 | 7/2010 | Hochschuler |
| 2010/0204795 A1 | 8/2010 | Greenhalgh |
| 2010/0211176 A1 | 8/2010 | Greenhalgh |
| 2010/0268228 A1 | 10/2010 | Petersen |
| 2010/0286779 A1 | 11/2010 | Thibodeau |
| 2010/0286785 A1 | 11/2010 | Grayson |
| 2010/0292796 A1 | 11/2010 | Greenhalgh |
| 2010/0292800 A1 | 11/2010 | Zubok |
| 2010/0305702 A1 | 12/2010 | Michelson |
| 2010/0305704 A1 | 12/2010 | Messerli |
| 2010/0324607 A1 | 12/2010 | Davis |
| 2010/0331981 A1 | 12/2010 | Mohammed |
| 2011/0034957 A1 | 2/2011 | Biedermann |
| 2011/0046737 A1 | 2/2011 | Teisen |
| 2011/0071568 A1 | 3/2011 | Ginn et al. |
| 2011/0071635 A1 | 3/2011 | Zhang et al. |
| 2011/0087294 A1 | 4/2011 | Reiley |
| 2011/0093074 A1 | 4/2011 | Glerum |
| 2011/0098816 A1 | 4/2011 | Jacob et al. |
| 2011/0098817 A1 | 4/2011 | Eckhardt et al. |
| 2011/0118796 A1 | 5/2011 | Reiley |
| 2011/0172774 A1 | 7/2011 | Varela |
| 2011/0184518 A1 | 7/2011 | Trieu |
| 2011/0184519 A1* | 7/2011 | Trieu ............... A61B 17/7076 623/17.11 |
| 2011/0184520 A1 | 7/2011 | Trieu |
| 2011/0185306 A1 | 7/2011 | Aravamudan |
| 2011/0230966 A1 | 9/2011 | Trieu |
| 2011/0238181 A1* | 9/2011 | Trieu ............... A61B 17/1735 623/17.11 |
| 2011/0264233 A1 | 10/2011 | Song |
| 2011/0295272 A1 | 12/2011 | Assell et al. |
| 2012/0010714 A1 | 1/2012 | Moskowitz et al. |
| 2012/0022535 A1 | 1/2012 | Mayer et al. |
| 2012/0022595 A1 | 1/2012 | Pham et al. |
| 2012/0029641 A1 | 2/2012 | Curran et al. |
| 2012/0035729 A1 | 2/2012 | Glerum |
| 2012/0083883 A1 | 4/2012 | Ginn |
| 2012/0095560 A1* | 4/2012 | Donner ............... A61F 2/30988 623/17.11 |
| 2012/0101582 A1 | 4/2012 | Raiszadeh et al. |
| 2012/0116454 A1 | 5/2012 | Edidin et al. |
| 2012/0116806 A1 | 5/2012 | Stark et al. |
| 2012/0150300 A1 | 6/2012 | Nihalani |
| 2012/0185049 A1 | 7/2012 | Varela |
| 2012/0209388 A1 | 8/2012 | Curran et al. |
| 2012/0215315 A1 | 8/2012 | Hochschuler et al. |
| 2012/0253398 A1 | 10/2012 | Metcalf et al. |
| 2012/0259370 A1 | 10/2012 | Vaidya |
| 2012/0271200 A1 | 10/2012 | Martinson et al. |
| 2012/0271424 A1 | 10/2012 | Crawford |
| 2012/0296428 A1 | 11/2012 | Donner |
| 2012/0316565 A1 | 12/2012 | Stark |
| 2012/0323285 A1 | 12/2012 | Assell et al. |
| 2013/0006361 A1 | 1/2013 | Glerum |
| 2013/0018427 A1 | 1/2013 | Pham et al. |
| 2013/0023994 A1 | 1/2013 | Glerum |
| 2013/0030456 A1 | 1/2013 | Assell et al. |
| 2013/0035723 A1 | 2/2013 | Donner |
| 2013/0035727 A1 | 2/2013 | Datta |
| 2013/0053854 A1 | 2/2013 | Schoenefeld et al. |
| 2013/0053902 A1 | 2/2013 | Trudeau |
| 2013/0053964 A1 | 2/2013 | Talwar |
| 2013/0060337 A1 | 3/2013 | Petersheim et al. |
| 2013/0066426 A1 | 3/2013 | Martinson et al. |
| 2013/0085535 A1 | 4/2013 | Greenhalgh et al. |
| 2013/0090735 A1 | 4/2013 | Mermuys et al. |
| 2013/0116790 A1 | 5/2013 | Seifert |
| 2013/0123850 A1 | 5/2013 | Schoenefeld et al. |
| 2013/0123923 A1 | 5/2013 | Pavlov et al. |
| 2013/0144343 A1 | 6/2013 | Arnett et al. |
| 2013/0158669 A1 | 6/2013 | Sungarian |
| 2013/0197590 A1 | 8/2013 | Assell et al. |
| 2013/0218215 A1 | 8/2013 | Ginn et al. |
| 2013/0226181 A1 | 8/2013 | Assell et al. |
| 2013/0231746 A1 | 9/2013 | Ginn et al. |
| 2013/0245703 A1 | 9/2013 | Warren et al. |
| 2013/0253650 A1 | 9/2013 | Ashley |
| 2013/0282012 A1 | 10/2013 | Stark |
| 2013/0295202 A1 | 11/2013 | Stark |
| 2013/0297035 A1 | 11/2013 | Reiley |
| 2014/0012330 A1 | 1/2014 | Johnson, II et al. |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0039628 A1 | 2/2014 | DeLurio et al. |
| 2014/0046380 A1 | 2/2014 | Asfora |
| 2014/0074175 A1 | 3/2014 | Ehler et al. |
| 2014/0088707 A1 | 3/2014 | Donner et al. |
| 2014/0100662 A1 | 4/2014 | Patterson et al. |
| 2014/0114415 A1 | 4/2014 | Tyber |
| 2014/0135850 A1 | 5/2014 | Parent et al. |
| 2014/0135927 A1 | 5/2014 | Pavlov et al. |
| 2014/0156007 A1 | 6/2014 | Pabst et al. |
| 2014/0200618 A1 | 7/2014 | Donner et al. |
| 2014/0249581 A1 | 9/2014 | Stachniak |
| 2014/0257294 A1 | 9/2014 | Gedet et al. |
| 2014/0257399 A1 | 9/2014 | Rezach |
| 2014/0257408 A1 | 9/2014 | Trieu et al. |
| 2014/0257411 A1 | 9/2014 | Rezach |
| 2014/0257486 A1 | 9/2014 | Alheidt |
| 2014/0277460 A1 | 9/2014 | Schifano |
| 2014/0277478 A1 | 9/2014 | Moore |
| 2014/0277504 A1 | 9/2014 | Forton et al. |
| 2014/0288601 A1 | 9/2014 | Baynham |
| 2014/0336763 A1* | 11/2014 | Donner ............... A61F 2/30988 623/17.11 |
| 2014/0336775 A1 | 11/2014 | Reiley |
| 2014/0343678 A1 | 11/2014 | Suddaby et al. |
| 2015/0039037 A1 | 2/2015 | Donner et al. |
| 2015/0150683 A1 | 6/2015 | Donner et al. |
| 2015/0182268 A1 | 7/2015 | Donner et al. |
| 2015/0209087 A1 | 7/2015 | Donner et al. |
| 2015/0250612 A1 | 9/2015 | Schifano |
| 2015/0342753 A1 | 12/2015 | Donner et al. |
| 2016/0157897 A1 | 6/2016 | Vaidya |
| 2016/0184105 A1 | 6/2016 | Donner et al. |
| 2016/0324643 A1 | 11/2016 | Donner et al. |

FOREIGN PATENT DOCUMENTS

| | | |
|---|---|---|
| CN | 201073333 Y | 6/2008 |
| CN | 201139628 | 10/2008 |
| CN | 201275132 | 7/2009 |

(56) References Cited

FOREIGN PATENT DOCUMENTS

| | | |
|---|---|---|
| CN | 201275133 | 7/2009 |
| CN | 201275134 | 7/2009 |
| CN | 202235633 U | 5/2012 |
| DE | 102013011322 A1 | 5/2014 |
| EP | 1663037 B1 | 6/2006 |
| JP | 2007-275592 | 10/2007 |
| KR | 10-1037206 | 5/2011 |
| RU | 2364359 C1 | 8/2009 |
| WO | WO 93/08745 A1 | 5/1993 |
| WO | WO 95/23559 | 9/1995 |
| WO | WO 95/31947 | 11/1995 |
| WO | WO 98/48717 | 11/1998 |
| WO | WO 01/30264 A2 | 5/2001 |
| WO | WO 01/95823 A1 | 12/2001 |
| WO | WO 02/067759 A2 | 9/2002 |
| WO | WO 02/085182 A2 | 10/2002 |
| WO | WO 2006/020463 A1 | 2/2006 |
| WO | WO 2006/099270 | 9/2006 |
| WO | WO 2007/022790 A1 | 3/2007 |
| WO | WO 2007/115295 A2 | 10/2007 |
| WO | WO 2008/011410 A2 | 1/2008 |
| WO | WO 2008/088685 A2 | 7/2008 |
| WO | WO 2008/089537 A1 | 7/2008 |
| WO | WO 2009/011774 A2 | 1/2009 |
| WO | WO 2009/029074 A1 | 3/2009 |
| WO | WO 2009/108318 A2 | 9/2009 |
| WO | WO 2010/045749 A1 | 4/2010 |
| WO | WO 2010/065015 A1 | 6/2010 |
| WO | WO 2010/108166 A1 | 9/2010 |
| WO | WO 2011014135 A2 | 2/2011 |
| WO | WO 2011/056690 A2 | 5/2011 |
| WO | WO 2011/066053 A2 | 6/2011 |
| WO | WO 2011/087912 A1 | 7/2011 |
| WO | WO 2011/091349 A2 | 7/2011 |
| WO | WO 2012/015976 A1 | 2/2012 |
| WO | WO 2012/174485 A1 | 12/2012 |
| WO | WO 2013/020123 A2 | 2/2013 |
| WO | WO 2013/166496 A1 | 11/2013 |
| WO | WO 2014/055529 A2 | 4/2014 |
| WO | WO 2014/074853 A1 | 5/2014 |

OTHER PUBLICATIONS

DePuy Spine. ISOLA® Spinopelvic System, Surgical Technique. c. 2003 DePuy Spine, Inc., 28 pages.
Guner, et al. "Anterior Sacroiliac Fusion. A New Video-Assisted Endoscopic Technique." Surgical Laparoscopy & Endoscopy, 8(3), pp. 233-236.
LDR. Avenue® L Lateral Lumbar Cage. Sep. 2011, 3 pages.
LDR. ROI-A™ Anterior Approach Implant. Apr. 2008, 2 pages.
LDR. Surgical Technique ROI-C™ Anterior Cervical Cage. Apr. 2010, 15 pages.
Medtronic Sofamor Danek. Colorado 2™ Sacro-Iliac Fixation, Surgical Technique. © 2003 Medtronic Sofamor Danek USA, Inc.
Medtronic Sofamor Danek. Colorado 2™ The New Revolution, Surgical Technique. © 2000 Medtronic Sofamor Danek, Inc.
Moshirfar et al. Pelvic Fixation in Spine Surgery. The Journal of Bone & Joint Surgery 2005;87-A(2 Suppl):89-106.
SI-Bone iFuse Implant System, Surgical Technique Manual. c. 2011 SI-Bone, Inc., 35 pages.
Synthes GmbH. Sacral Bars. Fixation of the posterior pelvis in cases of fractures or sacroiliac joint dislocations. © Apr. 2009 Synthes, Inc.
Tenon Medical, Catamaran SI Joint Implant, http://tctig.com/projects (last visited Nov. 19, 2014).
Amendment Under 1.312, U.S. Appl. No. 13/946,790, dated Dec. 14, 2015.
EP Examination Report, EP11733183.5, dated Sep. 9, 2015.
European Search Report, EP12834000.7, dated Jul. 13, 2015.
Final Rejection, U.S. Appl. No. 13/945,053, dated Dec. 22, 2015.
Non-Final Office Action, U.S. Appl. No. 13/475,695, dated Jul. 30, 2015.
Notice of Allowance, U.S. Appl. No. 13/946,790, dated Nov. 20, 2015.
Response to Non-Final Office Action, U.S. Appl. No. 13/475,695, dated Oct. 30, 2015.
Response to Non-Final Office Action, U.S. Appl. No. 13/945,053, dated Aug. 31, 2015.
Response to Restriction, U.S. Appl. No. 13/946,790, dated Sep. 14, 2015.
Response to Restriction, U.S. Appl. No. 13/236,411, filed Nov. 12, 2013.
Response to Restriction, U.S. Appl. No. 13/475,695, dated Jun. 30, 2015.
Restriction Requirement, U.S. Appl. No. 13/946,790, dated Jul. 14, 2015.
Restriction Requirement, U.S. Appl. No. 14/216,975, dated Oct. 23, 2015.
U.S. Appl. No. 14/447,612, filed Jul. 31, 2014, JCBD, LLC.
U.S. Appl. No. 14/660,784, filed Mar. 17, 2015, JCBD, LLC.
Australian Examination Report, AU2014204494, dated May 15, 2015.
Chinese Office Action, CN201180001537.4, dated Mar. 19, 2015.
Dall et al., Surgery for the Painful, Dysfunctional Sacroiliac Joint, Springer International Publishing, Switzerland, 2015.
Non-Final Office Action, U.S. Appl. No. 13/945,053, dated Apr. 3, 2015.
Restriction Requirement, U.S. Appl. No. 13/475,695, dated Mar. 30, 2015.
Arman et al. The Human Sacrum and Safe Approaches for Screw Placement. Journal of Clinical Neuroscience 2008 Elsevier Inc. ;16(2009):1046-1049.
Atlihan et al. Anatomy of the Posterior Illiac Crest as a Reference to Sacral Bar Insertion. Clin Orthop 2004;418:141-145.
Belanger, et al. "Sacroiliac Arthrodesis Using a Posterior Midline Fascial Splitting Approach and Pedicle Screw Instrumentation: A New Technique." Journal of Spinal Disorders, vol. 14 No. 2, pp. 118-124, 2001.
Buchowski, et al. "Functional and Radiographic Outcome of Sacroiliac Arthrodesis for the Disorders of the Sacroiliac Joint." The Spine Journal, 5, 2005, pp. 520-528.
Cecil et al. Projection of the S2 Pedicle Onto the Posterolateral Surface of the Ilium: A Technique for Lag Screw Fixation, Sacral Fractures or Sacroiliac Joint Dislocations. Spine 1996;21(7):875-878.
Chang et al. Low Profile Pelvic Fixation. Spine 2009;34(5):436-440.
Dayer R. et al. Pelvic fixation for neuromuscular scoliosis deformity correction. Curr Rev Musculoskelet Med (2012) 5:91-101.
Ebraheim, et al. "A Posterior Approach for Inspection of Reduction of Sacroiliac Joint Disruption." Surg. Radiol. Anat., 1999, 21(5), pp. 305-307.
Ebraheim, et al. "Anatomic considerations for Posterior Approach to the Sacroiliac Joint." Spine, 21(23), Dec. 1, 1996, pp. 2709-2712.
Garrido B.J. et al. Navigated placement of iliac bolts: description of a new technique. The Spine Journal 11 (2011) 331-335.
Giannikas, et al. "Sacroiliac Joint Fusion for Chronic Pain: A Simple Technique Avoiding the Use of Metalwork." Eur. Spine J, 13, 2004, pp. 253-256.
Globus Medical. REVERE® ADDITION® Sacroiliac Components, Surgical Technique. c. 2012 Globus Medical, 64 pages.
Globus Medical. SI-LOK™ Sacroiliac Joint Fixation System, Surgical Technique. c. 2011 Globus Medical, 44 pages.
Lee et al. Trajectory of Transsacral Iliac Screw for Lumbopelvic Fixation. J Spinal Disord Tech 2011;24(3):151-156.
Lehman, Jr. et al. Advantage of Pedicle Screw Fixation Directed Into the Apex of the Sacral Promontory Over Bicortical Fixation. Spine 2002;27(8):806-811.
Liebergall, Meir (Iri) M.D., Lumbosacral and Spinopelvic Fixation, Lippincott-Raven, Philadelphia, PA, 1996, Chap. 48, "Sacroiliac Joint Fusion," pp. 611-618.
Luk et al. A Stronger Bicortical Sacral Pedicle Screw Fixation Through the S1 Endplate. Spine 2005;30(5):525-529.

(56) References Cited

OTHER PUBLICATIONS

Margulies, J.Y. et al., *Movement, Stability & Low Back Pain, The essential role of the pelvis*, Churchill Livingstone, London, 1997, Chapters 44-47, "Surgical Fusion of the Spine to the Sacrum, etc.," pp. 555-593.
Marotta N. et al. A novel minimally invasive presacral approach and instrumentation technique for anterior L5-S1 intervertebral disectomy and fusion. *Neurosurg Focus*, vol. 20, Jan. 2006, 8 pages.
Martin et al. Sacropelvic Fixation: Two Case Reports of a New Percutaneous Technique. *Spine* 2011;36(9):E618-21.
McLauchlan, et al. "Sacral and Iliac Articular Cartilage Thickness and Cellularity: Relationship to Subchrondral Bone End-Plate Thickness and Cancellous Bone Density." Rheumatology 2002; 41:375-380.
Mendel et al. The Lateral Sacral Triangle—A Decision Support for Secure Transverse Sacroiliac Screw Insertion. *Injury J. Care Injured* 2010;42(2011):1164-1170.
O'Brien et al. An Anatomic Study of the S2 Iliac Technique for Lumbopelvic Screw Placement. *Spine* 2009;34(12):E439-E442.
O'Brien et al. Feasibility of Minimally Invasive Sacropelvic Fixation. *Spine* 2010;35(4):460-464.
O'Brien et al. Sacropelvic Instrumentation: Anatomic and Biomechanical Zones of Fixation. *Seminars in Spine Surgery* 2004;16(2):76-90.
Ouellet et al. Surgical Anatomy of the Pelvis, Sacrum, and Lumbar Spine Relevant to Spinal Surgery. *Seminars in Spine Surgery* 2004 Elsevier Inc.;16:91-100.
Pan W. et al. The invention of an iliosacral screw fixation guide and its preliminary clinical application. *Orthopaedic Surgery* (2012), vol. 4, No. 1, pp. 55-59.
Puhakka, et al. "MR Imaging of the Normal Sacroiliac Joint with Correlation to Histology." Skeletal Radiol., 33, 2004, pp. 15-28.
SI-Bone iFuse Implant System™. SI-Bone, Inc. 2010, 4 pages.
Signus Medizintechnik GmbH. Diana Operationstechnik. Rev. May 1, 2010, 20 pages.
Sponseller P.D. et al. Low profile pelvic fixation with the sacral alar iliac technique in the pediatric population improves results at two-year mninimum follow-up. *Spine* vol. 35, No. 20, pp. 1887-1892.
Stark J. G. et al. The history of sacroiliac joint arthrodesis: a critical review and introduction of a new technique. *Current Orthopaedic Practice*, vol. 22, No. 6, Nov./Dec. 2011, pp. 545-557.
Stark. "The Diagnosis and Treatment of Sacroiliac Joint Abnormalities." Current Orthopedic Practice, 21(4), Jul./Aug. 2010, pp. 336-347.
Synthes Spine. ProDisc-C Total Disc Replacement. Product Information. ©2008 Synthes, Inc., 14 pages.
Synthes Spine. SynFix-LR System. Instruments and implants for stand-alone anterior lumbar interbody fusion (ALIF). Technique Guide. ©2008 Synthes, Inc., 45 pages.
Synthes Spine. Universal Spinal System (USS) Polyaxial and Iliosacral Spine Fixation. A versatile system for posterior stabilization of spinal segments. Technique Guide, c. 2009 Synthes, Inc., 61 pages.
Szadek, et al. "Possible Nociceptive Structures in the Sacroiliac Joint Cartilage: An Immunohistochemical Study." Clinical Anatomy, 23, 2010, pp. 192-198.
Tifix® Technology Pressure Plate Technology: Multidirectional Locking Technology Titanium Plate and Screw Systems, General & Specific Instructions. litos/GmbH & Co. KG, Rev: Sep. 9, 2008.
Tobler W.D. et al. The presacral retroperitoneal approach for axial lumbar interbody fusion. *J Bone Joint Surg [Br]*, vol. 93-B, No. 7, Jul. 2011, pp. 955-960.
Ugur, et al. "New Needle Holder Facilitates Percutaneous Fluoroscopy-Guided Sacroiliac Puncture." Acta Radiologica, 2006, 47(5), pp. 481-483.
Vanelderen, et al. "Evidence-Based Medicine. Evidence-Based Interventional Pain Medicine According to Clinical Diagnoses. 13. Sacroiliac Joint Pain." Pain Practice, 10(5), 2010, pp. 470-478.
Waisbrod, et al. "Sacroiliac Joint Arthrodesis for Chronic Lower Back Pain." Arch. Orthop. Trauma Surg., 106, 1987, pp. 238-240.
Wise, et al. "Minimally Invasive Sacroiliac Arthrodesis. Outcomes of a New Technique." Spinal Disord. Tech., 21(8), Dec. 2008, pp. 579-584.
Yin, et al. "Sensory Stimulation-Guided Sacroiliac Joint Radiofrequency Neurotomy: Technique Based on Neuroanatomy of the Dorsal Sacral Plexus." Spine, 28(20), pp. 2419-2425.
Zyga Technology, Inc. Slmmetry Sacroiliac Joint Fusion System, Surgeon Didactic, c. 2012 Zyga Technology, Inc., 45 pages.
Zyga Technology, Inc. Slmmetry Sacroiliac Joint Fusion System, Technique Guide, known at least as early as Mar. 1, 2013, 20 pages.
Advisory Action, U.S. Appl. No. 12/998,712, dated Jan. 28, 2014, 4 pages.
Advisory Action, U.S. Appl. No. 13/135,381, mailed Jul. 23, 2013, 3 pages.
Appeal Brief, U.S. Appl. No. 13/135,381, dated Dec. 23, 2013, 20 pages.
European Search Report, EP Appl. No. 11733183.5, dated Dec. 18, 2013, 4 pages.
European Search Report, EP Appl. No. 12799773.2, dated Oct. 29, 2014.
Examination Report, SG Application No. 201205104-1, dated Jul. 17, 2014, Intellectual Property Office of Singapore.
Final Rejection, U.S. Appl. No. 12/998,712, mailed Nov. 7, 2013, 24 pages.
Final Rejection, U.S. Appl. No. 13/135,381, mailed May 9, 2013, 14 pages.
Final Rejection, U.S. Appl. No. 13/236,411, dated Jan. 2, 2015.
International Search Report and Written Opinion, PCT application No. PCT/US2012/042823, dated Nov. 5, 2012, 16 pages.
International Search Report and Written Opinion, PCT Application No. PCT/US2012/055892, dated Mar. 25, 2013, 22 pages.
International Search Report and Written Opinion, PCT application No. PCT/US2011/000070, dated Mar. 21, 2011, 13 pages.
International Search Report and Written Opinion, PCT Application No. PCT/US2013/051381, dated Nov. 4, 2013, 16 pages.
International Search Report and Written Opinion, PCT/US2014/030889, dated Jul. 16, 2014.
International Search Report and Written Opinion, PCT/US2014/048990, dated Nov. 18, 2014.
Japanese Office Action, JP2012-548960, dated Oct. 7, 2014.
Non-Final Office Action, U.S. Appl. No. 12/998,712, mailed May 31, 2013, 44 pages.
Non-Final Office Action, U.S. Appl. No. 12/998,712, dated Aug. 1, 2014.
Non-Final Office Action, U.S. Appl. No. 13/135,381, mailed Nov. 5, 2012, 19 pages.
Non-Final Office Action, U.S. Appl. No. 13/236,411, dated Apr. 11, 2014.
Notice of Allowance, U.S. Appl. No. 13/236,411, dated Mar. 16, 2015.
Notice of Allowance, U.S. Appl. No. 12/998,712, dated Dec. 23, 2014.
Notice of Allowance, U.S. Appl. No. 13/135,381, dated Apr. 17, 2014.
Response to Advisory Action, U.S. Appl. No. 13/135,381, filed Aug. 20, 2013, 12 pages.
Response to Final Office Action, U.S. Appl. No. 13/236,411, dated Mar. 4, 2015.
Response to Final Office Action, U.S. Appl. No. 12/998,712, dated Jan. 7, 2014, 16 pages.
Response to Final Office Action, U.S. Appl. No. 13/135,381, filed Jul. 9, 2013, 11 pages.
Response to Non-Final Office Action, U.S. Appl. No. 13/135,381, filed Feb. 4, 2013, 7 pages.
Response to Non-Final Office Action, U.S. Appl. No. 12/998,712, filed Aug. 28, 2013, 17 pages.
Response to Non-Final Office Action, U.S. Appl. No. 12/998,712, dated Sep. 4, 2014.
Response to Non-Final Office Action, U.S. Appl. No. 13/236,411, dated Sep. 11, 2014.

(56) References Cited

OTHER PUBLICATIONS

Response to Restriction, U.S. Appl. No. 13/236,411, filed Jun. 10, 2013, 13 pages.
Response to Restriction, U.S. Appl. No. 13/236,411, filed Nov. 12, 2013, 14 pages.
Response to Restriction, U.S. Appl. No. 13/945,053, dated Nov. 19, 2014.
Restriction Requirement, U.S. Appl. No. 13/236,411, mailed May 10, 2013, 5 pages.
Restriction Requirement, U.S. Appl. No. 13/236,411, mailed Oct. 16, 2013, 7 pages.
Restriction Requirement, U.S. Appl. No. 13/945,053, dated Sep. 25, 2014.
Singapore Search Report and Written Opinion, SG Appl. No. 201205104-1, dated Oct. 31, 2013, 29 pages.
Supplemental Amendment, U.S. Appl. No. 12/998,712, dated Apr. 14, 2014, 14 pages.
Amendment Under 1.312, U.S. Appl. No. 13/475,695, dated Mar. 25, 2016.
Japanese Office Action, JP2015-042238, dated Dec. 22, 2015.
Non-Final Office Action, U.S. Appl. No. 14/413,318, dated May 3, 2016.
Notice of Allowance, U.S. Appl. No. 13/475,695, dated Feb. 18, 2016.
Notice of Allowance, U.S. Appl. No. 13/945,053, dated Mar. 28, 2016.
Notice of Allowance, U.S. Appl. No. 13/946,790, dated Feb. 16, 2016.
Response to Restriction, U.S. Appl. No. 14/216,975, dated Jan. 22, 2016.
Response to Restriction, U.S. Appl. No. 14/413,318, dated Apr. 19, 2016.
Restriction Requirement, U.S. Appl. No. 14/127,119, dated Apr. 5, 2016.
Restriction Requirement, U.S. Appl. No. 14/413,318, dated Feb. 19, 2016.
Taiwan Examination Report, TW100114376, dated Oct. 5, 2015.
Amendment and Response to Restriction, U.S. Appl. No. 14/447,612, dated Sep. 2, 2016.
Amendment Under 1.312, U.S. Appl. No. 13/945,053, dated May 19, 2016.
AU Patent Examination Report No. 1, AU2012312658, dated Jul. 18, 2016.
Canadian Office Action, CA2787152, dated Jan. 25, 2017.
EP Extended Search Report, EP16191003.9, dated Feb. 6, 2017.
Final Office Action, U.S. Appl. No. 14/216,975, dated Dec. 30, 2016.
Non-Final Office Action, U.S. Appl. No. 14/127,119, dated Sep. 8, 2016.
Non-Final Office Action, U.S. Appl. No. 14/216,975, dated Jun. 20, 2016.
Non-Final Office Action, U.S. Appl. No. 14/344,876, dated Dec. 1, 2016.
Non-Final Office Action, U.S. Appl. No. 14/447,612, dated Dec. 15, 2016.
Non-Final Office Action, U.S. Appl. No. 14/681,882, dated Oct. 6, 2016.
Notice of Allowance, U.S. Appl. No. 13/945,053, dated Jul. 5, 2016.
Notice of Allowance, U.S. Appl. No. 14/413,318, dated Aug. 31, 2016.
Response to Non-Final Office Action, U.S. Appl. No. 14/413,318, dated Aug. 3, 2016.
Response to Non-Final Office Action, U.S. Appl. No. 14/447,612, dated Jan. 25, 2017.
Response to Non-Final Office Action, U.S. Appl. No. 14/681,882, dated Jan. 5, 2017.
Response to Restriction, U.S. Appl. No. 14/127,119, dated Jun. 6, 2016.
Response to Restriction, U.S. Appl. No. 14/344,876, dated Aug. 29, 2016.
Response to Restriction, U.S. Appl. No. 14/514,221, dated Oct. 24, 2016.
Restriction Requirement, U.S. Appl. No. 14/447,612, dated Jul. 6, 2016.
Restriction Requirement, U.S. Appl. No. 14/514,221, dated Aug. 25, 2016.
Restriction Requirement, U.S. Appl. No. 14/723,384, dated Dec. 29, 2016.
Chinese Office Action, CN201510622898.0, dated Dec. 23, 2016.
Notice of Allowance, U.S. Appl. No. 14/447,612, dated Feb. 28, 2017.
Notice of Allowance, U.S. Appl. No. 14/514,221, dated Feb. 21, 2017.
Response to Final Office Action, U.S. Appl. No. 14/216,975, dated Feb. 27, 2017.
Response to Non-Final Office Action, U.S. Appl. No. 14/344,876, dated Mar. 1, 2017.
Response to Restriction, U.S. Appl. No. 14/723,384, dated Feb. 24, 2017.

\* cited by examiner

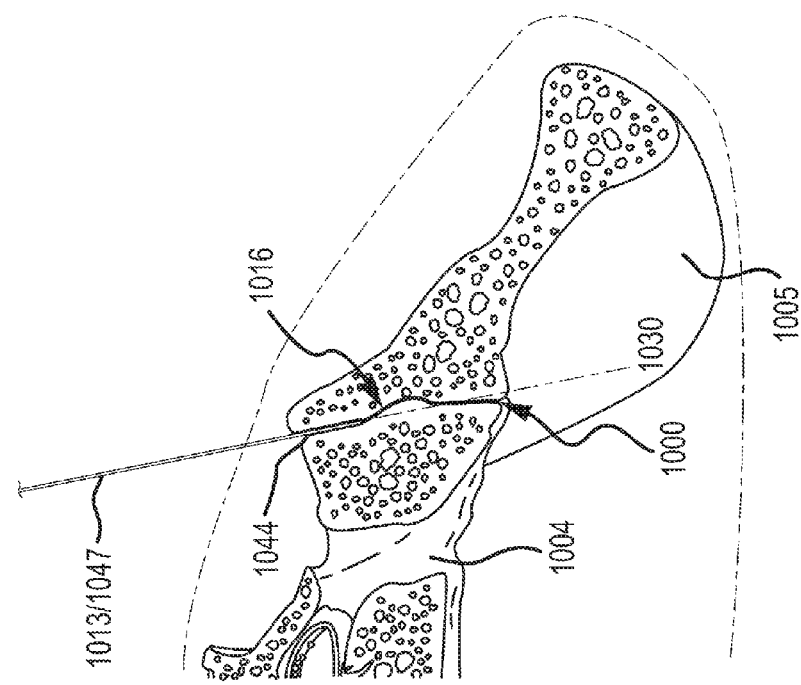
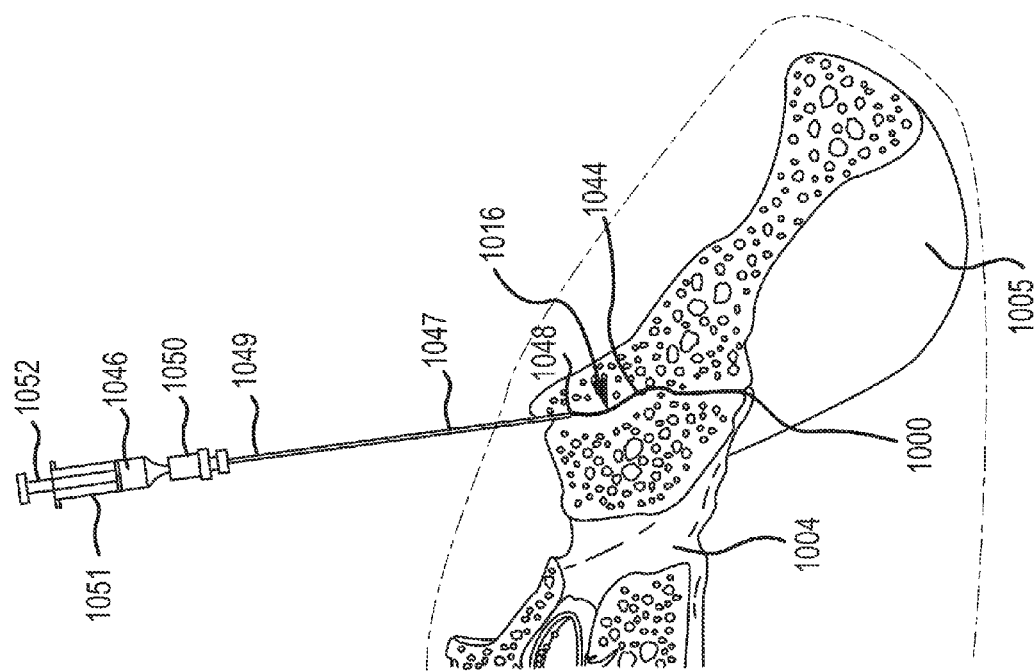

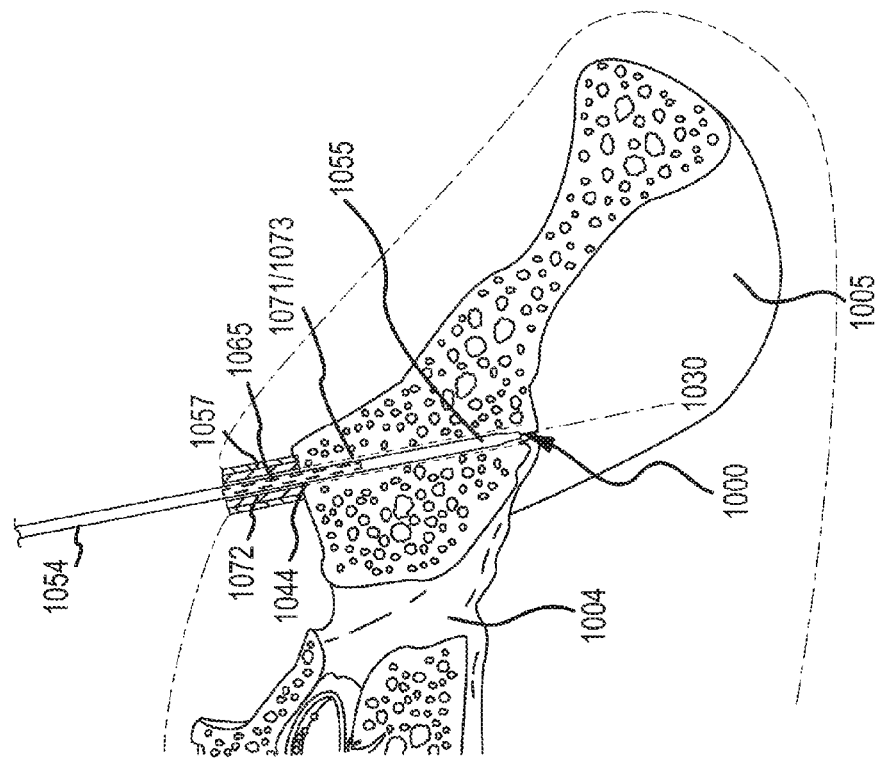
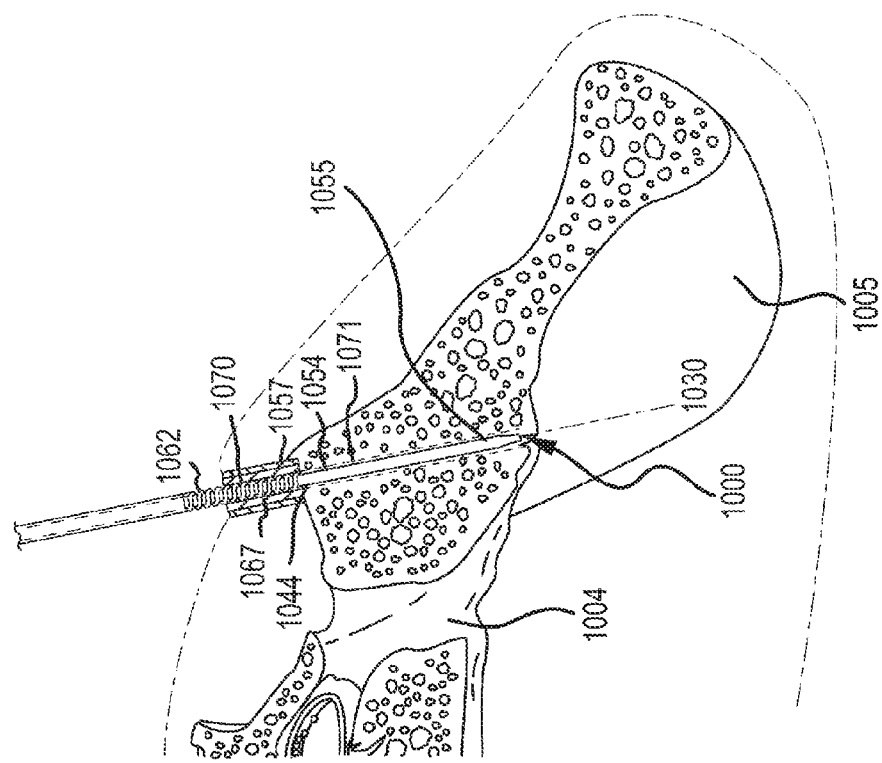
FIG. 12F
FIG. 12E

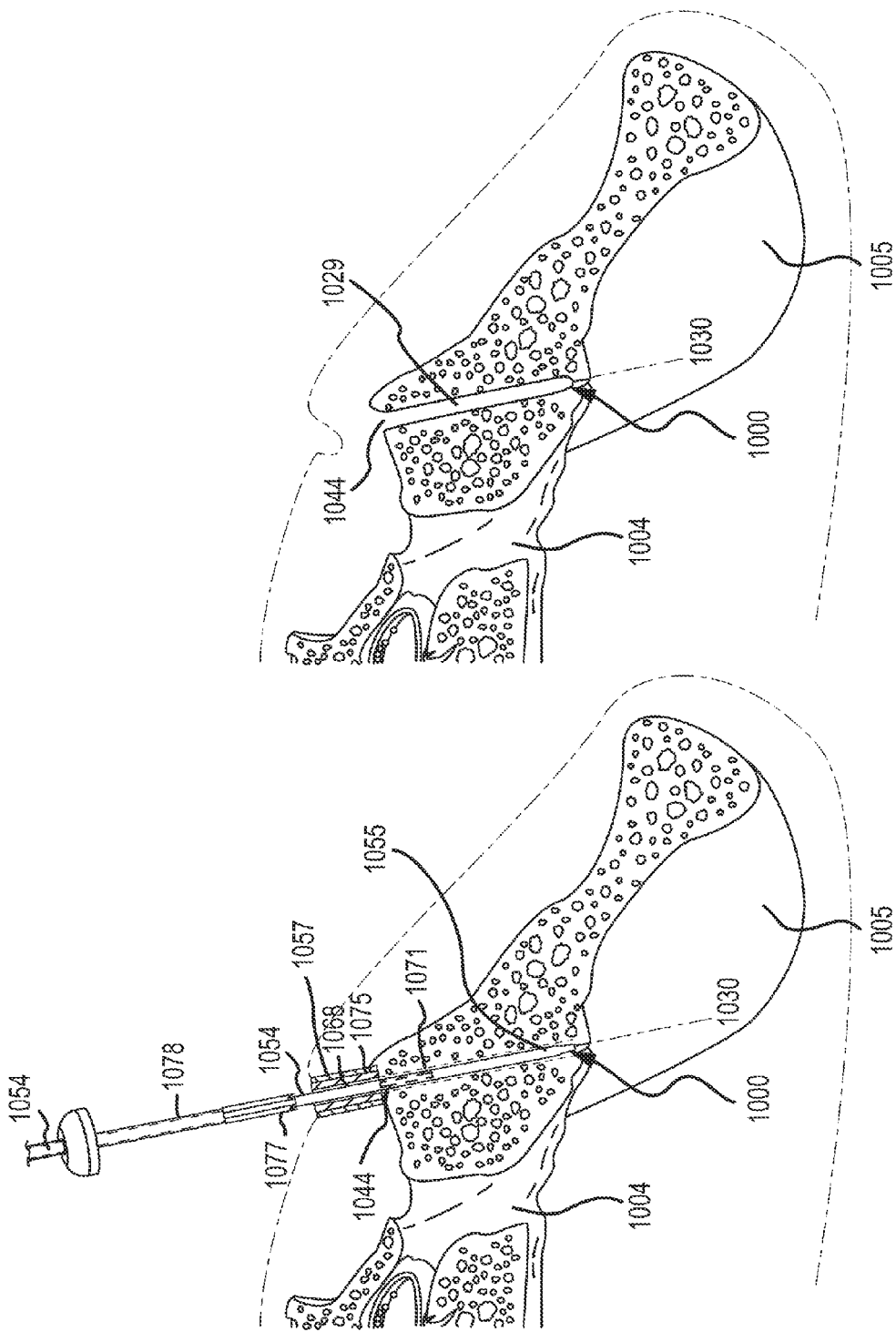

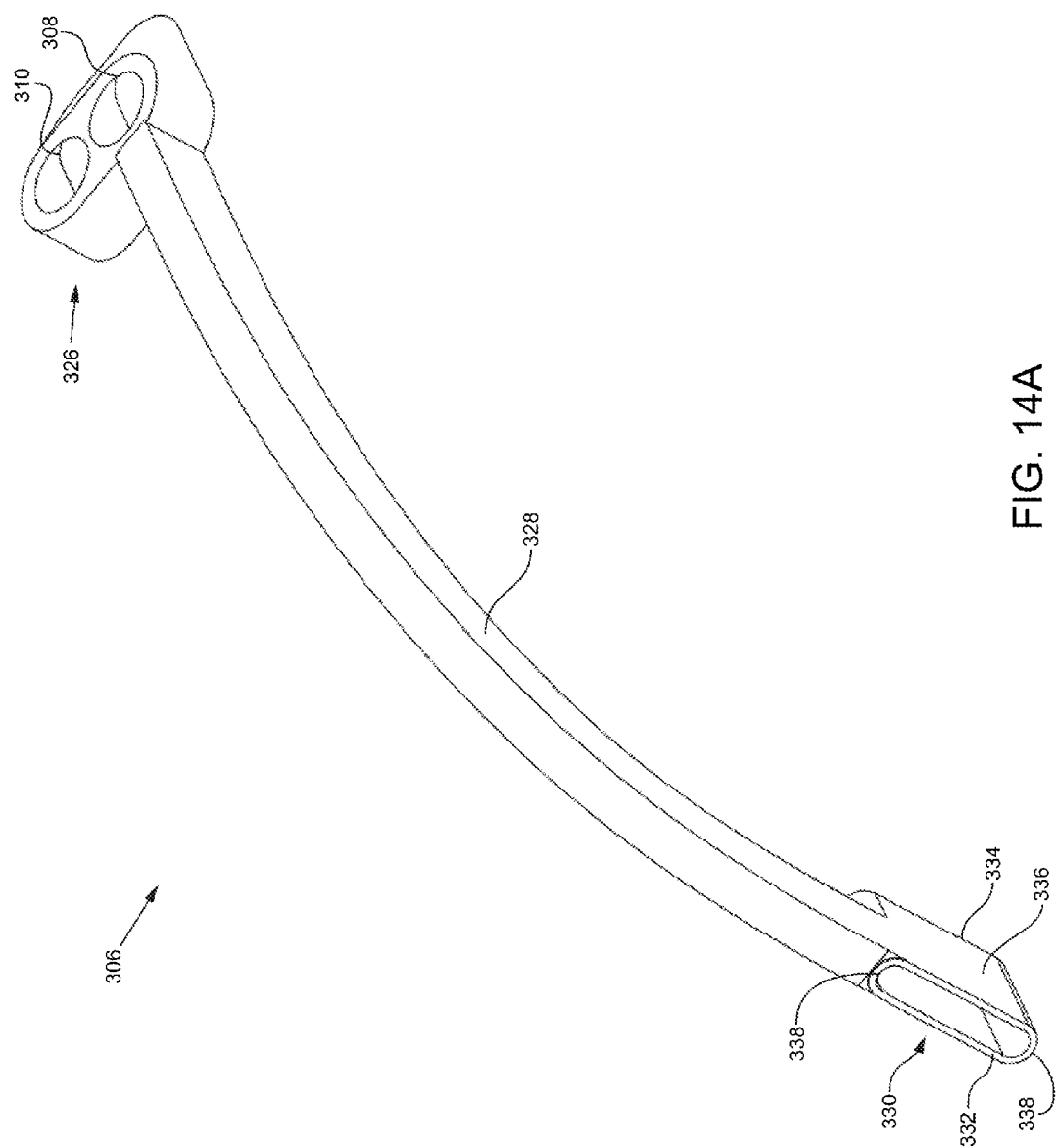

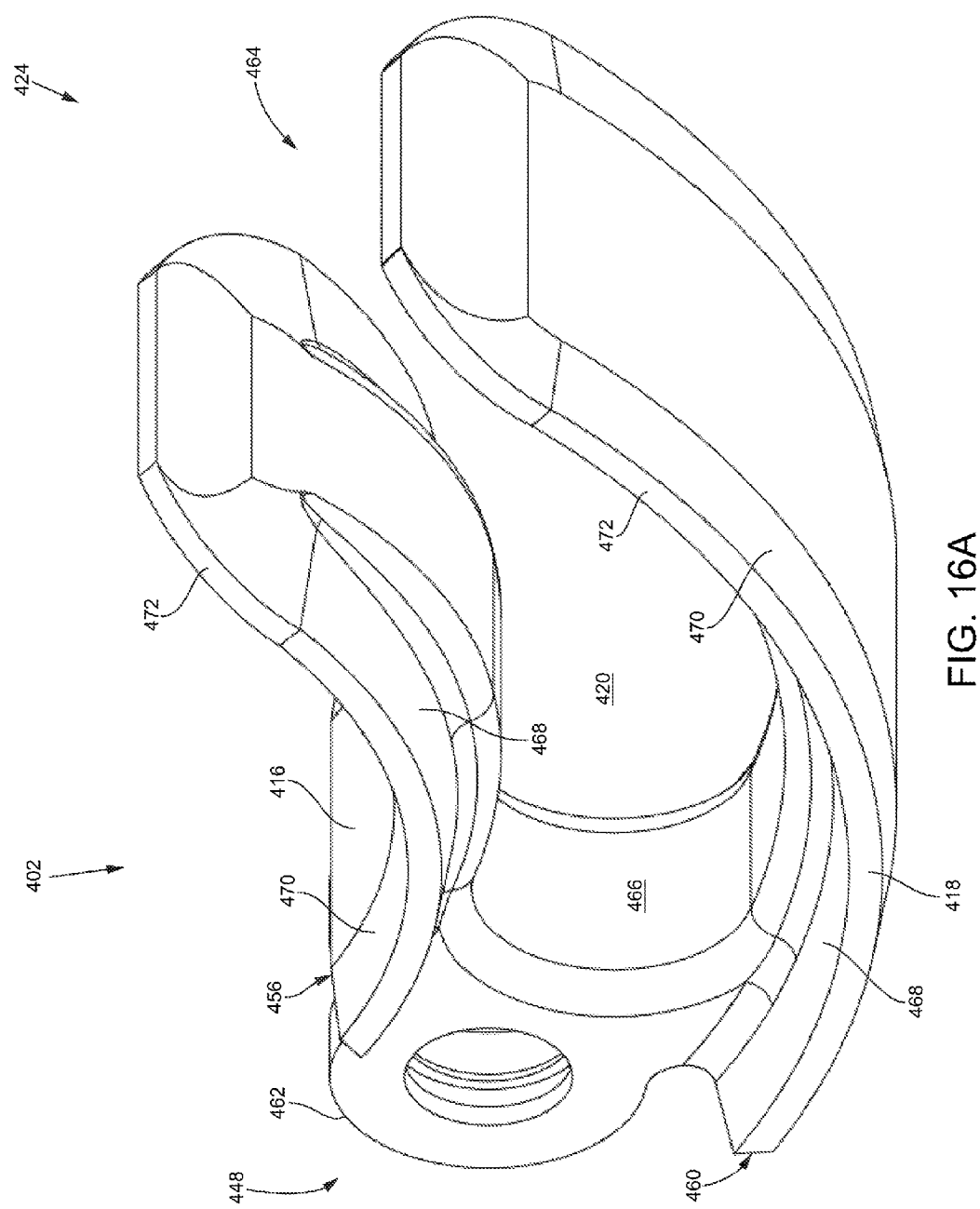

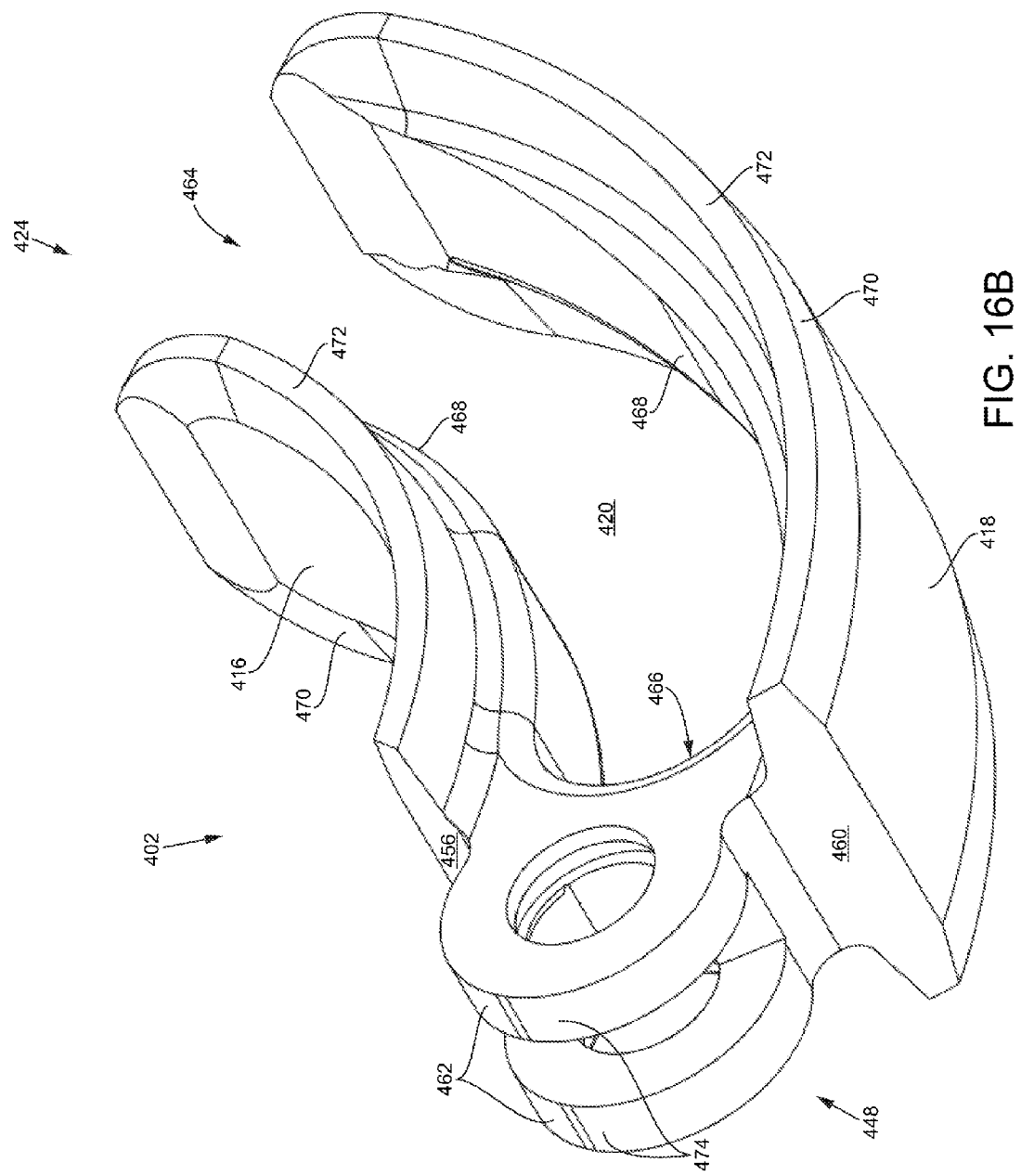

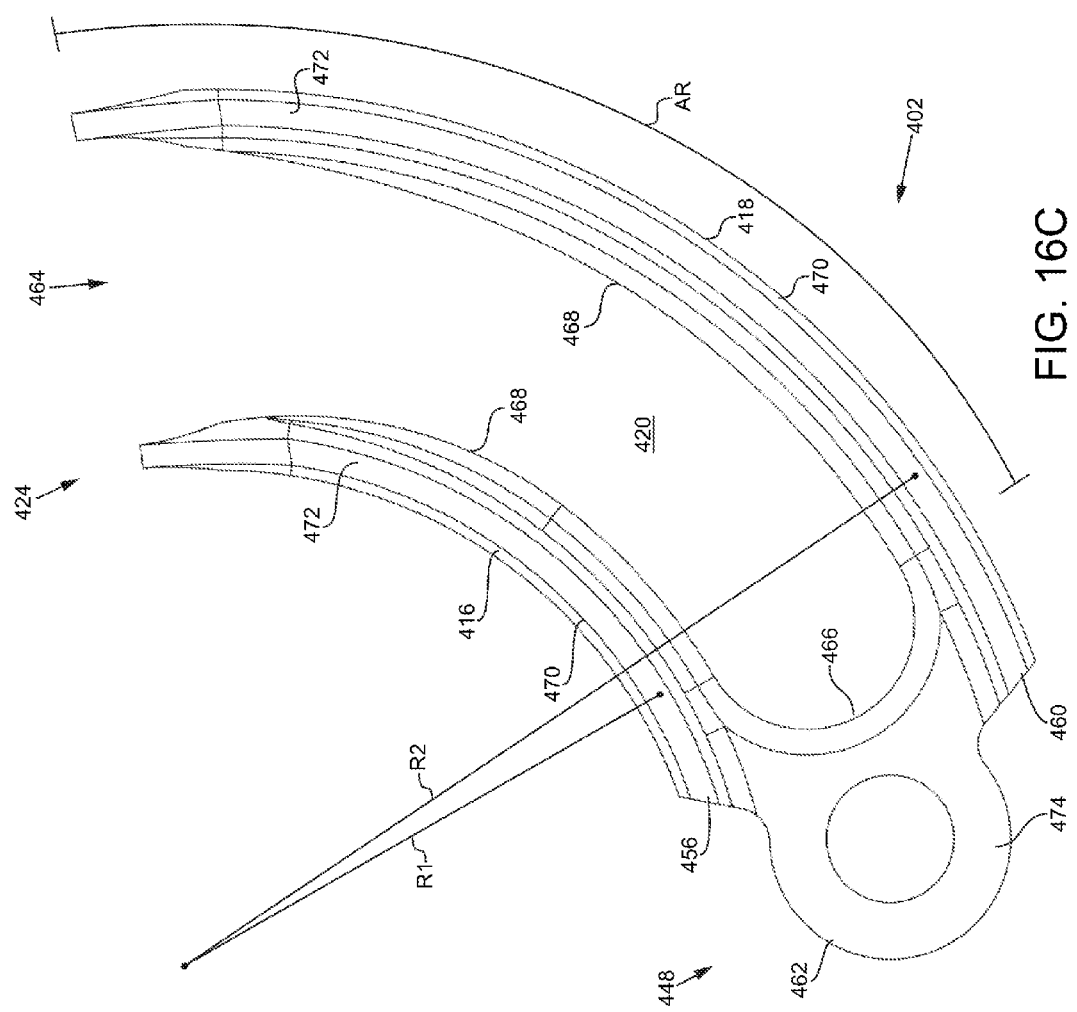

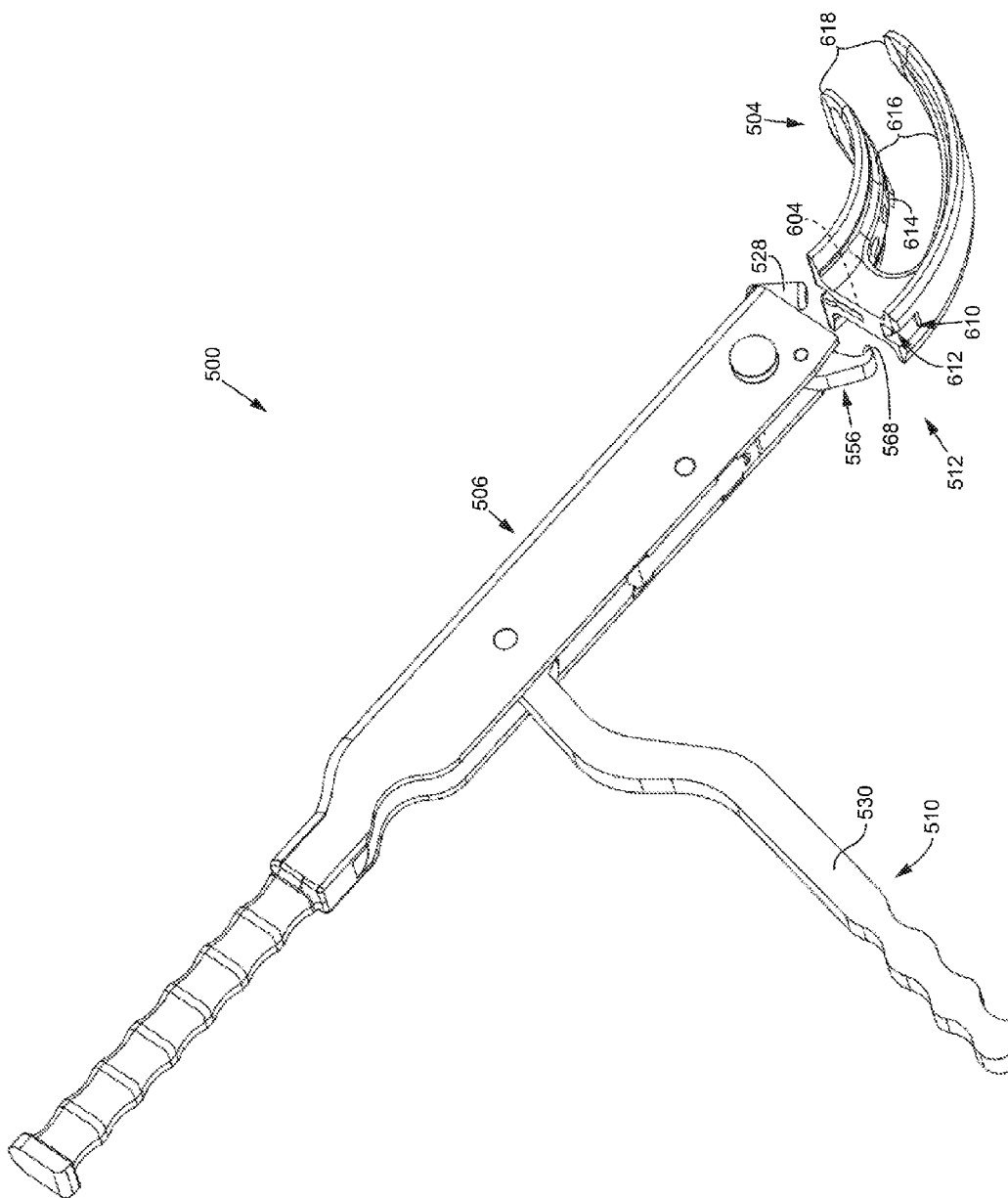

IMPLANTS, SYSTEMS, AND METHODS FOR FUSING A SACROILIAC JOINT

CROSS REFERENCE TO RELATED APPLICATIONS

The present application claims priority under 35 U.S.C. §119 to U.S. Provisional Patent Application 61/914,409, which was filed Dec. 11, 2013, entitled "SYSTEMS FOR AND METHODS OF FUSING A SACROILIAC JOINT," and is hereby incorporated by reference in its entirety into the present application.

The present application is also a continuation-in-part ("CIP") application of, and claims priority to, U.S. patent application Ser. No. 14/514,221 ("the '221 application"), which was filed Oct. 14, 2014, entitled "SYSTEMS FOR AND METHODS OF PREPARING A SACROILIAC JOINT FOR FUSION." The '221 application claims priority under 35 U.S.C. §119 to: 1) U.S. Provisional Patent Application 61/891,330, which was filed Oct. 15, 2013, entitled "SYSTEMS FOR AND METHODS OF FUSING A SACROILIAC JOINT"; 2) U.S. Provisional Patent Application 61/891,345, which was filed Oct. 15, 2013, entitled "SYSTEMS FOR AND METHODS OF FUSING A SACROILIAC JOINT"; 3) U.S. Provisional Patent Application 61/912,494, which was filed Dec. 5, 2013, entitled "SYSTEMS FOR AND METHODS OF FUSING A SACROILIAC JOINT"; 4) U.S. Provisional Patent Application 61/914,409, which was filed Dec. 11, 2013, entitled "SYSTEMS FOR AND METHODS OF FUSING A SACROILIAC JOINT"; and 5) U.S. Provisional Patent Application 61/954,594, which was filed Mar. 17, 2014, entitled "SYSTEMS AND METHODS FOR FUSING A SACROILIAC JOINT AND ANCHORING AN ORTHOPEDIC APPLIANCE". The '221 application and all Provisional Patent Applications to which it claims priority are hereby incorporated by reference in their entireties into the present application.

The present application is also a continuation-in-part ("CIP") application of, and claims priority to, U.S. patent application Ser. No. 14/447,612 ("the '612 application"), which was filed Jul. 31, 2014, entitled "SYSTEMS FOR AND METHODS OF FUSING A SACROILIAC JOINT." The '612 application claims priority under 35 U.S.C. §119 to: 1) U.S. Provisional Patent Application 61/979,857, which was filed Apr. 15, 2014, entitled "SACROILIAC JOINT IMPLANT"; 2) U.S. provisional application 61/955,126, which was filed Mar. 18, 2014, entitled "SACROILIAC JOINT IMPLANT"; 3) U.S. Provisional Patent Application 61/914,409, which was filed Dec. 11, 2013, entitled "SYSTEMS FOR AND METHODS OF FUSING A SACROILIAC JOINT"; and 4) U.S. Provisional Patent Application 61/860,185, which was filed Jul. 30, 2013, entitled "SYSTEMS FOR AND METHODS OF FUSING A SACROILIAC JOINT". The '612 application and all Provisional Patent Applications to which it claims priority are hereby incorporated by reference in their entireties into the present application.

TECHNICAL FIELD

Aspects of the present disclosure relate to medical apparatus and methods. More specifically, the present disclosure relates to devices, systems, and methods for fusing a sacroiliac joint.

BACKGROUND

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different conventional methods encompassing an anterior approach, a posterior approach, and a lateral approach with or without percutaneous screw or other type implant fixation. However, while each of these methods has been utilized for fixation and fusion of the sacroiliac joint over the past several decades, substantial problems with respect to the fixation and fusion of the sacroiliac joint remain unresolved.

A significant problem with certain conventional methods for fixation and fusion of the sacroiliac joint including the anterior approach, posterior approach, or lateral approach may be that the surgeon has to make a substantial incision in the skin and tissues for direct access to the sacroiliac joint involved. These invasive approaches allow the sacroiliac joint to be seen and touched directly by the surgeon. Often referred to as an "open surgery", these procedures have the attendant disadvantages of requiring general anesthesia and can involve increased operative time, hospitalization, pain, and recovery time due to the extensive soft tissue damage resulting from the open surgery.

A danger to open surgery using the anterior approach can be damage to the L5 nerve root, which lies approximately two centimeters medial to the sacroiliac joint or damage to the major blood vessels. Additionally and as seen in FIG. 1, which depicts a conventional fusion procedure (immobilization of the articular surfaces of the sacroiliac joint in relation to one another) on a sacroiliac joint 1, one or more screws or implants 2 are implanted transversely across the articular surfaces 3 and through the sacrum 4 and the ilium bones 5. That is, the joint 1 is immobilized by placement of a fusion device 2 transverse to or across a plane defined by articular surfaces 3 of the sacroiliac joint space.

Use of trans-sacroiliac and S1 pedicle-iliac bone implants can also involve the risk of damage to the lumbosacral neurovascular elements. Damage to the lumbosacral neurovascular elements as well as delayed union or non-union of the sacroiliac joint by use of these procedures may require revision surgery to remove all or a portion of the implants or repeat surgery as to these complications.

Another significant problem with conventional procedures utilizing minimally invasive small opening procedures can be that the procedures are technically difficult, requiring biplanar fluoroscopy of the articular surfaces of the sacroiliac joint and extensive surgical training and experience. Despite the level of surgical training and experience, there is a substantial incidence of damage to the lumbosacral neurovascular elements. Additionally, sacral anomalies can further lead to mal-placement of implants leading to damage of surrounding structures. Additionally, these procedures are often performed without fusion of the sacroiliac joint, which does not remove the degenerative joint surface and thereby may not address the degenerative condition of the sacroiliac joint, which may lead to continued or recurrent sacroiliac joint pain.

Another significant problem with conventional procedures can be the utilization of multiple trans-sacroiliac elongate implants, which do not include a threaded surface. This approach requires the creation of trans-sacroiliac bores in the pelvis and nearby sacral foramen, which can be of relatively large dimension and which are subsequently broached with instruments, which can result in bone being impacted into the pelvis and neuroforamen.

The creation of the trans-sacroiliac bores and subsequent broaching of the bores requires a guide pin, which may be inadvertently advanced into the pelvis or sacral foramen, resulting in damage to other structures. Additionally, producing the trans-sacroiliac bores, broaching, or placement of the elongate implants may result in damage to the lumbosacral neurovascular elements, as above discussed. Additionally, there may be no actual fusion of the articular portion of the sacroiliac joint, which may result in continued or recurrent pain requiring additional surgery.

Another substantial problem with conventional procedures can be that placement of posterior extra-articular distracting fusion implants and bone grafts may be inadequate with respect to removal of the articular surface or preparation of cortical bone, the implant structure and fixation of the sacroiliac joint. The conventional procedures may not remove sufficient amounts of the articular surfaces or cortical surfaces of the sacroiliac joint to relieve pain in the sacroiliac joint. The conventional implant structures may have insufficient or avoid engagement with the articular surfaces or cortical bone of the sacroiliac joint for adequate fixation or fusion. The failure to sufficiently stabilize and fuse the sacroiliac joint with the conventional implant structures and methods may result in a failure to relieve the condition of sacroiliac joint being treated. Additionally, conventional methods of driving apart a sacrum and ilium may lead to mal-alignment of the sacroiliac joint and increased pain.

Improvements to sacroiliac joint fusion involve systems and methods for non-transverse delivery of an implant into the sacroiliac joint are described in U.S. patent applications: Ser. No. 12/998,712, filed May 23, 2011 entitled SACROILIAC JOINT FIXATION FUSION SYSTEM; Ser. No. 13/236,411, filed Sep. 19, 2011 entitled SYSTEMS FOR AND METHODS OF FUSING A SACROILIAC JOINT; and Ser. No. 13/475,695, filed May 18, 2012, entitled SYSTEMS FOR AND METHODS OF FUSING A SACROILIAC JOINT; and Ser. No. 13/945,053, filed Jul. 18, 2013, entitled SYSTEMS FOR AND METHODS OF FUSING A SACROILIAC JOINT; and Ser. No. 13/946,790, filed Jul. 19, 2013, entitled SYSTEMS FOR AND METHODS OF FUSING A SACROILIAC JOINT; and Ser. No. 14/216,975, filed Mar. 17, 2014, entitled SYSTEMS AND METHODS FOR FUSING A SACROILIAC JOINT AND ANCHORING AN ORTHOPEDIC APPLIANCE; and Ser. No. 14/447,612, filed Jul. 31, 2014, entitled SYSTEMS FOR AND METHODS OF FUSING A SACROILIAC JOINT. All of application Ser. Nos. 12/998,712, 13/236,411, 13/475,695, 13/945,053, 13/946,790, 14/216,975, and 14/447,612 are herein incorporated by reference in their entirety.

The systems and methods discussed herein address the challenges in fusing the sacroiliac joint.

SUMMARY

One implementation of the present disclosure may take the form of a sacroiliac joint fusion system. In certain embodiments, the system may include a joint implant, an anchor element and a delivery tool.

In certain embodiments, the joint implant may include a proximal end, a distal end, a longitudinal axis extending between the proximal and distal ends of the joint implant, and a graft window extending non-parallel to the longitudinal axis. The anchor element may include a proximal end and a distal end. The anchor element may be configured to be received in the graft window of the joint implant.

In certain embodiments, the delivery tool may include an implant arm, an anchor arm, and a positioning arm. In certain embodiments, the implant arm may include an implant shaft extending between a proximal end and a distal end of the implant arm, and a longitudinal axis extending between the proximal and distal ends of the implant arm. The distal end of the implant arm may be configured to releasably couple to the proximal end of the joint implant. In certain embodiments, the anchor arm may include an anchor shaft extending between a proximal end and a distal end of the anchor arm, and a longitudinal axis extending between the proximal and distal ends of the anchor arm. The distal end of the anchor arm may be configured to releasably couple to the proximal end of the anchor element.

In certain embodiments, the positioning arm may be coupled with the implant arm at a first end and coupled with the anchor arm at a second end. The implant arm may be configured to rotate relative to the first end along the longitudinal axis of the implant arm within a fixed range of rotation. When the implant arm is coupled to the first end and the anchor arm is coupled to the second end, a delivery arrangement may automatically exist such that the anchor element and the joint implant align in a trajectory such that the anchor element will be received within the graft window upon convergence of the anchor element and the joint implant.

In certain implementations, the anchor element may be configured to be received within the graft window of the joint implant in any rotational orientation of the implant arm that is within the fixed range of rotation.

In certain implementations, the fixed range of rotation may be about 60 degrees of rotation.

In certain implementations, the fixed range of rotation may be about 45 degrees of rotation.

In certain implementations, the fixed range of rotation may be between about 45 degrees and about 60 degrees of rotation.

In certain implementations, the graft window may extend to the distal end of the joint implant and define an opened distal end. In this and other implementations, the joint implant may further include a pair of generally parallel keels extending from the proximal end to the distal end, and a spanning member extending between the pair of generally parallel keels at the proximal end of the joint implant. The graft window may extend between the spanning member and the pair of generally parallel keels.

In certain implementations, the implant shaft may be longitudinally and slideably displaceable relative to the first end of the positioning arm.

In certain implementations, the implant shaft may be laterally and slideably displaceable relative to the first end of the positioning arm, wherein lateral displacement is transverse to the longitudinal axis of the implant arm.

In certain implementations, the first end may include a channel defined in the positioning arm and the implant arm may include a cam feature that interacts with the channel when the implant arm is coupled to the first end. In this and other implementations, a cross-sectional shape of the implant shaft defines the cam feature. In this and other implementations, the cam feature may be configured to rotate within the channel between a pair of locked positions that define the fixed range of rotation.

In certain implementations, the anchor arm may include an anchor retainer extending through a passageway of the anchor shaft, a distal end of the anchor retainer configured to releasably couple to the proximal end of the anchor element. In this and other implementations, a proximal end of the anchor retainer may include a first head that is configured to be rotationally engaged so as to releasably couple the distal end of the anchor retainer with the proximal end of the anchor element.

In certain implementations, the implant arm includes an implant retainer extending through a passageway of the implant shaft, a distal end of the implant retainer configured to releasably couple to the proximal end of the joint implant. In this and other implementations, a proximal end of the implant retainer includes a second head that is configured to be rotationally engaged so as to releasably couple the distal end of the implant retainer with the proximal end of the joint implant.

In certain implementations, the implant arm includes the cam mechanism and the positioning arm includes a channel, wherein the cam mechanism includes a cam-shape that is configured to only partially rotate within the channel to define the fixed range of rotation.

In certain implementations, longitudinal displacement of the implant arm relative to the first end is fixed beyond a certain point so as to inhibit contact between a surface of the joint implant and the anchor element. In this and other implementations, the positioning arm includes an opening at the first end that is configured to receive the implant shaft therethrough, the implant arm comprising a stop feature that is configured to contact the positioning arm during longitudinal displacement and inhibit further displacement.

Another implementation of the present disclosure may take the form of a method for fusing a sacroiliac joint having a sacrum and an ilium. In certain embodiments, the method may include providing a joint implant and a delivery tool.

In certain embodiments, the joint implant may include a body and a graft window. The body may extend between an implant proximal end and an implant distal end. The graft window may extend non-parallel through the body and extend proximally from the implant distal end to define at least a portion of an opened distal end.

In certain embodiments, the delivery tool may include an implant arm, an anchor arm, and a positioning arm. The implant arm may extend between a proximal implant arm end and a distal implant arm end. The distal implant arm end may be configured to releasably couple to the implant proximal end of the joint implant. The anchor arm may extend between a proximal anchor arm end and a distal anchor arm end. The distal anchor arm end may be configured to releasably couple to a proximal end of an anchor element.

In certain embodiments, the positioning arm may couple the implant arm and the anchor arm such that, when coupled, a delivery arrangement automatically exists such that the anchor element and the joint implant align in a trajectory such that the anchor element will be received within the graft window upon convergence of the anchor element and the joint implant. The implant arm may be configured to rotate relative to the positioning arm about a longitudinal axis of the implant arm within a fixed range of rotation.

In certain embodiments the method may further include releasably coupling the implant proximal end to the distal implant arm end and releasably coupling the proximal end of the anchor to the distal anchor arm end.

In certain embodiments, the method may further include, first, delivering the anchor element transversely through the sacroiliac joint and, second, delivering the joint implant non-transversely into the sacroiliac joint such that the anchor element is positioned within the graft window of the joint implant. The joint implant may be in an orientation within the sacroiliac joint such that the body and the graft window are a generally within a plane defined by the sacroiliac joint.

In certain embodiments, the method may further include uncoupling the distal implant arm end from the implant proximal end and uncoupling the distal anchor arm end from the proximal end of the anchor element.

In certain implementations, the method may include rotating the implant arm about the longitudinal axis and within the fixed range of rotation to select a final implant trajectory that will result in delivery of the joint implant into the sacroiliac joint in the orientation.

In certain implementations, the fixed range of rotation may be about 60 degrees of rotation.

In certain implementations, the fixed range of rotation may be between about 20 degrees and about 90 degrees.

In certain implementations, the body of the joint implant may further include a first keel, a second keel opposite the first keel, and a spanning member coupling and extending between the first and second keels at the implant proximal end. The graft window may be defined between the first and second keels and the spanning member. In this and other implementations, the body of the joint implant may further include a pair of wing members coupled with the spanning member and extending generally perpendicularly from a surface of the spanning member that extends between the first and second keels. In this and other implementations, the surface of the spanning member may be a planar surface.

In certain implementations, the step of uncoupling the distal implant arm end from the implant proximal end may entail rotationally engaging a proximal portion of an implant retainer. The implant retainer may extend through a passageway that extends through the implant arm and define the distal implant arm end that releasably couples with the implant proximal end.

In certain implementations, the step of uncoupling the distal anchor arm end from the proximal end of the anchor element entails rotationally engaging a proximal portion of an anchor retainer, the anchor retainer extending through a passageway that extends through the anchor arm and defining the distal anchor arm end that releasably couples with the proximal end of the anchor element.

In certain implementations, the implant arm may include a cam mechanism and the positioning arm includes a channel. The cam mechanism may include a cam-shape that is configured to only partially rotate within the channel to define the fixed range of rotation.

In certain implementations, a distal-most depth of delivery of the joint implant may be fixed so as to inhibit contact between a surface of the joint implant and the anchor element.

In certain implementations, a proximal portion of the implant arm includes a stop feature that is configured to contact the positioning arm when the distal-most depth is reached.

In certain implementations, an implant may be inserted into the sacroiliac joint region along a generally arcuate path. Accordingly, a surgical preparation technique and tools may be utilized while operating in the arcuate path. The implant arcuate path may follow and generally match the surgical preparation arcuate path and a path arc may include a radius of between approximately 3 cm to 6 cm. The portion of the path having an arcuate path including a radius of between approximately 3 cm to 6 cm may reside substantially in the plane of the sacroiliac joint or in a plane in close proximity and generally parallel thereto. Furthermore, the arcuate path may generally or substantially reside in a sacroiliac joint articular region. Additionally, an implant may be selected for use during the procedure which substantially matches the radius or curvature of the arcuate or curved insertion path or surgical preparation path.

In certain implementations, a curved implant may include: 1) a proximal end region configured to couple with an inserter; 2) a first distally extending member coupled to the implant proximal region; 3) a second distally extending member coupled to the implant proximal region and spaced apart from the first distally extending member, and 4) a gap between the first and second distally extending members at a distal end region such that the first and second distally extending members are connected to one another only at the proximal end region; wherein the proximal end region further includes a first and second bone contact surface generally opposed to one another and where said contact surfaces extend distally from a proximal end region contact surface extreme proximal first and second edge, respectively, toward an implant distal end; and wherein a superior end of the proximal end region defines a coupling location of the first distally extending member, and the superior end extends between the contact surfaces; and where an inferior end of the proximal end region defines a coupling location of the second distally extending member, and the inferior end extends between the contact surfaces; and wherein each the first and second distally extending members comprise a first and second longitudinally extending axis, respectively, and the first and second longitudinal axes curve along a length of the implant such that the first and second curved axes are concentrically aligned.

Furthermore, the first and second distally extending members may further include a first and second maximum thickness and a first and second maximum width, respectively, the first maximum thickness defined between a point on a superior most surface and an inferior most surface of a lateral end region of the first distally extending member; the second maximum thickness defined between a point on a superior most surface and an inferior most surface of a lateral end region of the second distally extending member; the first maximum width defined between a first extreme lateral edge of a first lateral edge region of the first distally extending member and a second extreme lateral edge of a second lateral edge region of the first distally extending member; the second maximum width defined between a first extreme lateral edge of a first lateral edge region of the second distally extending member and a second extreme lateral edge of a second lateral edge region of the second distally extending member, wherein the first and second lateral edge regions of both the first and second distally extending members extend lateral beyond the first and second contact surfaces, respectively; and wherein the first maximum thickness is greater than the second maximum thickness and the first maximum width is greater than the second maximum width and wherein the extreme lateral edges of the first distally extending member extend a greater distance from the first and second contact surfaces versus the distance between the extreme lateral edges of the second distally extending members and the first and second contact surfaces. Additionally, at a distal end region of the first distally extending member, the superior and/or inferior surfaces may taper toward one another. Said taper may be configured in different manners; e.g., the distal end region of the superior surface may have a curvature which is concentrically aligned with the first axis while the inferior surface may taper toward an extreme distal edge of the superior surface such that when implanted the first distally extending member may transition from a neutral condition to an expanded condition; the neutral condition is such that the first axis is substantially concentrically aligned with a central curved longitudinal axis of the implant; and the expanded condition is such that the distal end region of the first distally extending member is displaced further from the central axis versus the neutral condition. Alternatively, the taper may be configured where both the superior and inferior surfaces taper toward one another such that the first distally extending member remains in a generally neutral condition when advanced into the joint. Said curved implant may be positioned into the sacroiliac joint such that a point of concentricity (as defined by the first and second curved axes) is generally posterior and/or dorsal the implant body after final implant placement such that the second distally extending member is in proximity to a sacroiliac joint ventral boundary (a combination of the inferior boundary segment, anterior-inferior corner and anterior boundary segment).

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIGS. 12A-12H are steps in the methodology and illustrated in the same transverse cross-section taken along a plane extending medial-lateral and anterior-posterior.

FIG. 14A is an isometric top view of a positioning arm.

FIG. 16A is a front isometric view of another embodiment of an implant.

FIG. 16B is a back isometric view of the implant of FIG. 16A.

FIG. 16C is a side view of the implant of FIG. 16A.

FIG. 18K is an isometric side view of the delivery tool and implant in an uncoupled state with the lever handle in an opened position.

DETAILED DESCRIPTION

I. Delivery Tool for Fusion of the Sacroiliac Joint

Implementations of the present disclosure involve a delivery tool for fusing a sacroiliac joint involving an implant delivered within a plane of the joint and an anchor delivered transversely (i.e., across) the joint. The delivery tool is configured to deliver the anchor prior or subsequent to delivery of the implant. The delivery tool, in particular, may include an anchor arm coupled to an implant arm via a positioning arm. The positioning arm is removeably, rotationally, and slideably coupled with both the anchor arm and the implant arm. The positioning arm includes a rotating joint at the connection with the implant arm such that the implant arm may rotate within a "window" of orientations that are configured to allow an anchor at a distal end of the anchor arm to be positioned within a graft window or opening of an implant at a distal end of the implant arm. The rotational "window" of orientations may be mechanically fixed at the rotating joint such that rotational movement of the implant arm is restrained to orientations within the "window." Such a configuration of a delivery tool with a range of allowable orientations of the implant arm relative to the anchor arm allows for blind delivery of an implant or anchor (i.e., depending on the order of delivery) that ensures positioning of the anchor within the graft window of the implant.

Figure 1:
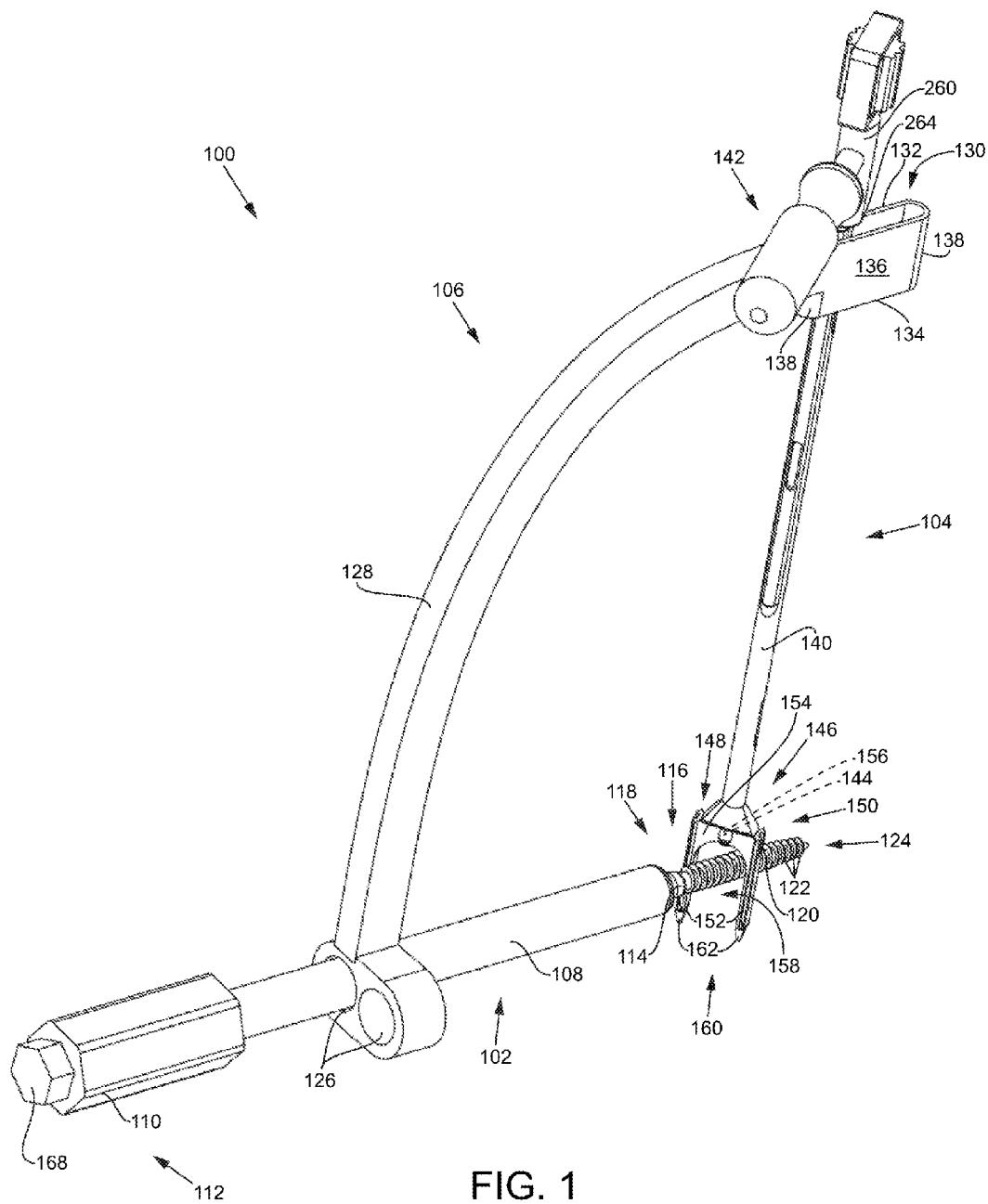
FIG. 1 is a top isometric view of a delivery system with an anchor arm, an implant arm, and a positioning arm coupled therebetween.

To begin, reference is made to FIG. 1, which depicts a delivery tool 100 in an isometric view. As seen in the figure, the delivery tool 100 includes an anchor arm 102, an implant arm 104, and a positioning arm 106 coupled between the anchor arm 102 and implant arm 104. The anchor arm 102 may include an anchor shaft 108 with a handle 110 at a proximal end 112 and an anchor retainer 114 at a distal end 116. The anchor retainer 114 may releasably couple with a proximal end 118 of an anchor element 120. The anchor retainer 114 may include a shaft (as seen in FIG. 3B) that extends through an internal passageway in the anchor shaft 108. The anchor retainer 114 may include a head 168 at the proximal end 112 of the anchor arm 102. The head 168 may be rotationally engaged by a user to releasably couple the anchor retainer 114 and the anchor element 120. The anchor element 120 may be a bone screw or anchor or similar device configured to be delivered through a patient's bone (e.g., sacrum, ilium). The anchor element 120 may have a threading 122 on its outer surface and may include a tapered distal end 124.

Referring to the positioning arm 106, it includes a pair of collars 126 that are each configured to receive the anchor shaft 108 and orient the anchor shaft 108 such that it may rotate and translate; however, angling of the anchor arm 102 relative to the positioning arm 106 is restrained. Angling is restrained because the collars include a diameter that is slightly larger than an outer diameter of the anchor shaft 108.

Extending away from and coupled to the pair of collars 126 is an arcuate positioning member 128. As seen in FIG. 1, the positioning member 128 is positioned directly above one of the collars 126 while the other one of the collars 126 is offset from the positioning member 128. A channel 130 is formed in the positioning member 128 on an end opposite the pair of collars 126. The channel 130 defines a stadium-shaped opening that extends from a proximal edge 132 to a distal edge 134 of the channel 130. The channel 130 is bounded by generally perpendicular side walls 136 and rounded end walls 138 that are positioned between the side walls 136. The channel 130 is configured to receive the implant arm 104 and restrain its rotation to a limited, pre-determined range. As will be discussed later, the channel 130 and the implant arm 104 form a rotating joint about which the implant arm 104 may be rotated relative to positioning arm 106 and the anchor arm 102, or vice versa.

While the positioning member 128 is depicted as being arcuate, other designs are possible and contemplated herein. The positioning member 128 may, for example, be a single straight member or may include multiple members of differing shapes. As another example, the positioning member 128 may include telescoping members that enable retraction and extension of an inner telescoping member.

As seen in FIG. 1, when the anchor arm 102 is positioned in the particular collar 126 that lies in a common plane with the positioning member 128, the anchor element 120 is configured to be positioned in a central portion of a graft window 158 of an implant 150. That is, one of the collars 126 lies in a common plane with the positioning member 128, the channel 130, and, thus, the shaft 140 of the implant arm 104. The other collar 126 is offset such that, when the anchor arm 102 is positioned in the other collar 126, the anchor element 120 will be positioned outside the graft window 158 of the implant 150 (e.g., caudal or cranial of the implant 150).

Figure 2:
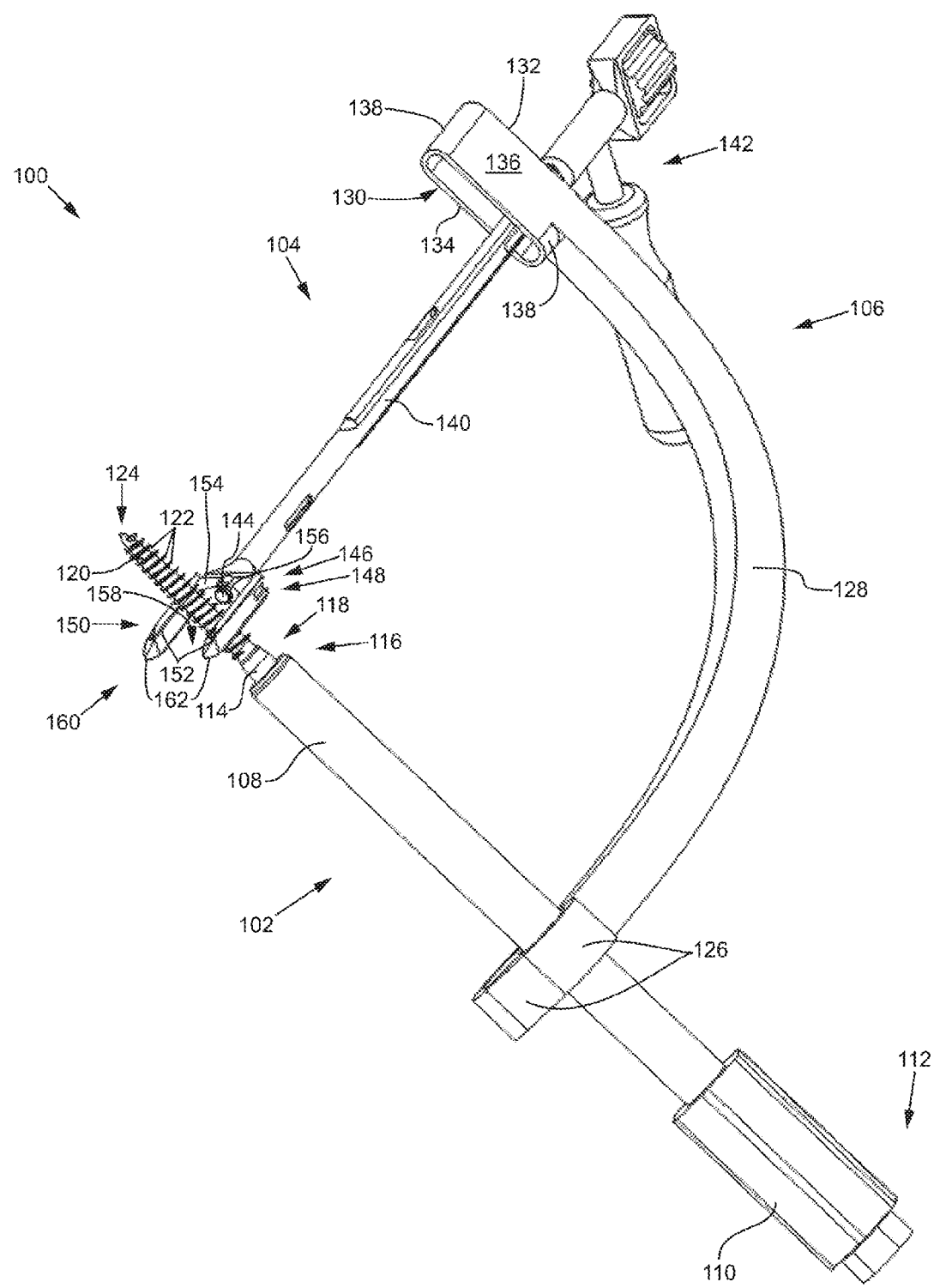
FIG. 2 is a bottom isometric view of the delivery system of FIG. 1.

Still referring to FIG. 1, the implant arm 104 includes an implant shaft 140 extending between a handle assembly 142 and an implant retainer 144 at a distal end 146 of the implant arm 104. The implant retainer 144 is configured to releasably couple with a proximal end 148 of an implant 150. In this embodiment, the implant 150 is fork-shaped and includes a pair of keels 152 extending distally from a proximally positioned spanning member 154 that couples with and extends between the pair of keels 152. Turning to FIG. 2, which is bottom isometric view of the delivery tool 100, the spanning member 154 includes a bore 156 to receive the implant retainer 144. In this embodiment, the bore 156 and the implant retainer 144 include complementary threading; however, other mechanisms are possible to releasably couple the implant 150 and the implant retainer 144. Referring back to the implant 150, a distal opening or graft window 158 is defined between the pair of keels 152. The graft window 158 is open at a distal end 160 of the implant 150. Thus, the distal end 160 of the implant 150 is defined by distal tips 162 of the keels 152 and the graft window 158 extending between the distal tips 162.

As illustrated in FIGS. 1-2, the implant arm 104 is limited to certain rotational arrangements such that the anchor element 120 will remain positioned within the graft window 158. Conversely, the anchor arm 102 and positioning arm 106 are limited to certain rotational arrangements relative to the implant arm 104 such that the anchor element 120 will remain positioned within the graft window 158. That is, either the implant arm 104 may be rotated or the anchor arm 102 and positioning arm 106 may be rotated; this will depend on whether the implant 150 or the anchor element 120 is delivered into a patient's body first (i.e., in a fixed position). In this way, for example, a surgeon may choose to initially deliver the anchor element 120 into the patient's body. Subsequently, the surgeon may choose to deliver the implant 150. Prior to delivery of the implant 150, the surgeon may rotate the implant arm 104 relative to the positioning arm 106 and anchor arm 102 until a trajectory is chosen to deliver the implant 150 into the joint space. The surgeon is able to rotate the implant arm 104 relative to the positioning arm 106 and the anchor arm 102 because they are in a fixed position (i.e., anchored to the patient's bone) relative to the implant arm 104. Thus, any rotational position of the implant arm 104 chosen by the surgeon will ensure that, when delivered into the joint space, the anchor 150 will be positioned within the graft window 158 of the implant 150.

Alternatively, for example, a surgeon may choose to initially deliver the implant 150 into the surgical area. Subsequently, the surgeon may choose to deliver the anchor element 120. Prior to delivery of the anchor element 120, the surgeon may rotate the anchor arm 102 and the positioning arm 106 relative to the implant arm 104 until a trajectory is chosen to deliver the anchor element 120 transversely across the joint space. The surgeon is able to rotate the anchor arm 102 and positioning arm 106 as an assemblage relative to the implant arm 104 because the implant arm is in a fixed position (i.e., implanted in the patient's joint) relative to the anchor arm 102 and positioning arm 106. Thus, any rotational position chosen by the surgeon will ensure that, when delivered transversely across the joint space, the anchor 150 will be positioned within the graft window 158 of the implant 150.

Figure 3A:
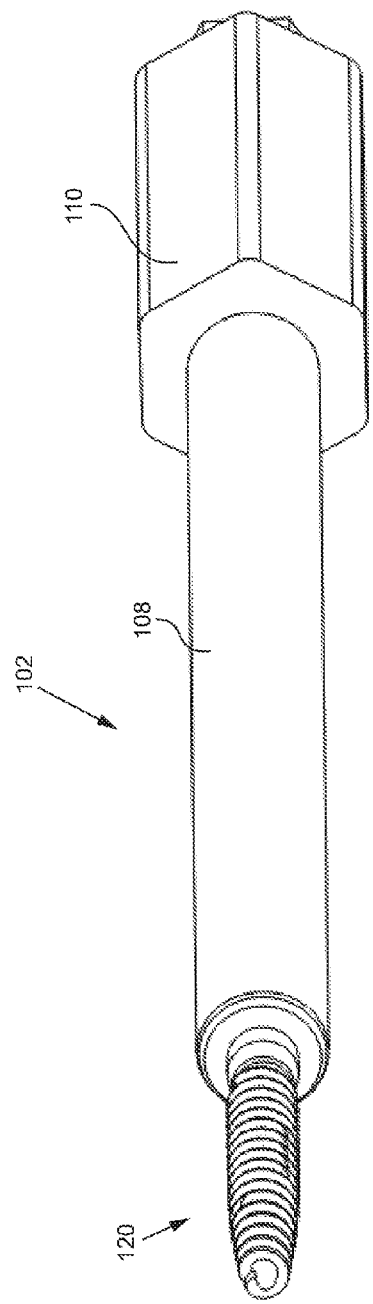
FIG. 3A is a side isometric view of the anchor arm coupled with an anchor.
Figure 3B:
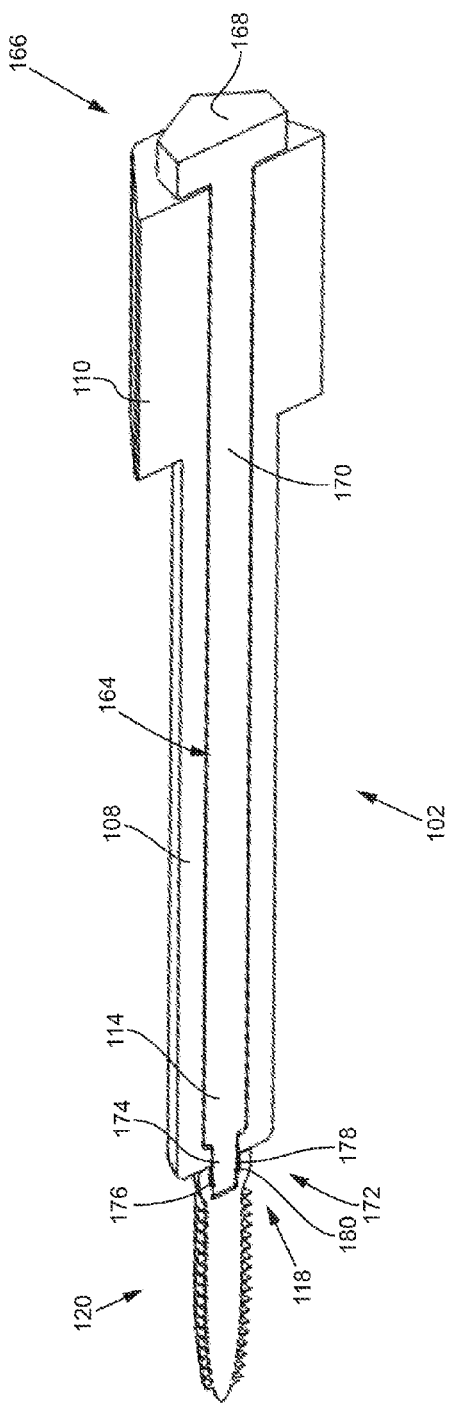
FIG. 3B is a cross-sectional side isometric view of the anchor arm coupled with the anchor.

Reference is now made to FIG. 3A, which is an isometric side view of the anchor arm 102 coupled to the anchor element 120. As seen in the figure, the anchor shaft 108 is a tubular member that couples to the handle 110 at the proximal end 112 of the anchor arm 102. The handle 110 includes a hexagonal cross-section, although other cross-sectional shapes are possible. As illustrated in FIG. 3B, which is a longitudinal cross-section view of the anchor arm 102 and the anchor element 120, the anchor retainer 114 is a cylindrical member (similar to a bolt) that extends through and is slidingly received within an internal passageway 164 of the shaft 108 of the anchor arm 102. A proximal end 166 of the implant retainer 114 includes the head 168 that may be shaped to fit a surgical tool configured to rotate the implant retainer 114. In this embodiment, the head 168 is a hexagonal bolt-type head. The head 168, however, may be differently shaped. Referring still to FIG. 3B, the head 168 distally transitions to a smooth shank 170. At a distal end 172 of the implant retainer 114 is a reduced diameter section 174 that includes a threaded section 176. The reduced diameter section 174 is configured to protrude through a distal opening 178 in the shaft 108 of the anchor arm 102. The distal opening 178 is sized to permit the reduced diameter section 174 from extending therethrough, but not the shank 170, which has a diameter that is larger than the reduced diameter section 174.

As seen in FIG. 3B, the threaded section 176 is a male-end that is configured to threadably engage with a female-end 180 at the proximal end 118 of the anchor element 120. In operation, the implant retainer 114 may be slidingly engaged and received within the internal passageway 164 in the anchor arm 102. The implant retainer 114 may be distally advanced such that the reduced diameter section 174 extends through the distal opening 178 in the shaft 108 of the anchor arm 102. At this point, the proximal end 118 of the anchor element 120 may be threadably engaged with the threaded section 176 by rotating the implant retainer 114 relative to the anchor element 120. When the anchor element 120 is fully, threadably engaged with the implant retainer 114, the proximal end 118 of the anchor element 120 abuts the distal end 116 of the anchor arm 116.

Referring back to FIGS. 1-2, once the anchor element 120 is fully secured to the anchor arm 102 via the implant retainer 114, the assemblage may be positioned within one of the collars 126 of the positioning arm 106. Or, if the anchor element 120 is to be delivered into the patient's body prior to the implant 150, the anchor arm 102 may be utilized by itself. In either situation, the anchor arm 102 may be distally advanced and rotationally driven into the patient's bone by rotating the assemblage of the anchor arm 102 coupled with the anchor until the anchor element 120 is sufficiently positioned within the patient's bone. At that point, the implant retainer 114 may be rotationally disengaged with the anchor element 120 and the anchor arm 102 may be removed from contact with the anchor element 120, which is left in place in the patient's bone. Alternatively, the anchor arm 102 may remain coupled with the anchor element 120 such that the positioning arm 106 and the implant arm 104 may be coupled with the anchor arm 102 for the subsequent delivery of the implant 150 into the joint space.

Figure 4:
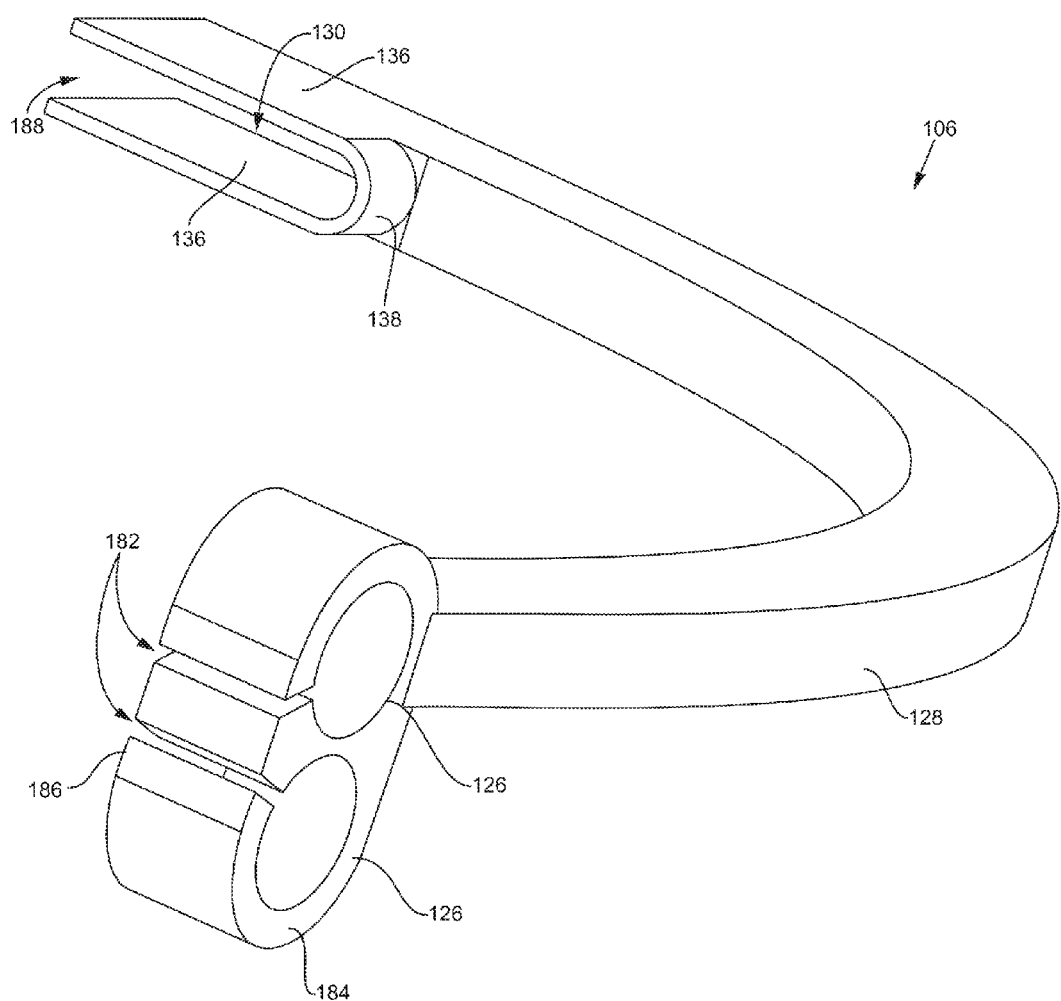
FIG. 4 is an isometric view of the positioning arm.

Reference is now made to FIG. 4, which depicts an isometric view of the positioning arm 106. In this embodiment of the positioning arm 106, the collars 126 include an expansion slit 182 extending from a proximal edge 184 to a distal edge 186. In this way, the collars 126 may expand and provide a friction or interference fit against the anchor shaft 108 of the anchor arm 102 when it is received within the collars 126. Also in this embodiment of the positioning arm 106, the channel 130 is formed by the generally parallel side walls 136 and a single end wall 138. That is, a distal end 188 of the channel 130 is open. In other embodiments (e.g., FIGS. 1-2), the distal end 188 of the channel 130 is closed and bounded by another end wall 138.

Figure 5A:
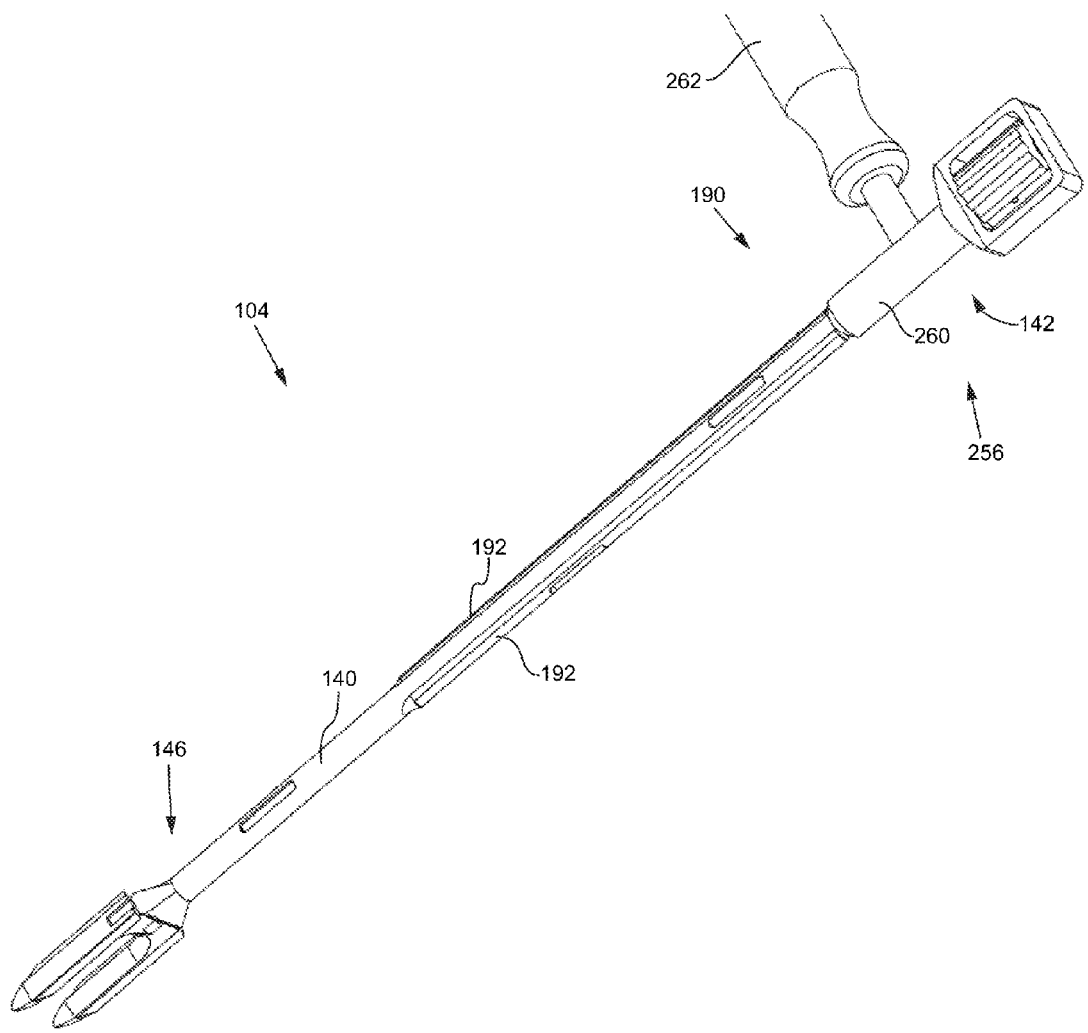
FIG. 5A is an isometric side view of the implant arm and handle assembly.

Turning now to the implant arm 104, reference is made to FIG. 5A, which depicts an isometric side view of the implant arm 104 and handle assembly 142. At the proximal end 190 of the implant arm 104, the implant shaft 140 includes a pair of members 192 that extend from a surface of the implant shaft 140. As will be seen in FIGS. 6-7, the pair of members 192 define a cam-shaped cross-section that is received within the channel 130 (not shown) of the positioning arm 106 (not shown). Distal of the pair of members 192, the implant shaft 140 defines a circular cross-section. The proximal end 190 of the implant arm 104 is configured to be releasably secured to the handle assembly 142. Alternatively, the handle assembly 142 may be fixedly secured to the implant arm 104.

Figure 5B:
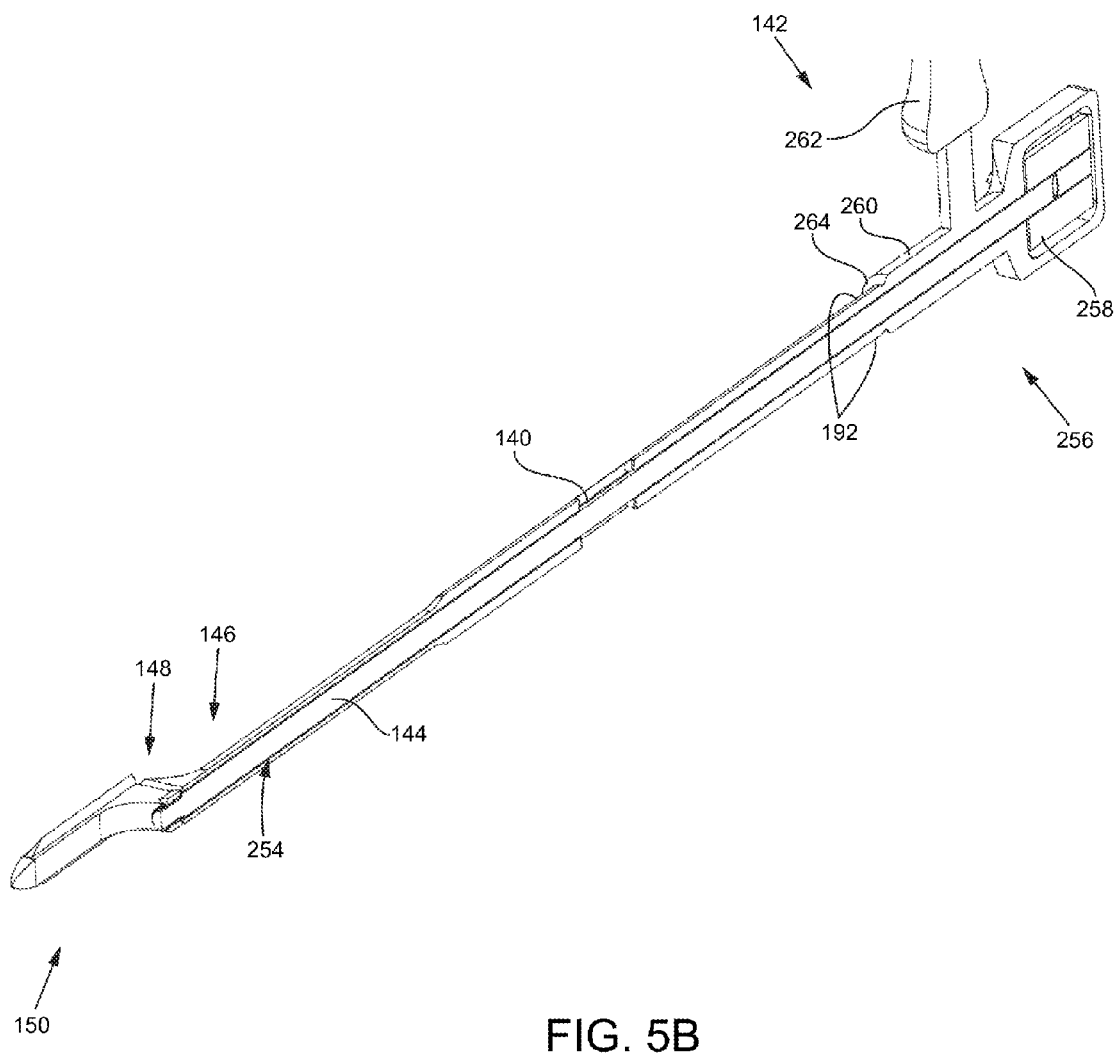
FIG. 5B is a cross-sectional view of the implant arm and the handle assembly.

As seen in FIG. 5B, which is a cross-sectional view of the implant arm 104 and the handle assembly 142, the implant retainer 144 extends through a passageway 254 that extends though the implant shaft 140 from a proximal end 256 to the distal end 146 of the implant arm 104. At the distal end 146 of the implant arm 104, the implant retainer 144 threadably couples to the proximal end 148 of the implant 150. At the proximal end 256 of the implant arm 104, the implant retainer 144 couples with a rotationally engageable head 258 that is configured to be rotated in order to couple and decouple the implant retainer 144 and the implant 150. As seen in FIGS. 5A-5B, the handle assembly 142 includes an enlarged body 260 at the proximal end 256 of the implant arm 104. The handle assembly 142 also includes a handle 262 extending generally perpendicularly off of the enlarged body 260 that is configured to be grasped by a surgeon during a surgical procedure.

The enlarged body 260 at the proximal end 256 of the implant arm 104 includes an increased diameter compared with the implant shaft 140 and the pair of members 192. The enlarged body 260 is sized such that it will not extend through the channel 130 of the positioning arm 106 as the implant arm 104 is distally advanced, as seen in FIG. 1, which ensures that the implant 150 will remain in a predefined orientation relative to the anchor element 120. In operation, the implant 150 may be distally advanced until a distal end 264 of the enlarged body 260 contacts the proximal edge 132 of the channel 130. In this orientation, the anchor element 120 will be positioned within the graft window 158 of the implant 150.

Figure 6:
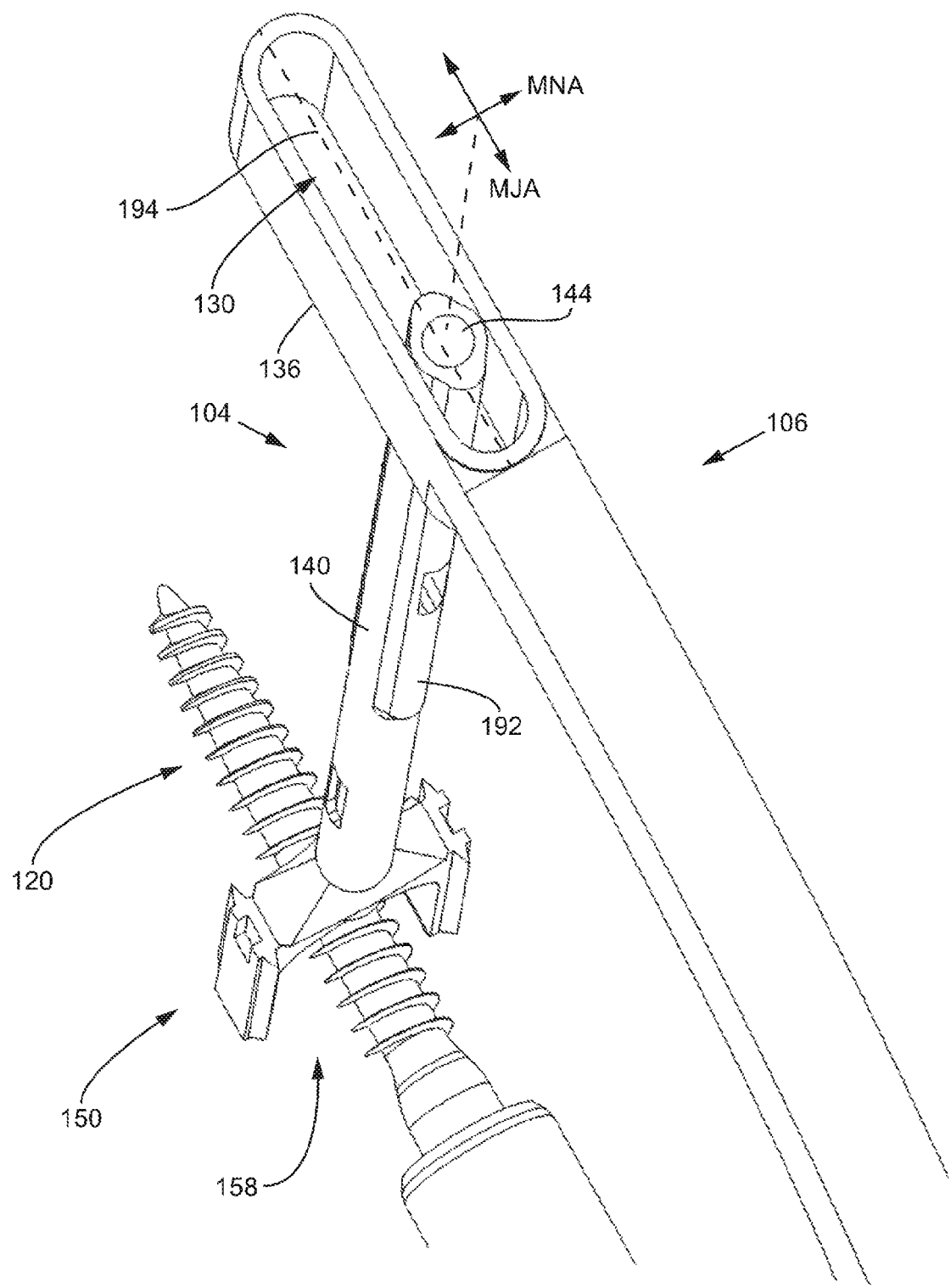
FIG. 6 is an isometric, cross-sectional view of a channel and a proximal end of the implant arm.

As seen in FIG. 6, which is an isometric, cross-sectional view of the channel 130 and the proximal end 190 of the implant arm 104, the portion of the implant shaft 140 having the pair of members 192 and the implant retainer 144 are configured to be received within the channel 130 of the positioning arm 106 to form a rotating joint. In this figure, the cross-section is taken along the channel 130 and perpendicular to the extension of the implant arm 104. As seen in the figure, the pair of members 192 define a cam-shape that is semi-elliptic or similar to a rhombus or lozenge with rounded corners. Other cam-shapes are possible such as, for example, an egg-shaped or elliptic shape. As illustrated in this figure, the implant shaft 140 is positioned within the channel 130 such that a minor axis MNA of the cam-shaped cross-section of the implant shaft 140 generally extends across the channel 130 and in between the parallel side walls 136. And, the major axis MJA of the cam-shaped cross-section of the implant shaft 140 generally extends along a longitudinal axis 194 of the channel 130. In this way, the implant shaft 140 is configured to rotate within a range of degrees relative to the channel 130 (and, thus, the implant is configured to rotate within the same range relative to the anchor element 120) where the range of degrees is fixed by the size and orientation of the cam-shaped cross-section of the pair of members 192 on the implant shaft 140.

In certain embodiments, the implant shaft 140 may rotate with a range of about 70 degrees. In certain embodiments, the range of degrees may be 40, 50, or 60, among others. Such a range may depend on a size or orientation of an anchor element 120 or implant 150. That is, a particular implant 150 may have a relatively small graft window 158 such that a corresponding implant arm 104 must be used with an implant shaft 140 having a smaller range of rotation. Conversely, a particular implant 150 having a relatively larger graft window 158 may allow for an implant arm 104 having an implant shaft 140 that allows for a larger range of rotation.

Figure 7:
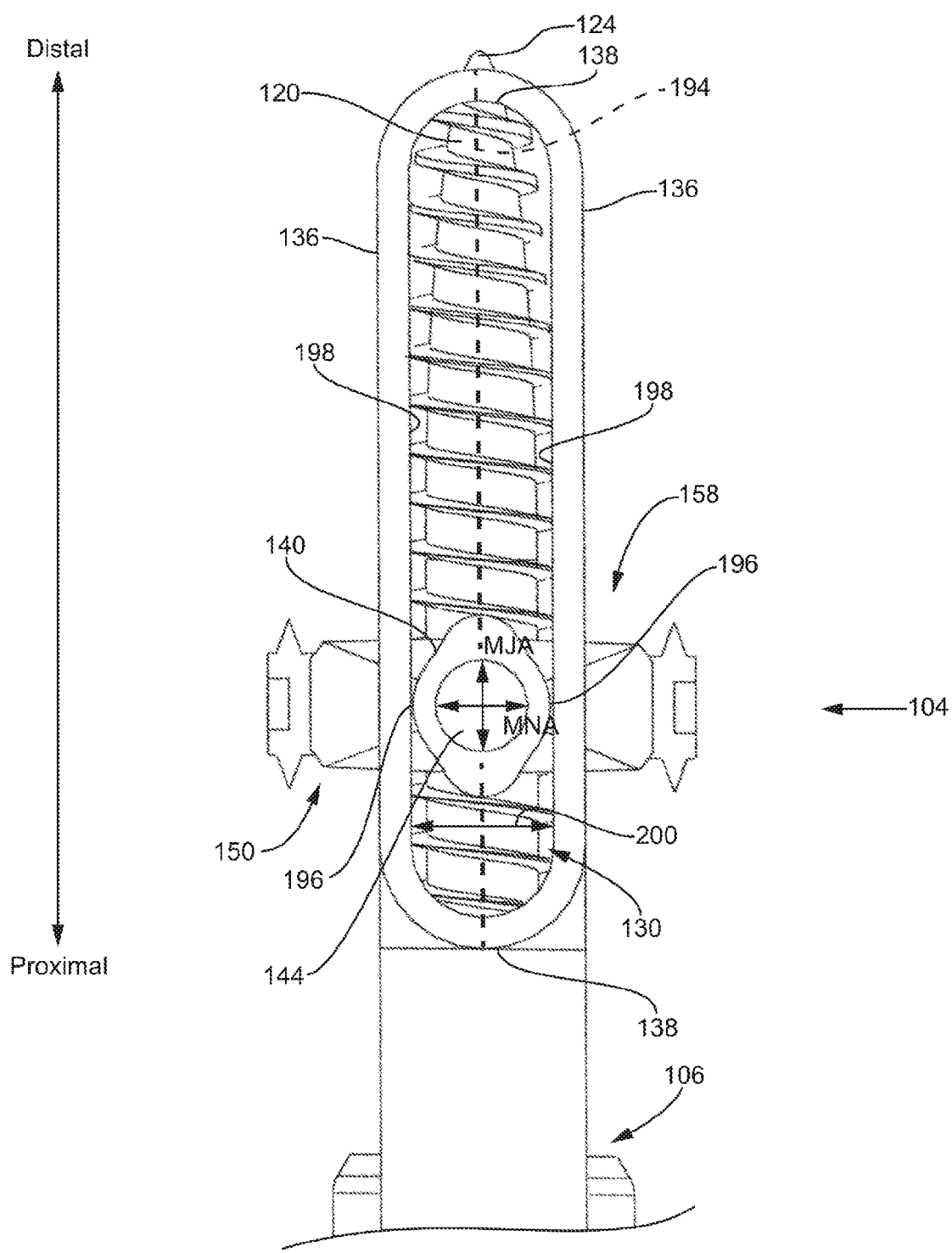
FIG. 7 is a top view of the cross-sectional illustration of FIG. 6 depicting the implant arm in a particular rotational orientation.

Reference is now made to FIG. 7, which is a close-up, top view of the cross-sectional illustration of FIG. 6. As seen in the figure, the implant shaft 140 is neutrally positioned within the channel 130 of the positioning arm 106. That is, the major axis MJA is generally parallel with a longitudinal axis 194 of the channel 130 and with the side walls 136. In the neutral position, outer surfaces 196 on the implant shaft 140 that are on the minor axis MNA abut inner walls 198 of the channel 130. Between these outer surfaces 196 define a diameter that is similar to a length 200 defined between the inner walls 198 of the channel 130. As seen in the figure, the implant shaft 140 may rotate clockwise or counterclockwise within the range of degrees determined by the geometric orientation of the cam-shaped cross-section of the implant shaft 140. Within the range of degrees, the implant shaft 140 is configured to rotate the implant 150 relative to the anchor element 120 such that the anchor element 120 will remain positioned within the graft window 158 of the implant 150.

Figure 8:
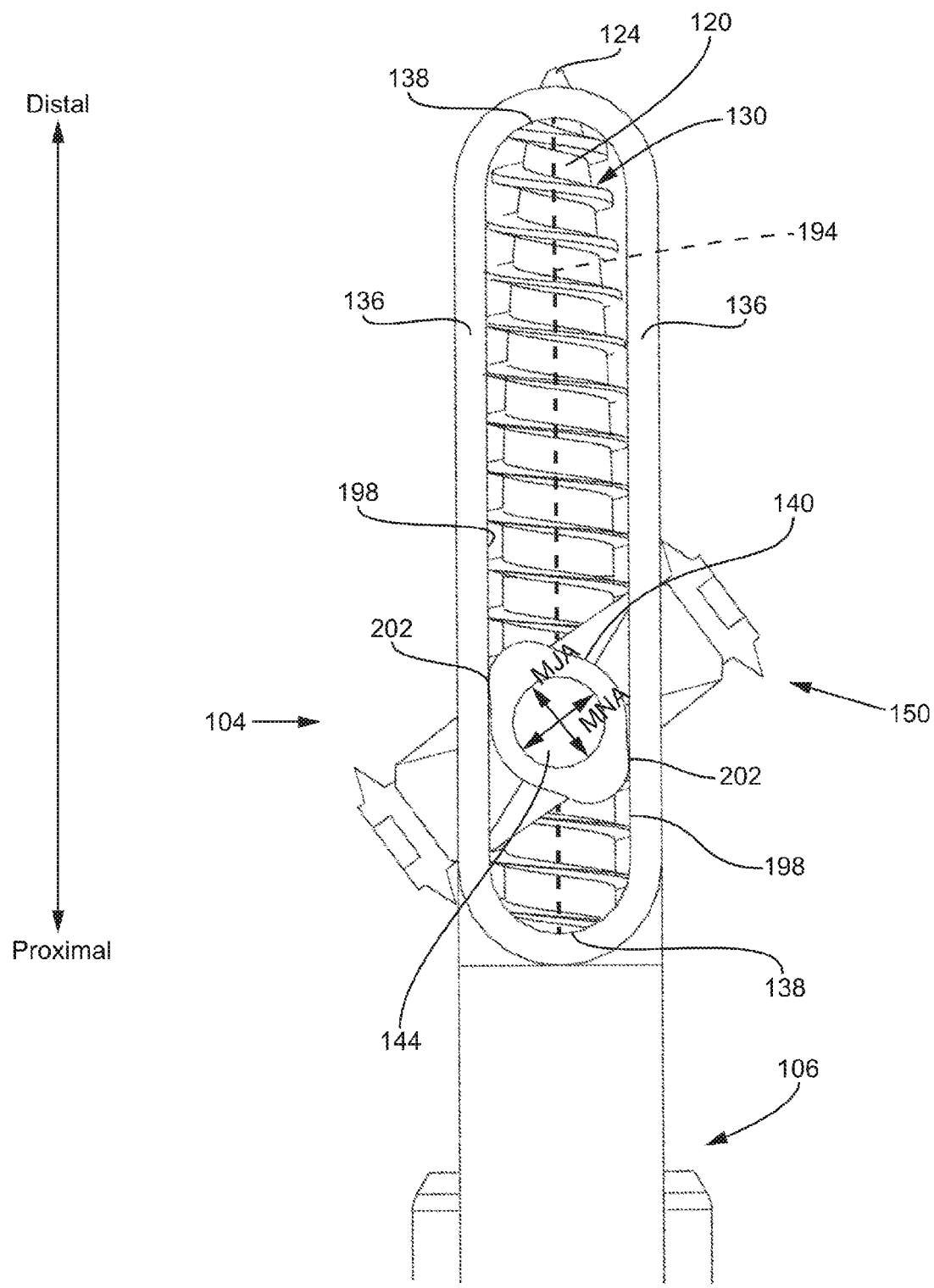
FIG. 8 is another top view of the cross-sectional illustration of FIG. 6 depicting the implant arm in another particular rotational orientation.

Turning to FIG. 8, which is another close-up, top view of the cross-sectional illustration of FIG. 6, the implant shaft 140 is in a locked position within the channel 130. That is, the implant shaft 140, in FIG. 8, has been rotated counterclockwise from the neutral position (as shown in FIG. 7) such that the geometric configuration of the cam-shaped cross-section of the implant shaft 140 is locked or prevented from further rotation within the channel 130. In this position, camming surfaces 202 of the implant shaft 140 contact opposing inner walls 198 of the channel 130 and are prevented from further counterclockwise rotation by the force exerted on the camming surfaces 202 by the inner walls 198. Further rotation is restricted because the diameter of the implant shaft 140 increases and causes the camming surfaces 202 to contact the inner walls 198 of the channel 130. While FIG. 8 only shows the implant shaft 140 in a counterclockwise rotation, the implant shaft 140 will similarly lock in a clockwise rotation by camming surfaces 202 contacting the inner walls 198 of the channel. Generally, the range of degrees of allowable rotation of the implant shaft 140 relative to the channel 130 will be equally split between clockwise and counterclockwise rotation on either side of the neutral position; however, the implant shaft 140 may be shaped such that rotation is unequally split between clockwise and counterclockwise rotation.

As seen in FIGS. 7-8, the implant shaft 140 may be positioned within the channel 130 at any point along the longitudinal axis 194 of the channel 130. That is, the implant arm 104 or, more particularly, the implant shaft 140 may translate distal-proximal within the channel 130. Thus, as the implant shaft 140 is distally translated, the implant 150 is positioned closer to the tapered distal end 124 of the anchor element 120. And, as the implant shaft 140 is proximally translated, the implant 150 is positioned closer to the proximal end 118 of the anchor element 120. In addition, the implant shaft 140 may extend through the channel 130 at an angle such that the implant shaft 140 is not parallel to the end walls 138 of the channel 130. In other words, the implant shaft 140 may extend at angles other than perpendicular relative to the anchor arm (not shown in FIGS. 7-8). Alternatively, the implant shaft 140 may be restrained from such angling relative to the anchor arm.

Figure 9:
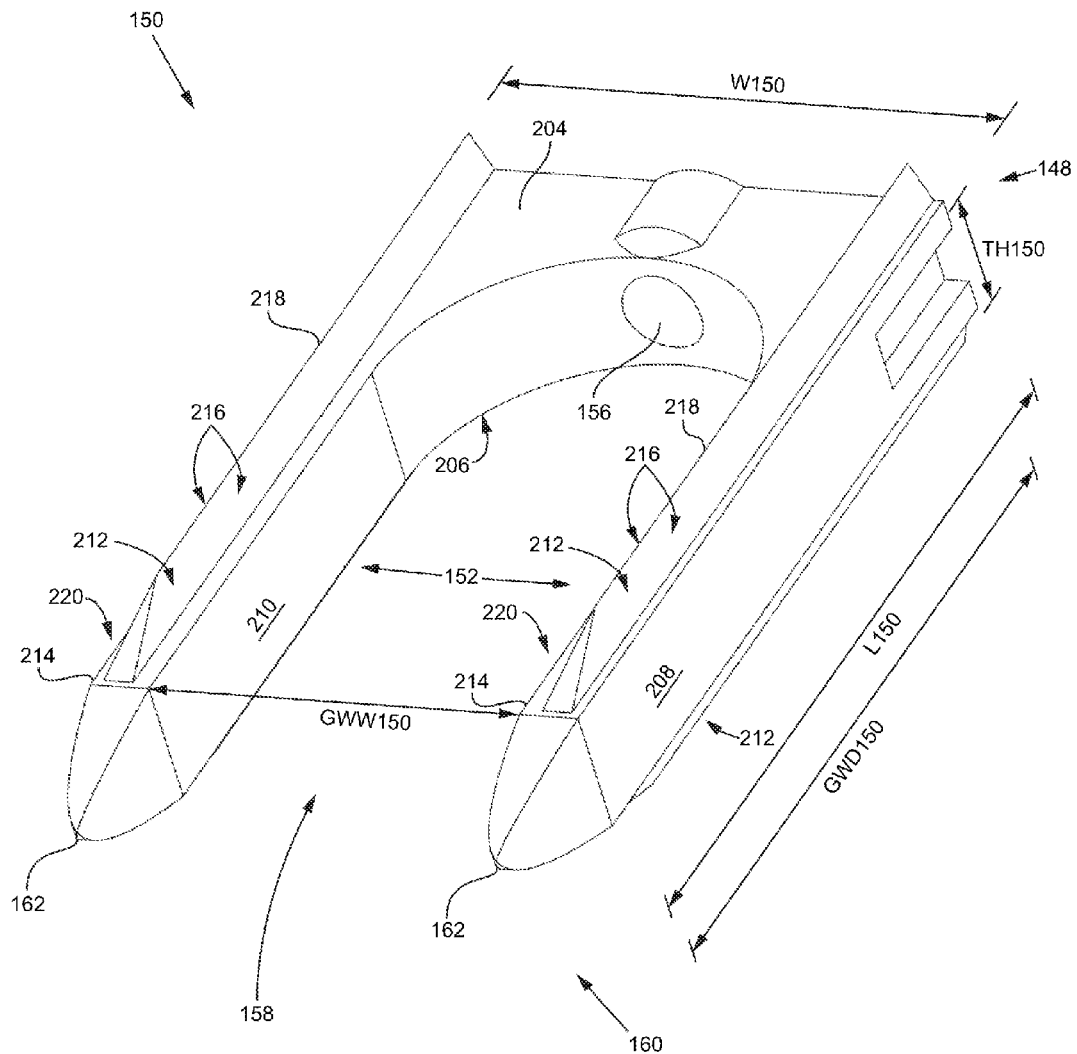
FIG. 9 is an isometric view of the implant.

Moving on, reference is made to FIG. 9, which is an isometric view of the implant 150. As seen in the figure, the implant 150 includes a pair of keels 152 extending distally from the proximal end 148 of the implant 150. Extending between the keels 152 at the proximal end 148 is the spanning member 154 that includes the bore 156 for receiving the implant retainer 144 (not shown in FIG. 9). And, extending between the keels 152 at the distal end 160 and extending proximally to the spanning member 154 is the graft window 158. The pair of keels 152 include distal tips 162 that converge to a point.

The implant 150 further includes a top surface 204 and a bottom surface 206 generally opposite the top surface 204. The top and bottom surfaces 204, 206 extend onto each of the keels 152. The top and bottom surfaces 204, 206 are also generally perpendicular to outer surfaces 208 and inner surfaces 210 of the keels 152. On the top and bottom surfaces 204, 206 of each of the keels 152 is a fin 212 that extend from the proximal end 148 of the implant 150 to a distal end 214 of the keels 152 where the keels 152 begin tapering towards the distal tip 162. The fins 212 extend outward from the top and bottom surfaces 204, 206 and include opposite side surfaces 216 that converge at a blade-like edge 218 that extends from a length of the fin 212. The distal end 220 end of the fin 212 is beveled. While the blade-like edge 218 is shown with a straight-edge, the edge may include serrations, grooves, or other features.

In certain embodiments, the implant 150 may have the following dimensions. A length L150 of the implant 150 may be within a range of about 25 mm to about 60 mm. In certain embodiments, the length L150 may be about 30 mm, 40 mm, or 50 mm. A width W150 of the implant 150 may be within a range of about 15 mm to about 40 mm. In certain embodiments, the width W150 may be about 20 mm, 27.5 mm, or 35 mm. A thickness TH150 of the implant 150 defined between the top and bottom surfaces 204, 206 may be within a range of about 2.5 mm to about 10 mm. In certain embodiments, the thickness TH150 may be about 3 mm, 5 mm, or 7 mm. Furthermore, the thickness TH150 may vary between the distal and proximal end; e.g., the proximal end region may have a substantially smaller TH150, e.g., between 2 mm and 4 mm, versus a substantially larger TH150 at a proximal end region which may have a TH150 of approximately 5 mm to about 8 mm. A graft window width GWW150 of the implant 150 defined between the inner walls 210 of the keels 152 may be within a range of about 7 mm to about 30 mm. In certain embodiments, the graft window width GWW150 may be about 10 mm, 15 mm, or 20 mm. The graft window width GWW150 may extend about 20% to about 80% of the width W150 of the implant 150. In certain embodiments, the graft window width GWW150 may extend between about 30%, 50%, or 70% of the width W150 of the implant 150. A graft window depth GWD150 of the implant 150 defined between the opened distal end 160 of the implant 150 and a distal surface of the spanning member 154 may be within a range of about 22 mm to about 57 mm. In certain embodiments, the graft window depth GWD150 may be about 25 mm, 35 mm, or 45 mm. The graft window depth GWD150 may extend about 30% to about 90% of the length L150 of the implant 150. In certain embodiments, the graft window depth GWD150 may extend between about 50%, 65%, or 80% of the length L150 of the implant 150.

Figure 10:
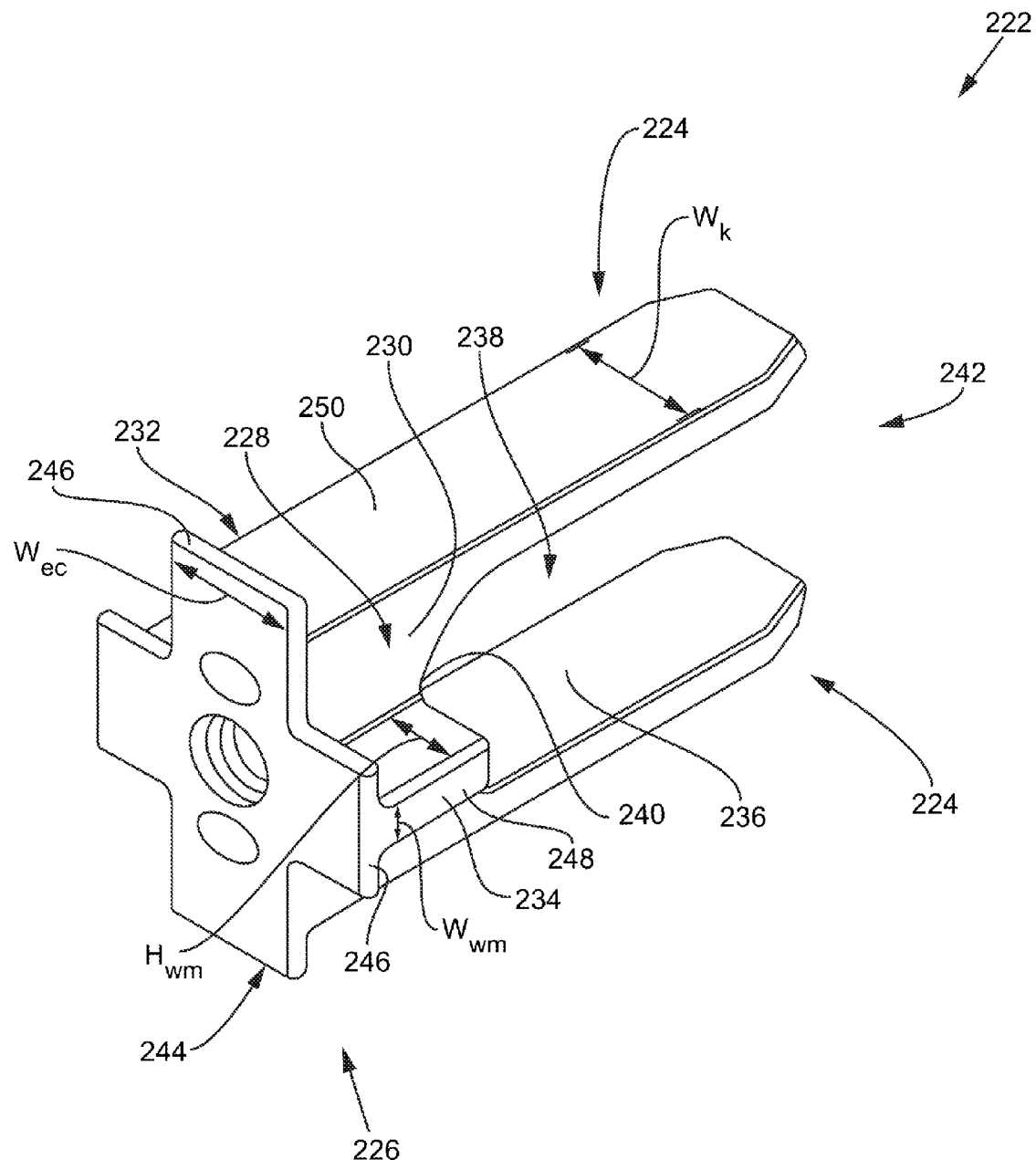
FIG. 10 is an isometric view of another implant.

Other implant designs for use with the delivery tool 100 are possible and contemplated by the present disclosure. For example, FIG. 10 depicts an isometric view of another embodiment of an implant 222. As seen in the figure, the implant 222 includes a pair of keels 224 extending distally from a proximal end 226 of the implant 222. A spanning member 228 extends between the keels 224 at the proximal end 226 of the implant 222. Extending between inner surfaces 236 of the keels 224 and the spanning member 228 is a graft window 238 that extends from a distal end 240 of the spanning member 228 to a distal end 242 of the implant 222. The graft window 238 is open at the distal end 242 such that the implant 222 may be delivered subsequently to delivery of an anchor (not shown) into a joint space where the anchor is positioned within the graft window 238.

Referring still to FIG. 10, the spanning member 228 further includes a top surface 230 and a bottom surface 232 generally opposite the top surface 230. Extending generally perpendicularly from the top and bottom surfaces 230, 232 of the spanning member 228 are wing members 234 that are centrally positioned between the keels 224. The wing members 234 extend from the proximal end 226 to the distal end 240 of the spanning member 228. The implant 222 may include an end cap 244 at the proximal end 226 of the implant 222. As seen in the figure, the end cap 244 is cross-shaped and plate-like and is coupled to the keels 224 and wing members 234. Extending through the end cap 244 and a portion of the spanning member 228 is a bore 252 that is configured to releasably couple with the implant retainer 144. An outer edge 246 of the end cap 244 lies flush with a top surface 248 of the wing members 234. And, the outer edge 246 also extends beyond a top surface 250 of the keels 224. A width $W_k$ of the keels 224 is about equal to a width $W_{ec}$ of the end cap 244. A width $W_{wm}$ of the wing members 234 is smaller than the width $W_{ed}$ of the end cap 244.

Example dimensions for the implant 222 may be the same or similar to those described in reference to the implant 150 of FIG. 9. Additional dimensions regarding the wing member 234 may be as follows. The wing members 234 may extend a height $H_{wm}$ of about 3 mm to about 15 mm from the top and bottom surfaces 230, 232 of the spanning member 228. In certain embodiments, the height $H_{wm}$ of the wing members 234 may extend about 5 mm, 8 mm, or 10 mm from the top and bottom surfaces 230, 232. The wing members 234 may include a width $W_{wm}$ of about 2 mm to about 7 mm. In certain embodiments, the width $W_{wm}$ may be about 2.5 mm, 3.5 mm, or 4.5 mm. The end cap 244 may include a width $W_{ec}$ of about 6 mm to about 15 mm. In certain embodiments, the width $W_{ec}$ of the end cap 244 may be about 7 mm, 9 mm, or 11 mm.

II. Methods of Fusing the Sacroiliac Joint with the Delivery Tool

The following discussion will focus on various methods of accessing and fusing a sacroiliac joint utilizing the tools and devices discussed previously. While the discussion focuses on fusing the sacroiliac joint, the methods discussed herein are not limiting; rather, the methods are applicable to the fusion of other joints as well.

A. Preoperative Planning for a Surgical Fusion Procedure

Prior to any joint preparation, a surgeon or other medical person may select a suitable procedure to fuse the sacroiliac joint. The procedure may include fusing the joint with or without delivering an implant in the joint space. If the surgeon selects a procedure involving delivery of an implant within the joint space, the surgeon will select an implant configuration for delivery into the sacroiliac joint of the patient based on preoperative or intraoperative data. The data may be the result of post-processing of raw or other imaging data (e.g. CT or MRI DICOM files). The post-processing may include the use of a software program (e.g., 3DSLICER available from http://www.slicer.org) that may be used for medical image processing and 3D visualization of image data. Other data may include the patient's weight, activity level, and general health.

The preoperative or intraoperative data may assist in the planning and selecting of desirable anchor trajectories (e.g., starting and stopping points on patient's soft tissue and near or within bone tissue), anchor dimensions (e.g., length, diameter, head size, washer, thread pitch), implant types and dimensions, and joint preparation tool types, dimensions, and configurations. A particularly system for preparing and fusing the sacroiliac joint may be selected, for example, for a hypermobile joint, which may include an implant or fusion system that is resistant to the expected forces present at that particular patient's sacroiliac joint. The determination of fixation sufficiency may be calculated based on the patient's data and also on the performance results of various bench and/or finite element analysis ("FEA") tested implant assembly configurations. For example, a calculated anchor and/or implant trajectory may be considered and determined from certain patient imaging and post-processing data with an overlayed implant assembly. Further, the implant assembly footprint within the joint plane may be selected as a lower percent of total joint surface to permit sufficient boney fusion across the joint while maintaining a sufficient implant sacral and iliac face surface area to prevent implant subsidence.

Specific measurements and characteristics of the patient's anatomy may influence the selection of a particular joint fusion system. For example, the patient's bone density may be measured at numerous locations in proximity to and surrounding the elements of the implant assembly. Lower bone density (e.g., osteopenia, osteoporosis) corresponding to a T-score lower than −1, sacroiliac joint instability, or hypermobility may require the use of an implant assembly with a greater amount of keel (i.e., the material cross section as defined by thickness of the keel and its length along implant longitudinal axis and also keels extending a greater distance into both bones defining the sacroiliac joint) and anchor extending across the sacroiliac joint and into the ilium and sacrum. Additionally, the relative angles between the implant longitudinal axis and anchor or anchors, and also the relative angles between multiple anchors (e.g., parallel, divergent, convergent) may be preselected based on the patient's anatomy.

A comparison of the preoperative or intraoperative data (e.g., sacroiliac joint surface area, joint surface contours, joint space volume (and related dimensions), joint boundaries, joint mobility, loading, bone density, desirable anatomic pathways) and the selected implant assembly and joint preparation tools may be conducted to ensure or validate compatibility before the manufacture ships the implant system and/or before the surgeon employs the system in a surgical procedure. After implant assembly and preparation tools validation, the selected assemblies may be shipped to the surgeon and the surgeon may proceed with the surgical fusion procedure utilizing the selected assemblies.

B. Anatomical Overview and Positioning of an Implant Non-Transversely within the Sacroiliac Joint To begin, reference is made to FIGS. 11A-11B, which depict various bone landmarks adjacent, and defining, the sacroiliac joint 1000 of a patient 1001.

Figure 11A:
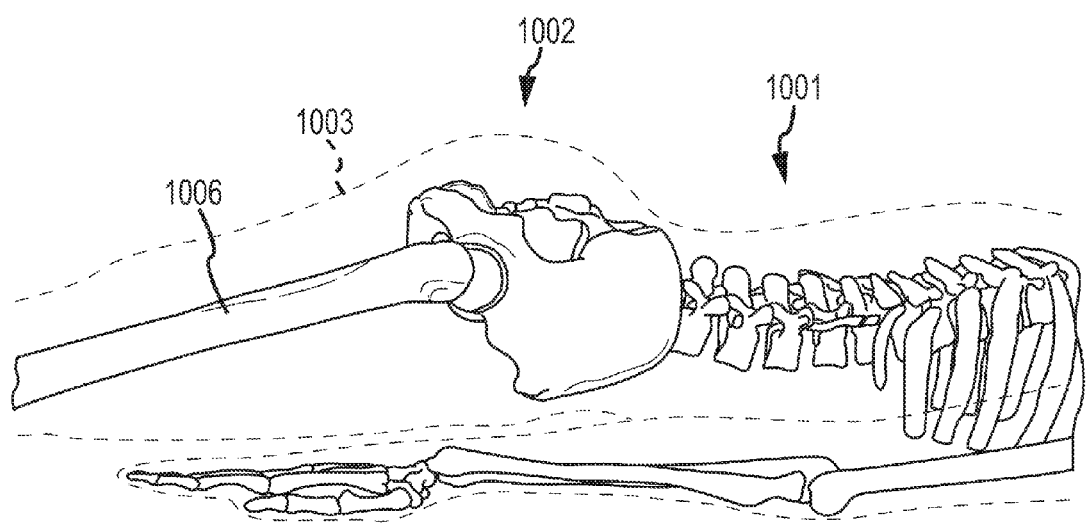
FIG. 11A is a right lateral view of a hip region of a patient lying prone.
Figure 11B:
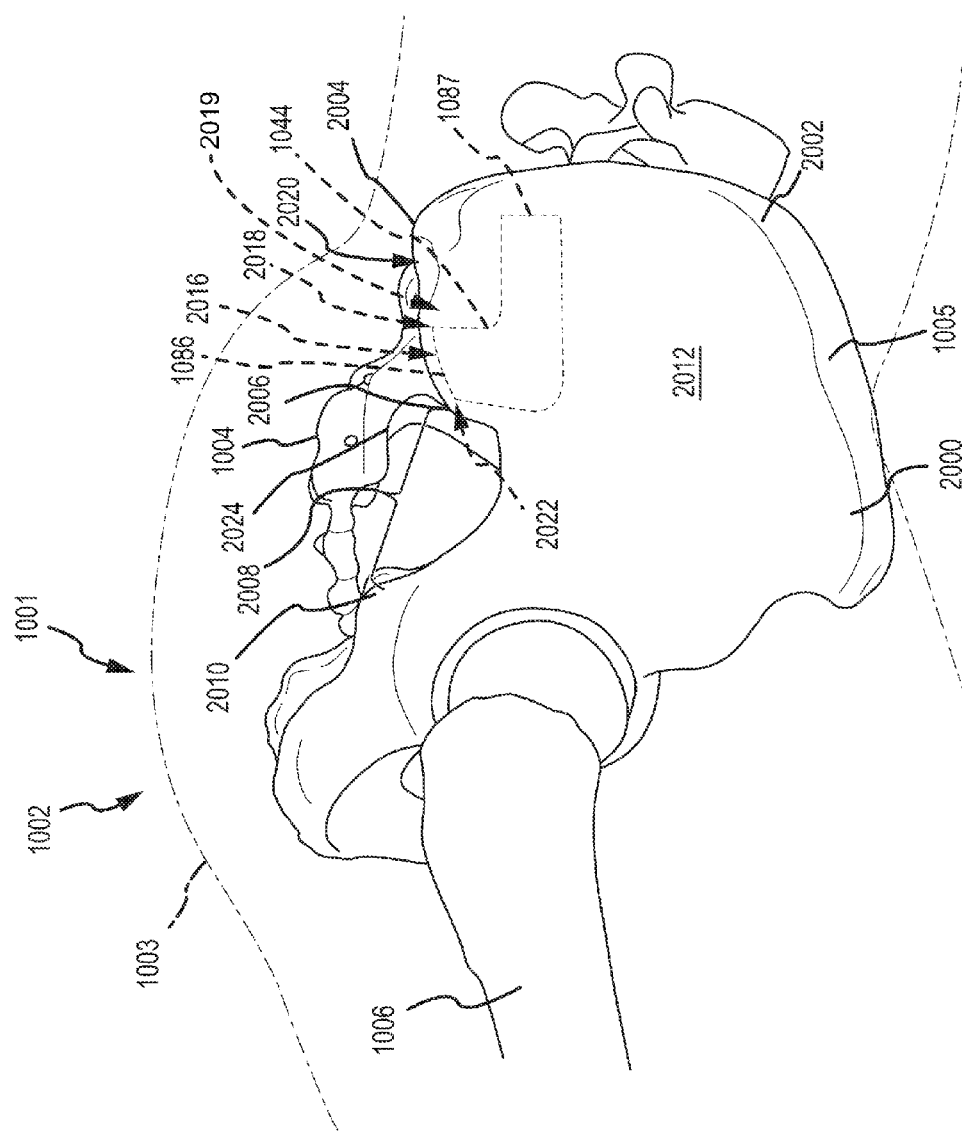
FIG. 11B is an enlarged view of the hip region of FIG. 11A.

Reference is first made to FIG. 11A, which is a right lateral view of a hip region 1002 of a patient 1001 lying prone, wherein the soft tissue 1003 surrounding the skeletal structure 1006 of the patient 1001 is shown in dashed lines. Delivery of an implant into the sacroiliac joint 1000 is via a posterior approach to the hip region 1002. FIG. 11B, which is an enlarged view of the hip region 1002 of FIG. 11A, depicts a lateral view of the patient's hip region 1002 reveals certain features of the ilium 1005, including the anterior superior iliac spine 2000, the iliac crest 2002, the posterior superior iliac spine 2004, the posterior inferior iliac spine 2006, the greater sciatic notch 2008 extending from the posterior inferior iliac spine 2006 to the ischial spine 2010, and the tubercle of iliac crest 2012.

The sacroiliac joint articular region 1044 is shown in dashed lines. A posterior inferior access region 2016 of the sacroiliac joint articular region 1044 has a superior end 2018 on the sacroiliac joint line 2019 that is between approximately 0 mm and approximately 40 mm inferior the posterior inferior overhang 2020 of the posterior superior iliac spine 2004. The posterior inferior access region 2016 of the sacroiliac joint articular region 1044 has an inferior end 2022 on the sacroiliac joint line that is at approximately the intersection of the posterior inferior iliac spine 2006 with the lateral anterior curved boundary 2024 of the sacrum 1004. In other words, the posterior inferior access region 2016 of the sacroiliac joint articular region 1044 has an inferior end 2022 on the sacroiliac joint line that is at approximately the superior beginning of the greater sciatic notch 2008.

Still referring to FIG. 11B, the sacroiliac joint articular region 1044 roughly defines an L-shape that includes a caudal region 1086 and a cranial region 1087. Access into the caudal region 1086 of the sacroiliac joint is via the posterior inferior access region 2016 that extends between corners defined by the superior end 2018 and the inferior end 2022. Access into the cranial region 1087 may be accomplished by continual, anterior travel in the caudal region 1086 until the articular region 1044 turns superiorly into the cranial region 1087.

Figure 11C:
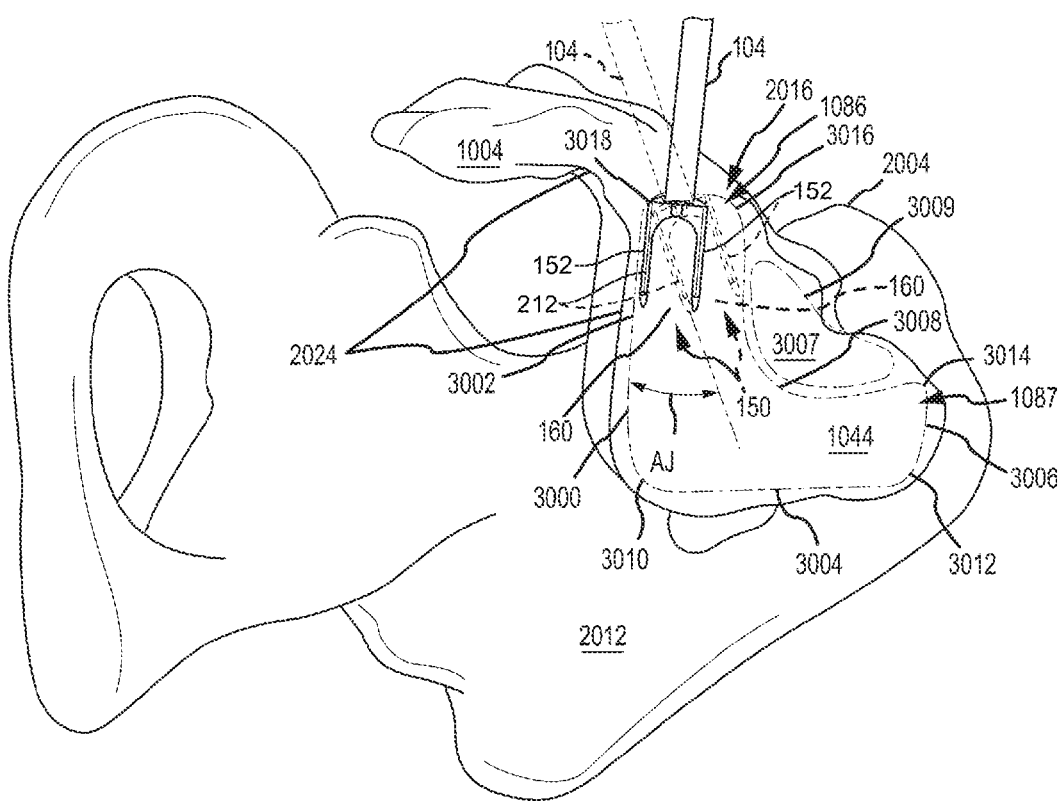
FIG. 11C is a close-up lateral side view of the hip region with the nearest ilium removed in order to show an implant positioned within the joint region

To begin a discussion of implant delivery into the sacroiliac joint articular region 1044, reference is made to FIG. 11C, which is a close-up lateral side view of the hip region 1002 of a patient 1001 with a nearest ilium 1005 removed in order to show the sacroiliac joint boundary 3000 defined along the sacrum 1004 and outlining the sacroiliac joint articular region 1044, and an implant 150 positioned for implantation within the sacroiliac joint articular region 1044.

As seen in FIG. 11C, boundaries along the sacroiliac joint articular region 1044 include an inferior boundary segment 3002, an anterior boundary segment 3004, a superior boundary segment 3006, and a posterior boundary segment 3008. The inferior boundary segment 3002 is immediately adjacent, and extends along, the sciatic notch 2024.

The inferior boundary segment 3002 and anterior boundary segment 3004 intersect to form an anterior-inferior corner 3010. The anterior boundary segment 3004 and superior boundary segment 3006 intersect to form an anterior-superior corner 3012. The superior boundary segment 3006 and posterior boundary segment 3008 intersect to form a superior-posterior corner 3014. The posterior boundary segment 3008 and posterior inferior access region 2016 intersect to form a superior-posterior corner 3016 of the posterior inferior access region 2016. The inferior boundary segment 3002 and posterior inferior access region 2016 intersect to form an inferior-posterior corner 3018 of the posterior inferior access region 2016.

The inferior boundary segment 3002 extends between corners 3010 and 3018. The anterior boundary segment 3004 extends between corners 3010 and 3012. The superior boundary segment 3006 extends between corners 3012 and 3014 and provides an access into the cranial portion 1087 of the sacroiliac joint. The posterior boundary segment 3008 extends between corners 3014 and 3016. The posterior inferior access region 2016 extends between corners 3016 and 3018 and provides an access into the caudal region 1086 of the sacroiliac joint. The posterior boundary segment 3008 separates articular region 1044 and extra-articular region 3007, which includes the sacral fossa on the sacrum 1004 and the corresponding iliac tuberosity on the ilium 1005 and defined by the extra-articular region boundary 3009.

In one aspect and as seen in FIG. 11C, the implant 150 may be delivered via an implant arm 104 of a delivery tool into the caudal region 1086 of the sacroiliac joint articular region 1044. As shown via the implant 150 and implant arm 104 shown in solid lines, in one embodiment, the implant 150 enters the posterior inferior access region 2016, and is further advanced into the caudal region 1086 of the sacroiliac joint articular region 1044, in an orientation such that the implant top and bottom surfaces 204, 206 (as shown in the implant 150 of FIG. 9) contact an articular surface of an ilium and sacrum, respectively, and the portion of the implant in between said implant surfaces resides generally in a plane of the sacroiliac joint while at least a portion of keels 152 and/or fins 212 extend across the joint plane into the bones defining the joint. In particular, keels and fins 152, 212 are generally parallel to and (the inferior of the pair are) immediately adjacent the inferior boundary segment 3002. Thus, the opened distal end 160 of the implant 150 is heading generally perpendicular to, and towards, the anterior boundary segment 3004.

As shown in FIG. 11C via the implant 150 and implant arm 104 shown in dashed lines, in one embodiment, the implant 150 enters the posterior inferior access region 2016, and is further advanced into the caudal region 1086 of the sacroiliac joint articular region 1044, in an orientation such that the implant arm 104 and keels 152 are in the joint plane and the fin 212 of the keels 152 next to the inferior boundary segment 3002 are somewhere between being generally parallel to the inferior boundary segment 3002 (as illustrated by the solid-lined implant 150 in FIG. 11C) or forming an angle AJ with the inferior boundary segment 3002 of up to approximately 50 degrees. Thus, the distal end 160 of the implant shown in dashed lines can be said to head anywhere from generally perpendicular to, and towards, the anterior boundary segment 3004 to heading generally towards the superior-anterior corner 3012, or points in between.

In one embodiment, the implant 150 may be first directed into the joint space as illustrated by the solid-lined implant 150 in FIG. 11C after which the implant 150 is rotated within the joint space to be positioned somewhere between, and including, angled position depicted by the dashed-lined implant 150. In other embodiments, the implant 150 may be first directed into the joint space as illustrated by the dashed-lined implant 150 in FIG. 11C after which the implant 150 is rotated within the joint space to be positioned somewhere between, and including, the parallel position depicted by the solid-lined implant 150. Thus, an implant 150 may be delivered non-transversely (i.e., within the joint and not across the joint) into the caudal region 1086, the cranial portion 1087, or partially within each of the caudal and cranial regions 1086, 1087 of the sacroiliac joint articular region 1044. Further details of the implant delivery can be found in related applications, such as U.S. patent application Ser. No. 12/998,712, filed Jan. 13, 2011, entitled "SACROILIAC JOINT FIXATION FUSION SYSTEM," which is incorporated by reference herein in its entirety.

C. Accessing and Preparing the Sacroiliac Joint for Implant and/or Anchor Delivery Now that an overview of the relevant anatomical landmarks and positioning of an implant non-transversely within the sacroiliac joint has been described, the discussion may now focus on delivery of an anchor and/or and implant into the surgical site. In doing so, reference will be made to FIGS. 12A-12H, among additional figures, which are steps in the methodology and illustrated in the same transverse cross section taken in along a plane extending medial-lateral and anterior posterior. In this cross section, articular surfaces 1016 are covered by a thick layer of articular cartilage with a joint space existing between them, the FIGS. 12A-12H are simplified for illustrative purposes and do not show these features to scale.

Now referring primarily to FIG. 12A, an embodiment of the method can include the step of placing a patient under sedation prone on a translucent operating table (or other suitable surface). The sacroiliac joint 1000 can be locally anesthetized to allow for injecting a radiographic contrast 1046 (as a non-limiting example, Isoview 300 radiographic contrast) under fluoroscopic guidance into the inferior aspect of the sacroiliac joint 1000 to outline the articular surfaces 1016 of the sacroiliac joint 1000) defined between the sacrum 1004 and ilium 1005, the sacroiliac joint 1000 having an interarticular region 1044. Injection of the radiographic contrast 1046 within the sacroiliac joint 1000 can be accomplished utilizing a tubular member 1047 (e.g., a syringe needle) having first tubular member end 1048 which can be advanced between the articulating surfaces 1016 of the sacroiliac joint 1000 and having a second tubular member end 1049 which removably couples to a hub 1050. The hub 1050 can be configured to removably couple to a syringe barrel 1051 or other device to contain and deliver an amount of radiographic contrast 1046. In the example of a syringe barrel 1051, the syringe barrel 1051 can have an internal volume capable of receiving an amount of the radiographic contrast 1046 sufficient for outlining the articular surfaces 1016 of the sacroiliac joint 1000, for example, under lateral fluoroscopy. A plunger 1052 can be slidingly received within the barrel 1051 to deliver the radiographic contrast 1046 through the tubular member 1047 into the sacroiliac joint 1000. The tubular member 1047 can have a gauge in the range of about 16 gauge and about 20 gauge and can further be incrementally marked on the external surface to allow determination of the depth at which the first needle end 1048 has advanced within the sacroiliac joint 1000. As the first needle end 1048 advances into the sacroiliac joint 1000 the radiographic dye 1046 can be delivered from within the syringe barrel 1051 into the sacroiliac joint 1000 to allow visualization of the sacroiliac joint 1000 and location of the tubular needle 1047 within the sacroiliac joint 1000.

Now referring primarily to FIG. 12B, once the first tubular member end 1048 has been sufficiently advanced into the sacroiliac joint 1000 and the articular surfaces 1016 of the sacroiliac joint 1000 have been sufficiently visualized, the hub 1050 can be removed from the tubular member 1047 leaving the tubular member 1047 fixed within the sacroiliac joint 1000 as an initial guide for tools subsequently used to locate or place the sacroiliac joint implant non-transversely between the articulating surfaces 1016 of the sacroiliac joint 1000 (e.g., locate the implant non-transversely to the joint plane 1030 generally defined by the articulating surfaces 1016 of the interarticular region 1044 of the sacroiliac joint 1000) or in removal of a portion of the sacroiliac joint 1000 within the region defined by the articular surfaces 1016 to generate an implant receiving space 1029 (shown in FIG. 12H). Alternately, one or more guide pins 1013 can be inserted along substantially the same path of the tubular member 1047 for fixed engagement within the sacroiliac joint 1000 and used in subsequent steps as a guide(s).

Figure 12D:
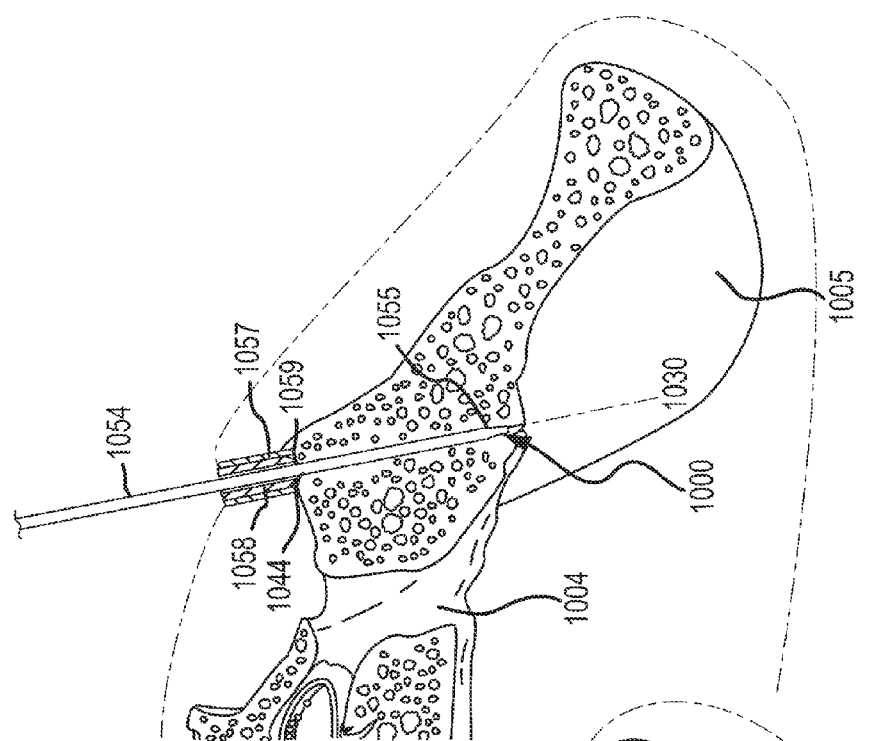
Figure 12C:
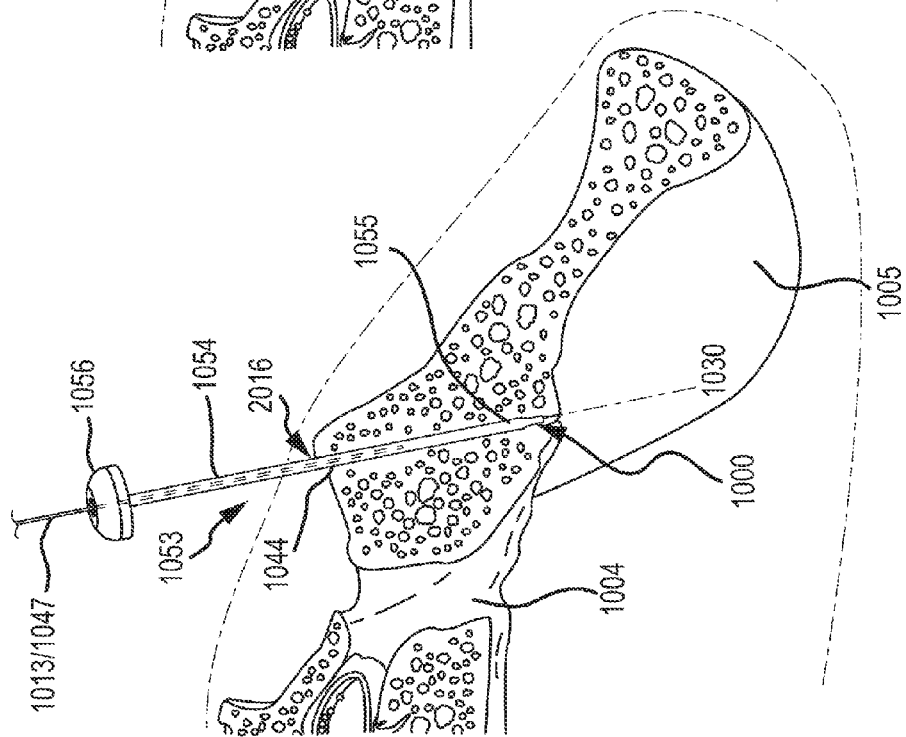

Now referring primarily to FIG. 12C, a small incision 1053 can be made in the skin at the posterior superior, or as to certain embodiments inferior, aspect of the sacroiliac joint 1000, extending proximal and distal to the tubular member 1047 along the line of the sacroiliac joint 1000 to provide a passage to access the interarticular space between the articulating surfaces 1016 (see FIG. 12B) of the sacroiliac joint 1000. More specifically, the small incision 1053 can be made along the joint line of the sacroiliac joint 1000 in the tissue covering the posterior inferior access region 2016 of the sacroiliac joint articular region 1044. A cannulated probe 1054 can be slidingly engaged with the tubular member 1047 (or guide pin 1013) extending outwardly from the sacroiliac joint 1000 (while the sacroiliac joint may be shown in the figures as being substantially linear for illustrative purposes, it is to be understood that the normal irregular features of the sacroiliac joint have not been removed). The cannulated probe 1054 can have a probe body 1054 of generally cylindrical shape terminating in a spatulate tip 1055 at the end advanced into the sacroiliac joint 1000. A removable cannulated probe handle 1056 couples to the opposed end of the probe body 1054. The spatulate tip 1055 can be guided along the tubular needle 1047 or guide wire 1013 into the posterior portion of the sacroiliac joint 1000 and advanced to the anterior portion of the sacroiliac joint 1000 under lateral fluoroscopic visualization. The cannulated probe handle 1056 can then be removed providing the generally cylindrical probe body 1054 extending outwardly from the sacroiliac joint 1000 through the incision 1053 made in the skin.

Alternatively, the probe 1054 can be used to guide, advance or place a needle, guide wire or other instrument up to, near, or into the joint.

Additionally, in particular embodiments, probe handle 1056 or the opposed end of the probe body 1054, or both, can be configured to have an interference fit or a luer lock hub to communicate with a syringe barrel 1051 in order to advance contrast, in situ curable biocompatible materials, stem cells, or etc through the cannulated probe 1054 or cannulated probe handle 1056.

Now referring primarily to FIG. 12D, a passage from the incision 1053 (see FIG. 12C) to the sacroiliac joint 1000 can be generated by inserting a cannula 1057 into the incision. A soft tissue dilator 1058 having a blunt end 1059 can be advanced over the probe body 1054, or a plurality of soft tissue dilators of increasing size, until the blunt end 1059 of the soft tissue dilator 1058 and the corresponding cannula end contact the posterior aspect of the sacroiliac joint 1000. More specifically, in one embodiment, the ends of the dilator 1058 and cannula 1057 contact the joint line 2019 of the sacroiliac joint 1000 at the posterior inferior access region 2016 of the sacroiliac joint articular region 1044. The soft tissue dilator 1058 can be removed from within the cannula 1057. The external surface of the cannula 1057 can be sufficiently engaged with the surrounding tissue to avoid having the tissue locate with in the hollow inside of the cannula 1057. A non-limiting embodiment of the cannula 1057 provides a tubular body having substantially parallel opposed side walls which terminate in a radius at both ends (lozenge shape) into which a plurality of different jigs can be inserted. Alternatively, as a non-limiting example, according to particular embodiments, cannula 1057 and corresponding dilators 1058 and alignment jigs 1060 can be configured to have tubular bodies with an elliptical or circular cross section.

In some embodiments, the cannula 1057 may be additionally configured to have within or near its walls a light source such as, for example, a fiberoptic or a LED light source to assist in visualization of the working area. Also, in some embodiments, irrigation and suction tubing may communicate with the inside passage of cannula 1057.

At this stage or at other stages of the methodology, additional tools and methods may be employed to provide access to the sacroiliac joint 1000 as described in U.S. patent application Ser. No. 13/475,695 filed May 18, 2012 entitled "SYSTEMS FOR AND METHODS OF FUSING A SACROILIAC JOINT," which is hereby incorporated by reference in its entirety. Additionally, at this stage or others, the sacroiliac joint 1000 may be surgically prepared for a fusion procedure using various tools and methods described in U.S. patent application Ser. No. 14/514,221 filed Oct. 14, 2014 entitled "SYSTEMS FOR AND METHODS OF PREPARING A SACROILIAC JOINT FOR FUSION," which is hereby incorporated by reference in its entirety.

Now referring to FIG. 12E, a cannulated drill bit 1070 can be advanced over the probe body 1054 and within a drill guide hole of the first drill jig 1067. The cannulated drill bit 1070 under fluoroscopic guidance can be advanced into the interarticular region 1044 between the articulating surfaces 1016 of the sacroiliac joint 1000 to produce a first bore 1071 (shown in broken line) to a determined depth. As to certain embodiments of the method, an amount of articular cartilage or other tissues from between the articular surfaces 1016 of the sacroiliac joint 1000 can be removed sufficient to allow embodiments of the sacroiliac joint implant 150 to be implanted in replacement of the removed articular cartilage or tissue. Because the method removes the degenerative articular cartilage or tissue between the articular surfaces 1016 of the sacroiliac joint 1000, the articular surfaces 1016 of the sacroiliac joint 1000 can remain intact or substantially intact allowing the sacroiliac joint implant 150 to be non-transversely located between the articular surfaces 1016 of the sacroiliac joint 1000. Understandably, other instruments can be utilized separately or in combination with a cannulated drill bit 1062 for the removal of articular cartilage or tissue between articular surfaces 1016 such as: box chisels, side cutting router bits, burs, flexible burs and bits, hole saws, curettes, lasers (such as C02, Neodymium/YAG (yttrium-aluminum-garnet), argon, and ruby), electrosurgical equipment employing electromagnetic energy (the cutting electrode can be a fine micro-needle, a lancet, a knife, a wire or band loop, a snare, an energized scalpel, or the like) where the energy transmitted can be either monopolar or bipolar and operate with high frequency currents, for example, in the range of about 300 kHz and about 1000 kHz whether as pure sinusoidal current waveform where the "crest factor" can be constant at about 1.4 for every sinus waveform, and a voltage peak of approximately 300 V to enable a "pure" cutting effect with the smallest possible coagulation effect or as amplitude modulated current waveforms where the crest factor varies between 1.5 and 8, with decreasing crest factors providing less of a coagulation effect. Electrosurgical waveforms may be set to promote two types of tissue effects, namely coagulation (temperature rises within cells, which then dehydrate and shrink) or cut (heating of cellular water occurs so rapidly that cells burst). The proportion of cells coagulated to those cut can be varied, resulting in a "blended" or "mixed" effect. Additionally, a fully rectified current, or a partially rectified current, or a fulguration current where a greater amount or lateral heat is produced can be employed to find the articular surfaces of the joint and aid in advancing a probe or guide wire into a position in between the articulating surfaces. These currents can effectively degrade the cartilage and allow advance into the joint without grossly penetrating much beyond the cartilage.

Now referring to FIG. 12F, as to certain embodiments, the first drill jig 1067 can be removed from within the cannula 1057 and a second drill jig 1072 can be advanced over the probe body 1054 and received within the cannula 1057; however, the methodology is not limited to any particular number of drill jigs and as to certain embodiments of the method the first drill jig 1067 can include all the required drill guide hole(s) 1068 (or slots or other configurations of the drill guide) and as to other embodiments of the method a plurality of drill jigs can be utilized in serial order to provide all the drill guide holes 1068. As to the particular embodiment shown by the Figures, the first drill jig 1067 can provide one or more additional drill guide holes 1068 which guide in relation to the first bore 1071a second or more cannulated drills 1062 of the same or different configuration to be inserted within and advanced into the sacroiliac joint 1000 to produce a second bore 1073 (generally shown in broken line as 1071/1073) or a plurality of bores within the sacroiliac joint 1000 spaced apart in predetermined pattern to allow removal of sufficient articular cartilage 1016 or other tissue from the interarticular space of sacroiliac joint 1000 for placement of embodiments of the sacroiliac joint implant 150 within the region defined by and between the paired articular surfaces 1016 of the sacroiliac joint 1000. As to certain methods described herein, the first drill jig 1067 or the second drill jig 1072 or a plurality of drill jigs can be utilized in serial order to remove a portion of the sacroiliac joint 1000 for generation of an implant receiving space 1029 (shown in FIG. 12H). As these embodiments of the method, articular cartilage or other tissues and sufficient subchondral bone can be removed from between the articular surfaces 1016 of the sacroiliac joint 1000 sufficient to allow placement of certain embodiments of the sacroiliac joint implant 150 and one or more keel or fin 152, 212 receiving channels 1074 can be cut into at least one of the articular surfaces 1016 of said sacroiliac joint 1000 sufficient to receive other embodiments of the sacroiliac implant 150. The one or more keel or fin receiving channels 1074 can be cut a depth into the subchondral, cortical bone or cancellous bone of the sacrum 1004 or ilium 1005.

Now referring primarily to FIG. 12G, in a subsequent step, the last in the serial presentation of drill jigs 1067, 1072 can be removed from within the cannula 1057 and a broach jig 1075 can be advanced over the probe body 1054 to locate within the cannula 1057. The broach jig 1075 can include a broach guide hole 1076 which receives a first broach end 1077 of a cannulated broach 1078 advanced over the probe body 1054. The first broach end 1077 can have a configuration which can be advanced into the sacroiliac joint 1000. As to certain embodiments of the method, the first broach end 1077 can be adapted to remove an amount of articular cartilage and other tissue from between the articular surfaces 1016 within the articular region 1044 of the sacroiliac joint 1000 for non-transverse placement of a sacroiliac joint implant 150 As to other embodiments of the method, the cannulated broach 1078 can remove a sufficient portion of the sacroiliac joint 1000 to generate an implant receiving space 1029 to receive embodiments of the sacroiliac joint implant 150.

As a non-limiting example, FIG. 12G shows a broach 1078 configured to remove a portion of the sacroiliac joint 1000 to produce an implant receiving space 1029 (shown in FIG. 12H) to receive embodiments of the sacroiliac joint implant 150 such that the broach has an outer surface and outer surface cross section along its length which may generally or substantially match the implant 150 outer surface profile including the keels and fins 152, 212.

D. Utilizing the Delivery Tool Described Herein to Deliver an Anchor and/or Implant into the Surgical Site As mentioned previously, the delivery tool described herein may be used to deliver an anchor transversely across the plane of the sacroiliac joint and to subsequently deliver an implant non-transversely within the plane of the joint such that the anchor is positioned within the graft window of the implant. The delivery tool described herein may also be used to deliver the implant and to subsequently deliver the anchor in the described orientation. While the method discussed herein will focus on the delivery of the anchor and then the implant, the steps of the method may be modified to first deliver the implant and then the anchor.

Figure 13A:
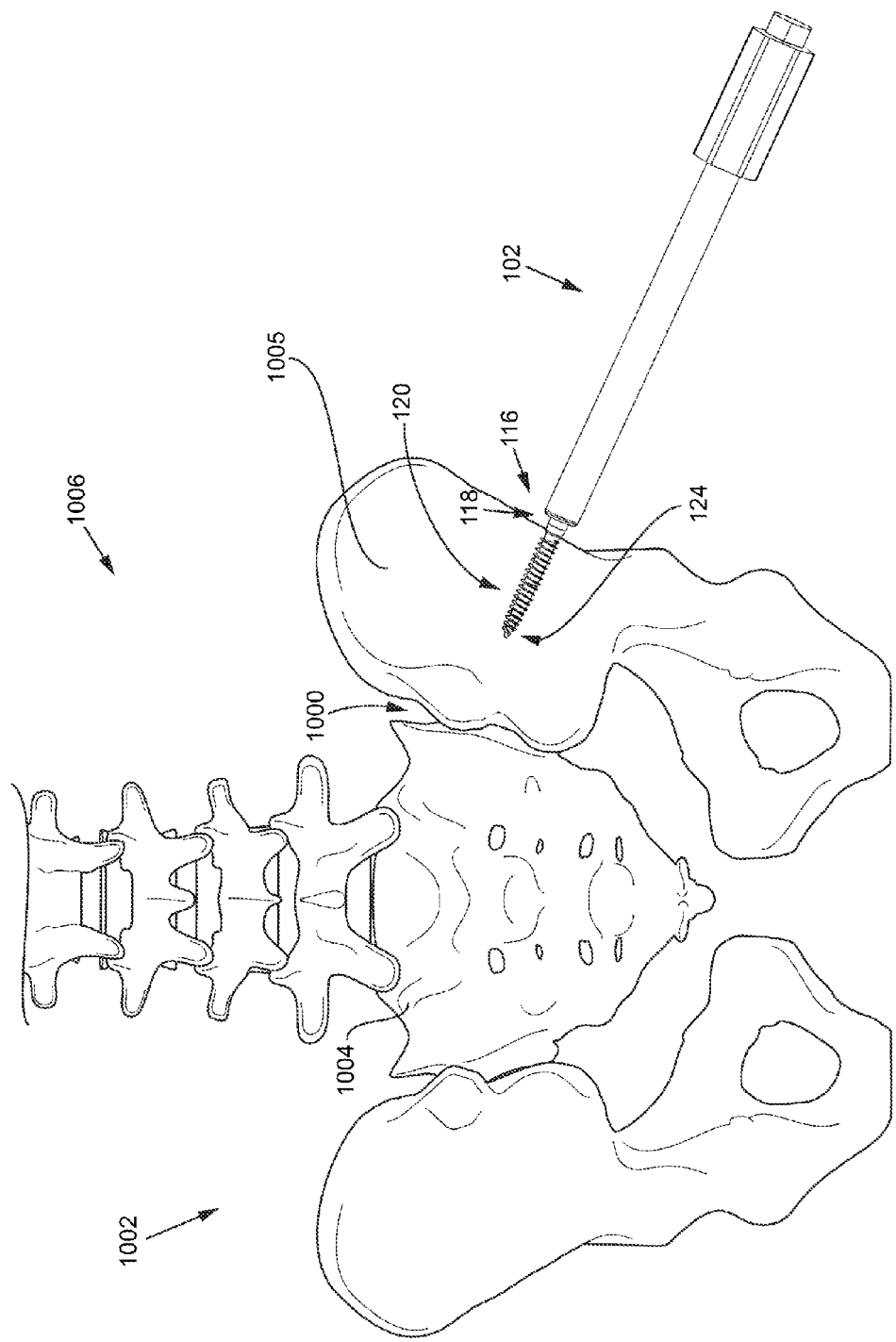
FIG. 13A is a posterior view of a hip region of a skeletal structure and an isometric view of an anchor arm approaching a lateral surface of an ilium.

To begin, reference is made to FIG. 13A, which is a posterior view of a hip region 1002 of a skeletal structure 1006 and an isometric view of an anchor arm 102 approaching a lateral surface of an ilium 1005. As seen in the figure, the distal end 116 of the anchor arm 102 may be coupled with a proximal end 118 of an anchor element 120 and the distal end 124 of the anchor element 120 may be positioned to be delivered non-transversely or across the sacroiliac joint 1000. In this case, the distal end 124 of the anchor element 120 is positioned to be delivered first through the ilium 1005 and then through the sacrum 1004. The anchor arm 102 may, however, be positioned to deliver the anchor element 120 non-transversely first through the sacrum 1004 and then through the ilium 1005.

Although not shown in FIG. 13A, a sleeve may extend through an incision in the patient's soft tissue such that a distal end of the sleeve is positioned generally against the lateral surface of the ilium 1005. The anchor arm may then be positioned within the sleeve and guided to the surface of the ilium 1005. In this arrangement, a longitudinal axis of the sleeve may be such that it is generally coaxial with a longitudinal axis of the anchor arm 102.

The anchor arm 102 may be positioned to deliver the anchor element 120 through the sacroiliac joint articular region 1044 (as seen in FIG. 11B). And, since the delivery tool 100 described herein includes a rotating joint at the connection of the positioning arm 106 and the implant arm 104 (as seen in FIG. 1), the exact trajectory of the anchor arm 102 relative to the sacroiliac joint 1000 need not be exact. That is, the rotating joint allows for adjustment such that the anchor element 120 may be delivered in a range or orientations relative to the sacroiliac joint and the delivery tool may be adjusted via the rotating joint so that the implant may be delivered into the joint with the anchor positioned within the graft window of the implant.

Figure 13B:
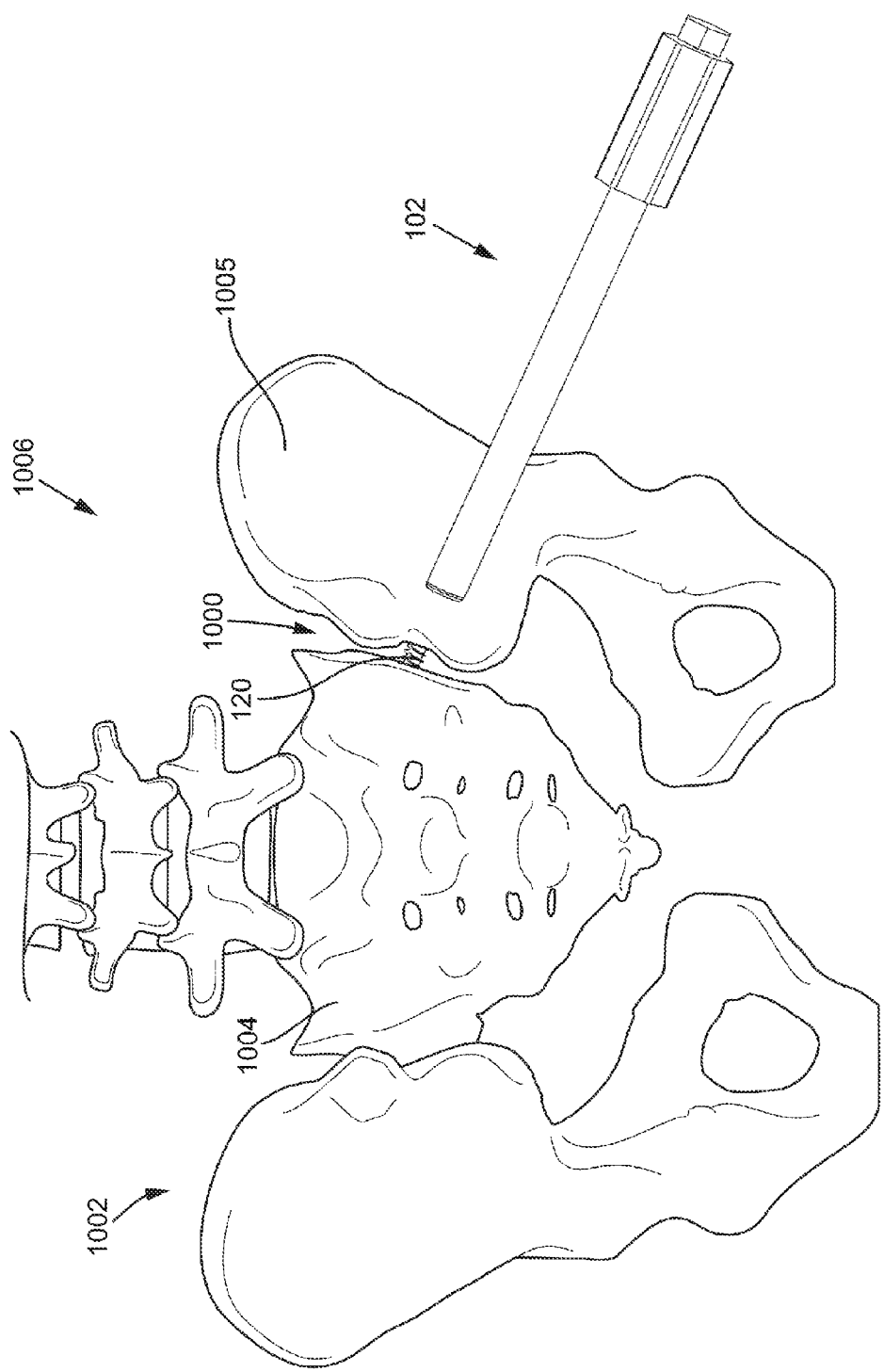
FIG. 13B is the same view of the hip region of FIG. 13A but with the anchor arm advanced relative to the ilium.

Turning now to FIG. 13B, which is the same view of the hip region 1002 as in FIG. 13A, once the anchor arm 102 is positioned relative to the sacroiliac joint 1000, the anchor arm 102 may be advanced relative to the ilium 1005 to deliver the anchor element 120 through the ilium 1005, the sacroiliac joint 1000, and sacrum 1004. The anchor element 120 may be rotationally advanced by a surgeon rotating the anchor arm 102 by hand or by a drill (not shown). Additionally, a drill may be used to predrill a pilot hole in which the anchor arm 102 will subsequently be used to deliver the anchor element 120 within the pilot hole.

Figure 13C:
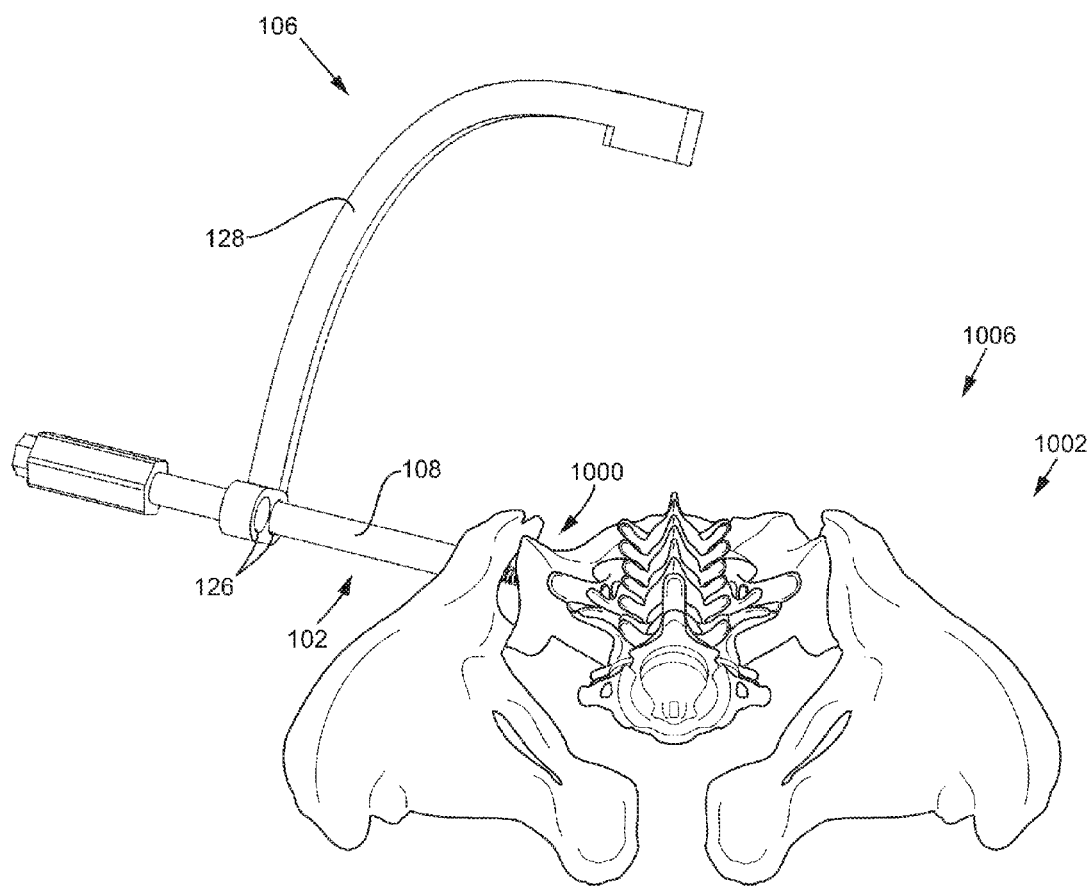
FIG. 13C is a top view of the hip region of the skeletal structure looking caudal with the positioning arm coupled with the anchor arm.

Once the anchor element 120 is delivered, the positioning arm 106 may be coupled with the anchor arm 102, as illustrated in FIG. 13C, which is a top view of the hip region 1002 of the skeletal structure 1006 looking caudal. As seen in the figure, the positioning arm 106 is slideably coupled with the anchor arm 102. In particular, the anchor shaft 108 is received within one of the collars 126 of the positioning arm 106. In this particular arrangement, the anchor shaft 108 is positioned within the particular collar 126 that is in-plane with the positioning member 128.

Figure 13D:
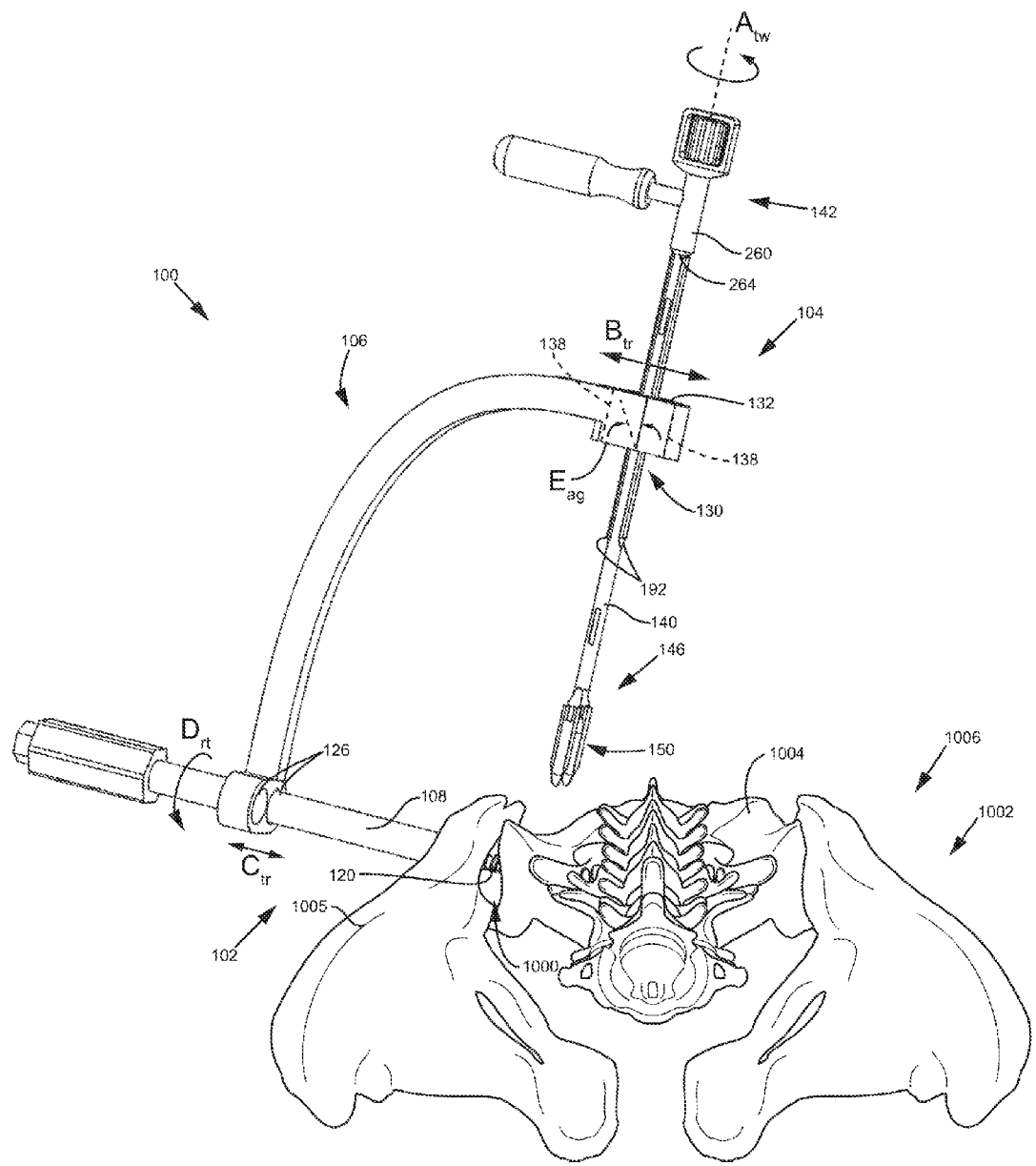
FIG. 13D is the same view of the hip region of the skeletal structure of FIG. 13C but with the implant arm coupled to the positioning arm.

Turning to FIG. 13D, which is the same view of the hip region 1002 of the skeletal structure 1006 as FIG. 13C, the implant arm 104 is coupled with the positioning arm 106. One method of coupling the implant arm 104 and the positioning arm 106 is by extending the distal end 146 implant arm 104, being uncoupled with the implant 150, through the channel 130 of the positioning arm 106 and, then, coupling the implant 150 with the implant arm 104. Other methods may include extending the implant arm 104, being coupled with the implant 150, through the channel of the positioning arm 106; that is, if the implant 150 is of a small enough size to fit through the channel 130.

As seen in FIG. 13D, the portion of the implant shaft 140 having the pair of members 192 is positioned within the channel 130. And, the amount of distal movement of the implant arm 104 relative to the channel 130 is limited by the enlarged body 260 of the handle assembly 142, which is configured to contact the proximal edge 132 of the channel 130 and restrict further distal movement of the implant arm 104.

Once the implant arm 104 is positioned within the channel 130 of the positioning arm 106, the implant arm 104 may be aligned to deliver the implant 150 within the sacroiliac joint 1000. Various adjustments to the various components of the delivery tool 100 may be made while keeping the anchor arm 102 in place. As an example, the rotation or twist $A_{tw}$ along a longitudinal axis of the implant arm 104 and, thus, the implant 150 may be adjusted to align the implant 150 with the plane of the sacroiliac joint 1000. More particularly, the twist $A_{tw}$ of the implant 150 may be adjusted so that the keels 152 are positioned within the plane of the joint. The amount of twist $A_{tw}$ is restricted to the geometric configuration of the members 192 extending off the implant shaft 140. Thus, if the implant arm 104 is able to twist into a particular orientation without being "locked" or restricted from further movement within the channel 130, then the particular orientation is such that it will deliver the implant 150 into an appropriate orientation relative to the pre-delivered anchor element 120.

As another example of an adjustment to the components of the delivery tool 100, the implant arm 104 may translate $B_{tr}$ within the channel 130 towards either of the opposite end walls 138. A similar translational adjustment $C_{tr}$ may be performed by translating the positioning arm 106 via sliding the collar 126 on the anchor shaft 108 of the anchor arm 102. As stated previously, the positioning arm 106 may be secured in position on the anchor shaft 108 by, for example, fasteners (e.g., set screw, clamp). Or, the positioning arm 106 may freely translate $C_{tr}$ and rotate $D_{rt}$ on the anchor shaft 108. If the translation $C_{tr}$ and rotation $D_{rt}$ is secured in position on the anchor shaft 108, the implant arm 104 may be translationaly adjusted $B_{tr}$ within the channel 130 to accomplish a similar or the same function.

Another example of an adjustment to the components of the delivery tool 100 includes adjusting an angle $E_{ag}$ of delivery of the implant 150. The implant arm 104 may be angled within the channel 130 to align the implant 150 in a trajectory that will position the implant 150 within the sacroiliac joint 1000. Such an adjustment may be necessary depending on the relative angle of delivery of the anchor element 120 with respect to the lateral surface of the ilium 1005.

Figure 13E:
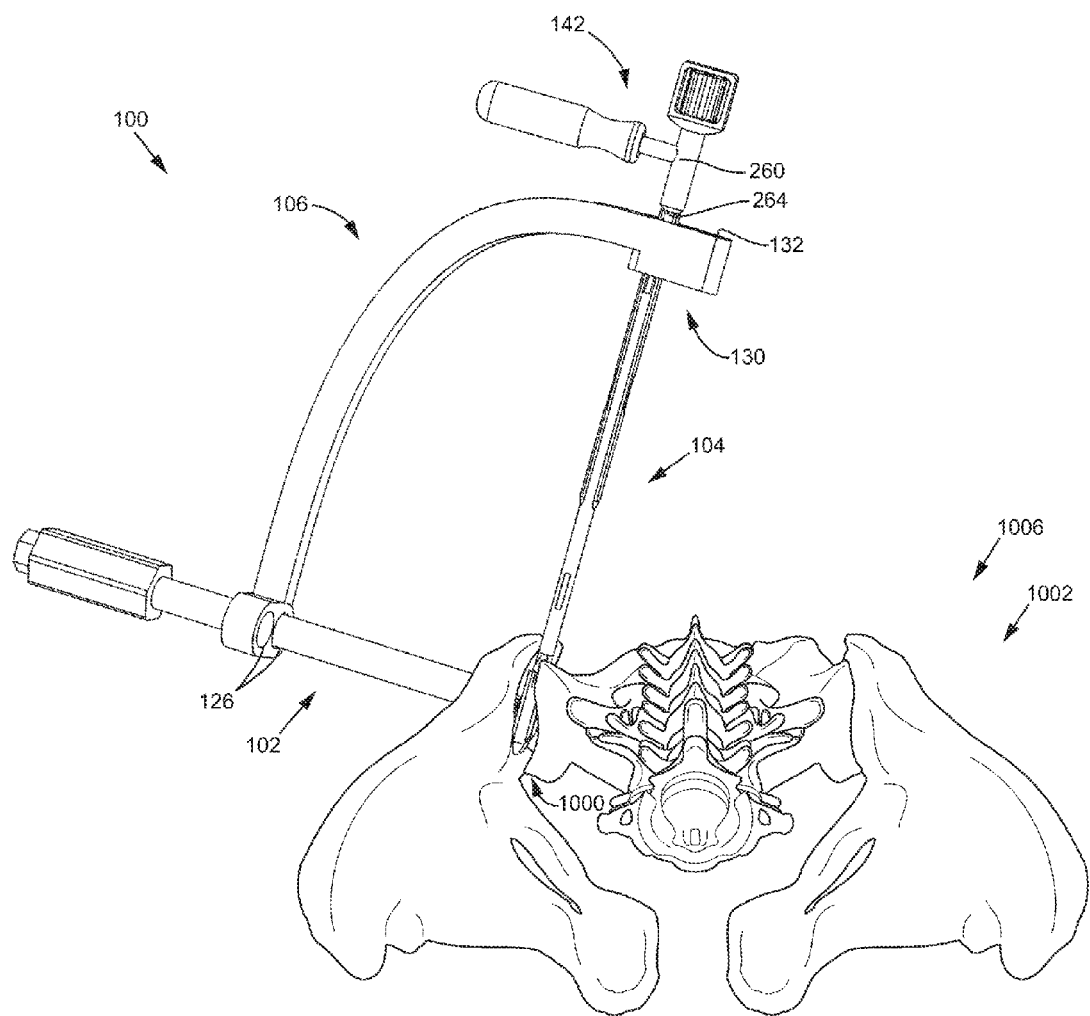
FIG. 13E is the same view of the hip region of the skeletal structure of FIGS. 13C-13D but the implant is positioned within the sacroiliac joint.
Figure 13F:
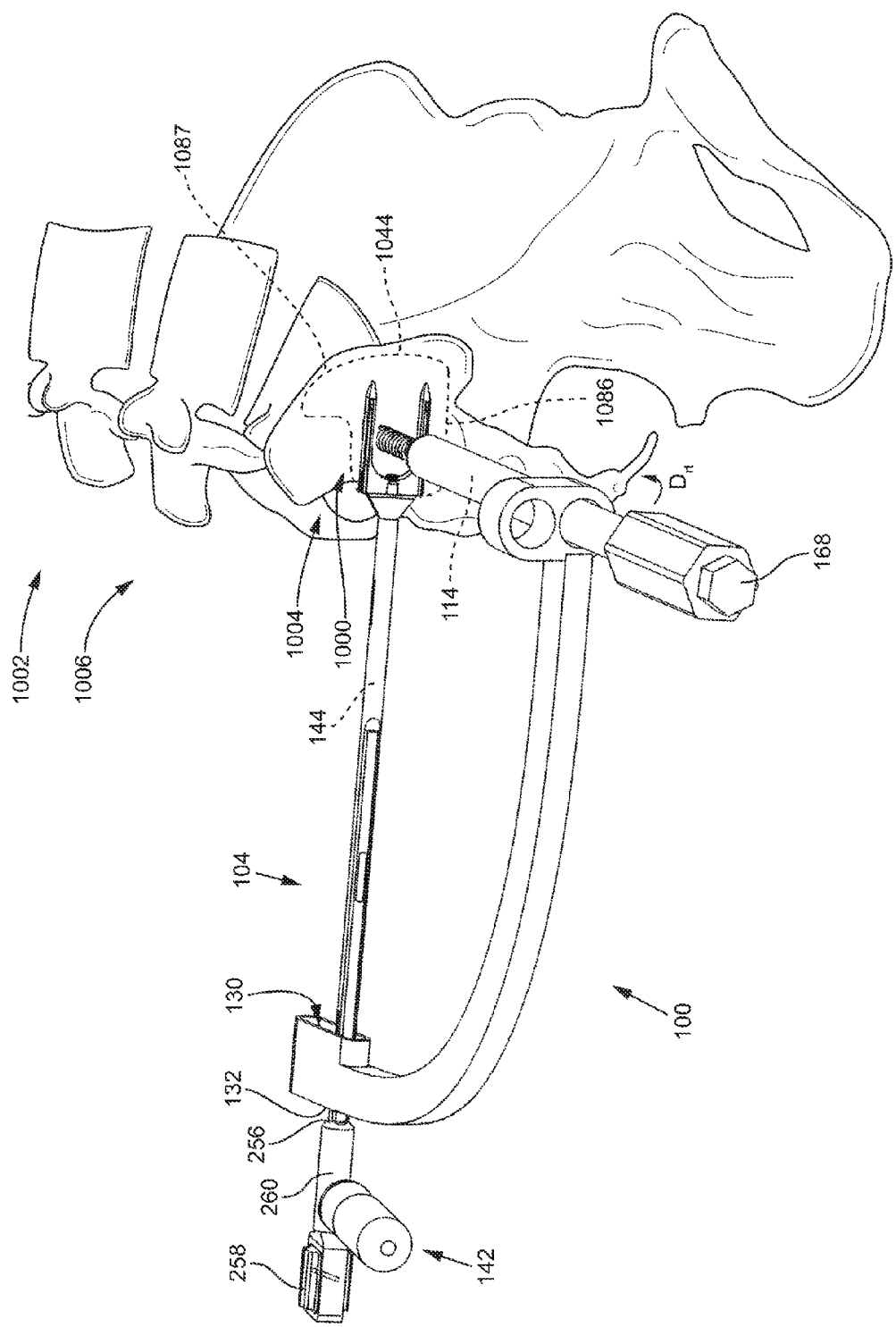
FIG. 13F is a side view of the hip region of the skeletal structure with the nearest ilium removed to show the implant and anchor positioned within the sacroiliac joint.

Once the implant arm 104 is aligned in a trajectory that will align the implant 150 within the sacroiliac joint 1000, the implant arm 104 may be distally advanced relative to the sacroiliac joint 1000, as illustrated in FIG. 13E, which is the same view of the hip region 1002 of the skeletal structure 1006 as FIG. 13C-13D. As seen in FIG. 13E, the implant arm 104 is distally advanced such that the distal end 264 of the enlarged body 260 of the handle assembly 142 abuts the proximal edge 132 of the channel 130 of the positioning arm 106. In this orientation, as shown in FIG. 13F, which is a side view of the hip region 1002 of the skeletal structure 1006 with the ilium removed to show the sacroiliac joint 1000 and sacrum 1004, the anchor element 120 is positioned within the graft window 158 of the implant 150. Also as seen in FIG. 13F, the implant 150 is inserted into the caudal region 1086 of the articular region 1044 of the sacroiliac joint 1000 such that the keels 152 are positioned within a plane of the joint. In this way, the graft window 158 allows for bone growth through the implant 150 (i.e., through the graft window 158) and across the joint 1000.

In certain embodiments, the implant 150 may be first directed in the joint space as illustrated in FIG. 13F after which the implant 150 is rotated $D_{rt}$ within the joint space to be positioned somewhere between the cranial and caudal portions 1087, 1086 of the articular region 1044. In other embodiments, the implant 150 is not rotated, but simply inserted into the articular region 1044.

Once the implant 150 and anchor element 120 are delivered into their respective locations, the implant arm 104 and the anchor arm 102 may be decoupled from the implant 150 and the anchor element 120. The implant 150 may be decoupled from the implant arm 104 by rotationally engaging the head 258 on the handle assembly 142. This engagement threadably releases the implant retainer 144 from the implant 150. The anchor element 120 may be decoupled from the anchor arm 102 by rotationally engaging the head 168 of the anchor retainer 114. This engagement threadably releases the anchor retainer 114 from the anchor element 120. Once disengaged, the anchor arm 102, the implant arm 104, and the positioning arm 106 may be removed and the surgical procedure may continue.

III. Additional Embodiments of the Delivery Tool and Implants

A. Positioning Arm with Angulating Collars

Figure 14B:
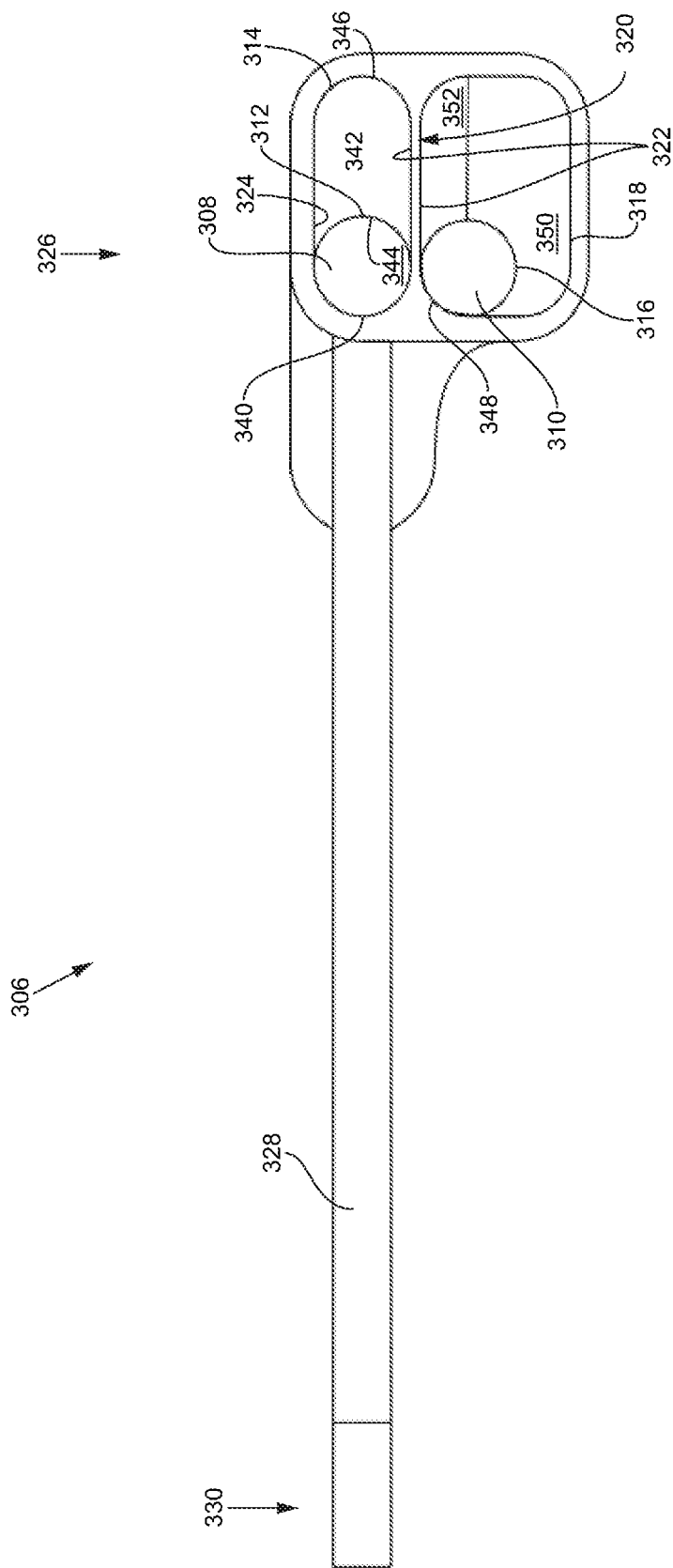
FIG. 14B is a bottom view of the positioning arm of FIG. 14A.

Various modifications to the delivery tool 100 discussed herein are possible and contemplated by the present disclosure. One such modification to the positioning arm 306 is illustrated in FIGS. 14A-14F. As seen in FIG. 14A, the positioning arm 306 is similar to the positioning arm previously described in that it includes an arcuate positioning member 328 extending between a channel 330 and a pair of collars 326. The channel 330 is identical to previously described embodiments in that it is formed by generally parallel side walls 336 and rounded end walls 338 that extend from a proximal edge 332 to a distal edge 334. The channel 330 is configured to receive an implant arm (not shown in FIG. 14A) and restrain its rotation to a limited, predetermined range. The channel 330 and the implant arm form a rotating joint about which the implant arm may be rotated relative to positioning arm 306 and an anchor arm (not shown in FIG. 14A), or vice versa.

Opposite the channel 330, the collars 326 are configured to allow certain predefined angulation of an anchor arm positioned within the collars 326. The collars 326 include an in-line collar 308 that is positioned in a common plane with the positioning member 328 and an offset collar 310 that is positionally or laterally offset from a plane of the positioning member 328. While in previously described embodiments of the positioning arm 306 the angling of the anchor arm relative to the positioning arm was restrained, in the present embodiment of the positioning arm 306, as seen in FIG. 14A, the collars 326 allow for angulation of an anchor arm positioned within one of the collars 326.

As illustrated in FIG. 14B, which is a bottom view of the positioning arm 106, the in-line collar 308 includes a circular proximal edge 312 and a stadium-shaped distal edge 314. The offset collar 310 includes a circular proximal edge 316 and a rounded-rectangle-shaped distal edge 318. As seen in FIG. 14B, a partition wall 320 having generally parallel side walls 322 separates the in-line collar 308 and the offset collar 310. The in-line collar 308 also includes an inner side wall 324 that is opposite of and generally parallel with the partition wall 320. Extending between the inner side wall 324 and the side wall 322 of the partition wall 320 is a rounded wall 340. Opposite the rounded wall 340 is a sloped wall 342 that extends from a forward end 344 of the circular proximal edge 312 to a forward end 346 of the stadium-shaped distal edge 314. In this way, an anchor arm positioned within the in-line collar 310 is restrained from angling outside a plane defined by the positioning member 328 by the side wall 322 of the partition wall 320 and the inner side wall 324. The anchor arm may, however, angulate within the plane that is common to the positioning member 328.

Turning to the offset collar 310, as seen in FIG. 14B, the collar 310 includes a rounded wall 348 that is adjacent the side wall 322 of the partition wall 320. The offset collar 310 additionally includes a sloped side wall 350 that is opposite the side wall 322 of the partition wall 320 and a sloped front wall 352 that is opposite the rounded wall 348. In this way, an anchor arm may be positioned within the offset collar 310 and angled such that an anchor shaft of the anchor arm is positioned against one of the sloped walls 350, 352. The offset collar 310 permits more angulation of the anchor arm, as compared with the in-line collar 308, because the offset collar 310 is configured to position an anchor element at a distal end of an anchor arm outside of a graft window of an implant. Thus, a surgeon has fewer limitations as to where to place the anchor when it is positioned outside the confines of a graft window of the implant. When using the in-line collar 308, however, there are more limitations because the in-line collar 308 is configured to align an anchor at a distal end of the anchor arm within the graft window of an implant. The angulation of the anchor arm within the in-line collar 308 allows for angulation that will either position the anchor within the graft window of the implant or distal of the graft window of the implant while restricting angulations that would allow the anchor to contact the body of the implant.

Figure 14C:
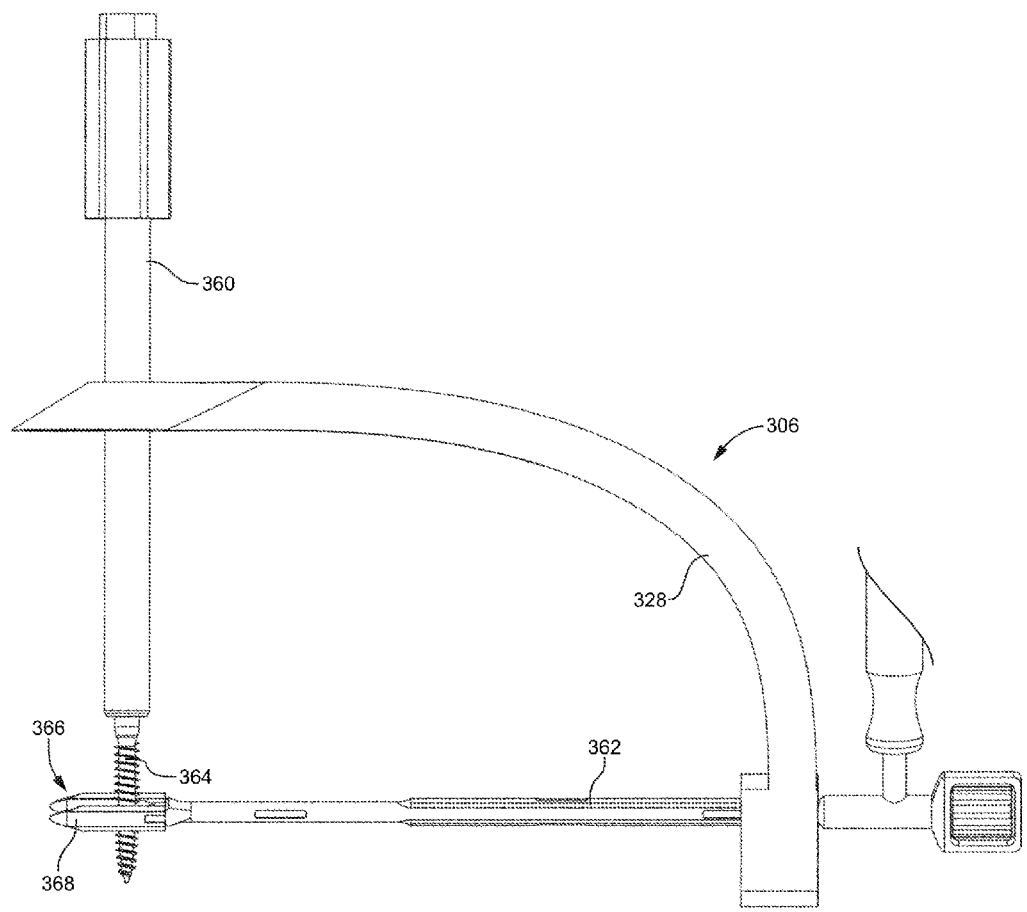
FIG. 14C is a side view of the positioning arm of FIG. 14A coupled with an implant arm and an anchor arm.
Figure 14D:
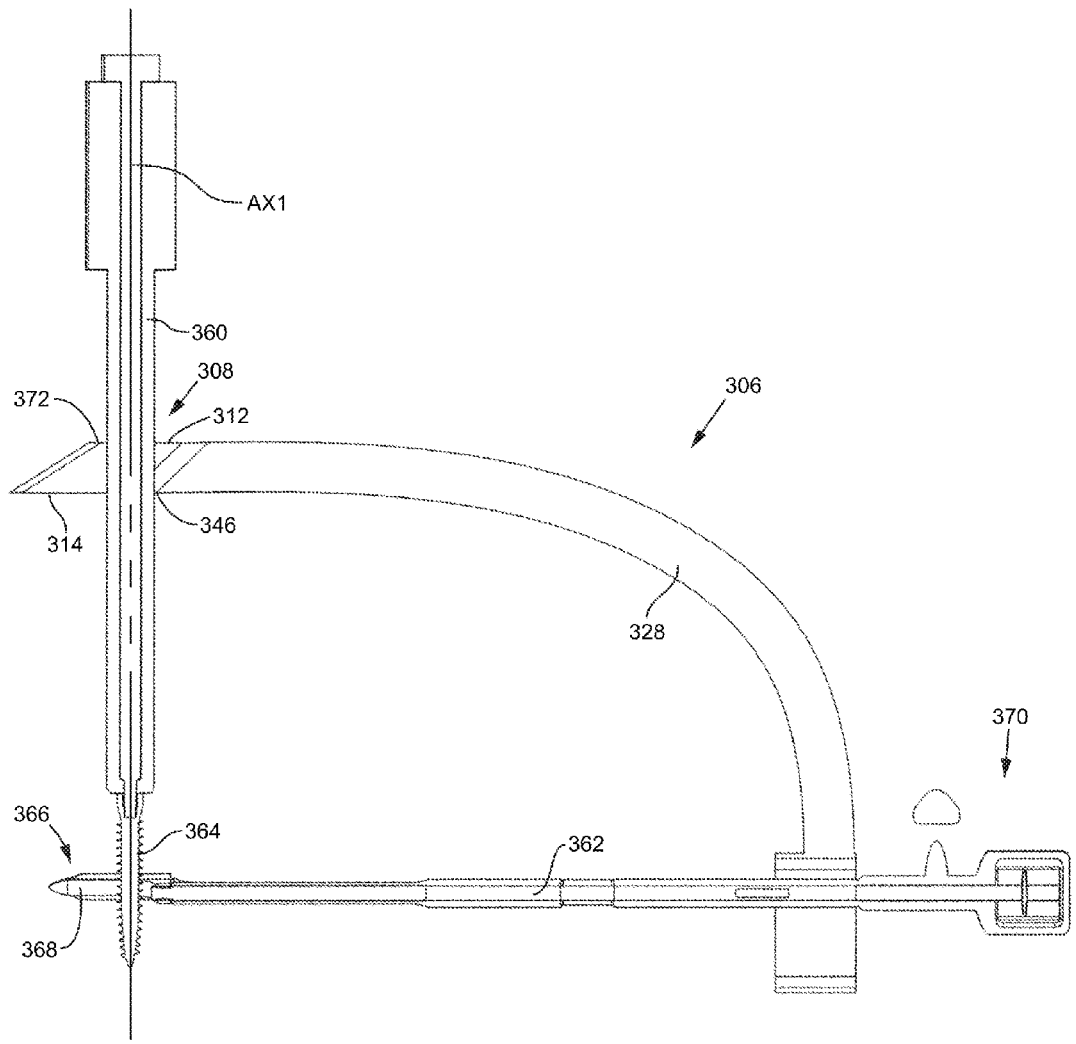
FIG. 14D is a cross-sectional view of the positioning arm, implant arm, and anchor arm of FIG. 14C with an anchor positioned within a graft window of an implant.
Figure 14E:
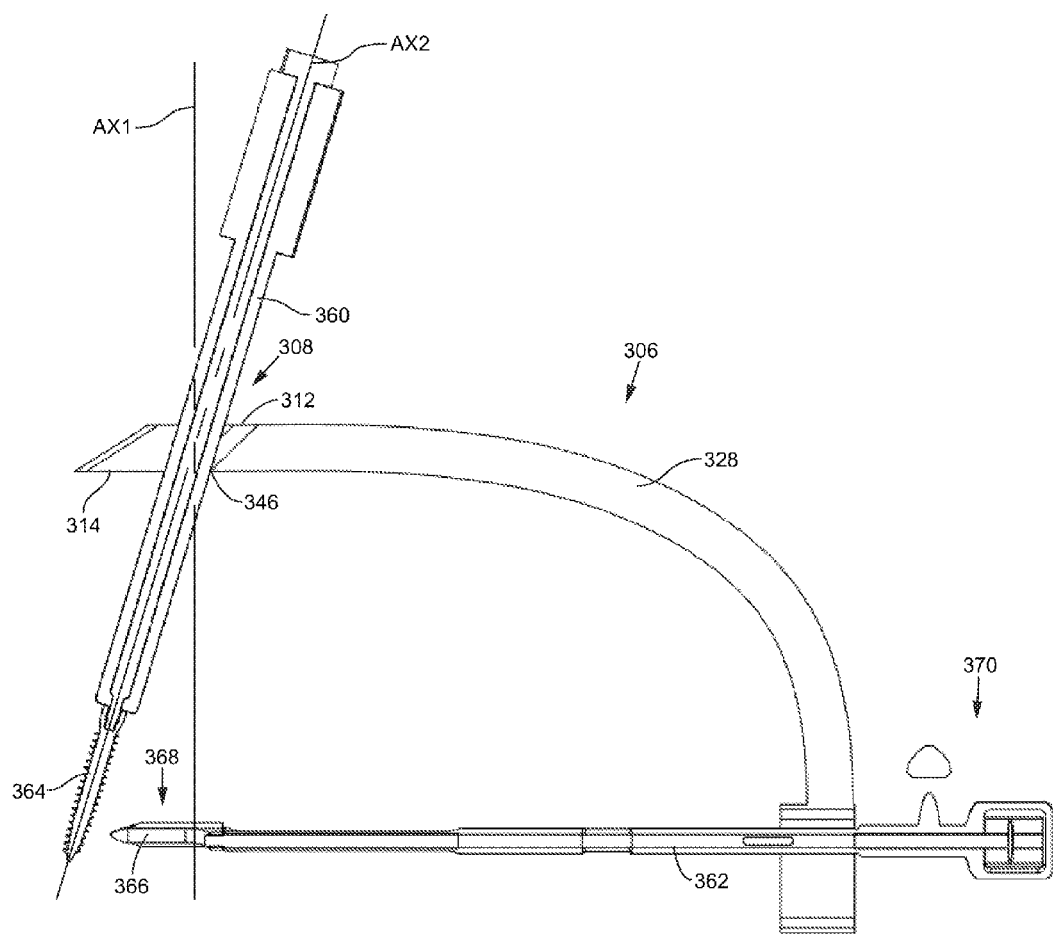
FIG. 14E is a cross-sectional view of the positioning arm, implant arm, and anchor arm of FIG. 14C with the anchor positioned distal of the graft window of the implant.

Reference is now made to FIG. 14C, which is an side view of the positioning arm coupled between an anchor arm 360 and an implant arm 362 with a longitudinal cross section down the plane of the positioning member 328. As seen in the figure, an anchor 364 is positioned within a graft window 366 of an implant 368. Turning to FIG. 14D, which is the same view as of FIG. 14C, except shown in cross section, the proximal edge 312, in this embodiment, is elongated as opposed to circular. In this arrangement, the anchor arm 360 may be positioned within the in-line collar 308 in a number of orientations. For example, the anchor arm 360 may be positioned along axis AX1 where the anchor 364 is oriented generally perpendicular to the implant arm 362 and the implant 368. Further angling of the anchor 364 towards a handle 370 of the implant arm 362 is restricted by the anchor arm 360 contacting a forward edge 372 of the proximal edge 312 and a rear edge 346 of the distal edge 314 of the in-line collar 308. As seen in FIG. 14, the anchor arm 360 may angulate away from the implant 366 (i.e., distal of the graft window 368) along an axis AX2. As seen in the figure, the anchor arm 360 may angulate even further past axis AX2 and will be limited by the particular geometry of the distal and proximal edges 314, 312. In this and other embodiments of the positioning arm 306, an anchor arm 360 positioned within the in-line collar 308 may be configured to angulate between about 0 degrees to about 30 degrees. In certain embodiments, an anchor arm 360 may be configured to angulate from a generally perpendicular orientation relative to an implant arm 362 about 5, 10, or 15 degrees.

Figure 14F:
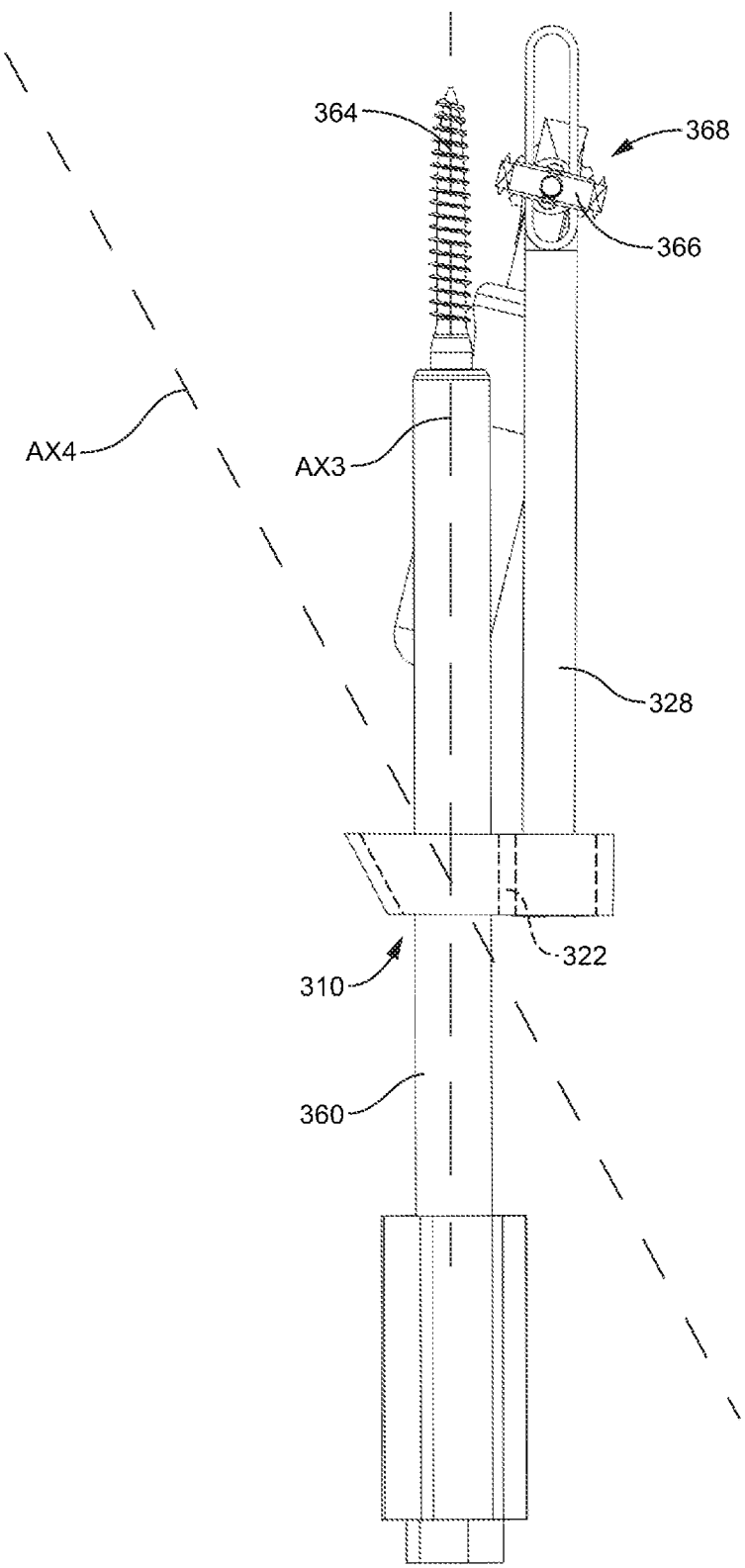
FIG. 14F is a bottom view of the positioning arm, implant arm, and anchor arm with the anchor arm positioned in an offset collar of the positioning arm.

Reference is now made to FIG. 14F, which is a bottom view of the positioning arm 306 with an anchor arm 360 coupled to the offset collar 310 of the positioning arm 306. As seen in the figure, the anchor arm 360 is positioned along an axis AX3 that is adjacent and generally parallel with the partition wall 322 and the positioning member 328 such that the anchor 364 is positioned lateral of the graft window 368 of the implant 366. In this orientation, the anchor 364 avoids contact with the implant 366 in all rotational orientations of the implant 366. Because of the sloped surfaces on the interior of the offset collar 310, the anchor arm 360 may pivot about the offset collar 310 and angulate away from implant 366 between axes AX3 and AX4, for example. While not illustrated in FIG. 14F, when the anchor arm 360 is positioned within the offset collar 310, the anchor arm 360 may angulate in the manner as described in reference to the in-line collar 308 in FIG. 14E, among other possible angulations. In this and other embodiments of the positioning arm 306, an anchor arm 360 positioned within the offset collar 310 may be configured to angulate between: about 0 degrees to about 30 degrees in a plane parallel to the positioning member 328; and about 0 degrees to about 30 degrees in a plane perpendicular to a plane parallel to the positioning member 328.

B. Curved Implants with Uni-Planar Rotation and Associated Delivery Tools

The following discussion will focus on FIGS. 15A-16D, which illustrate a delivery tool and implants that are configured for uni-planar rotation relative to the delivery tool. Because of the unique shape of the sacroiliac joint, an implant having a curved shape that generally matches the shape of the sacroiliac joint may be beneficial in a joint fusion, or other, procedure. To facilitate delivery of a curved implant, among other implants, into the sacroiliac joint, a delivery tool allowing for certain rotation of the implant relative to the delivery tool may be desirable.

Figure 15A:
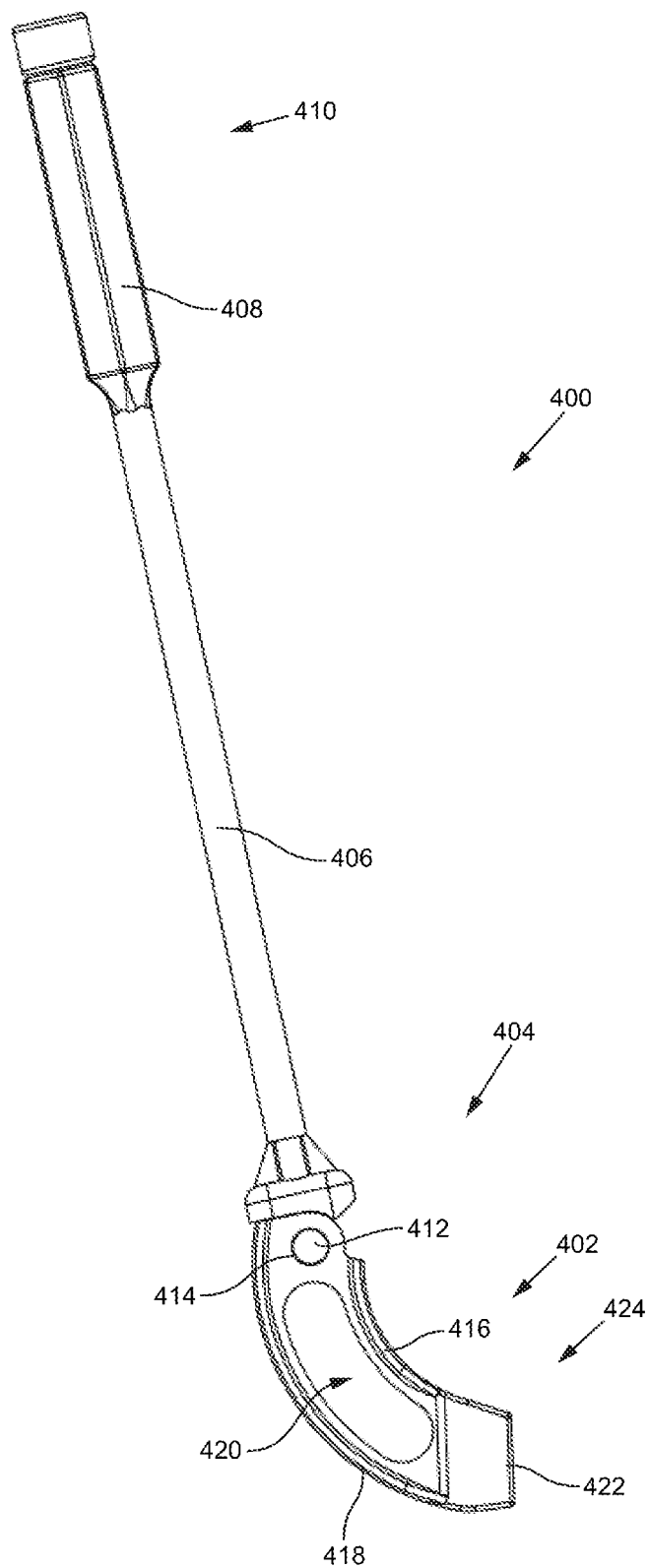
FIG. 15A is a side view of a delivery tool rotatably coupled with a curved implant.

As illustrated in FIG. 15A, which is a side view of a delivery tool 400, a curved implant 402 is coupled to a distal end 404 of the delivery tool 400. The delivery tool 400 includes a tubular shaft 406 extending proximally from the distal end 404 and includes a handle 408 at a proximal end 410 of the delivery tool 400. As seen in the figure, the implant 402 is rotationally coupled with the delivery tool 400 via a cylindrical insert 412 that is fitted within a transverse bore 414 to form a plain bearing for the implant 402 to rotate relative to the delivery tool 400. The implant 402 further includes an upper keel 416 separated from a lower keel 418 by a graft window 420 extending transversely or across the implant 402. In this embodiment, the upper and lower keels 416, 418 converge to form a distal tip 422; however, in other embodiments of the implant 402, a distal end 424 of the implant 402 may be opened with no convergence of the keels 416, 418.

Figure 15B:
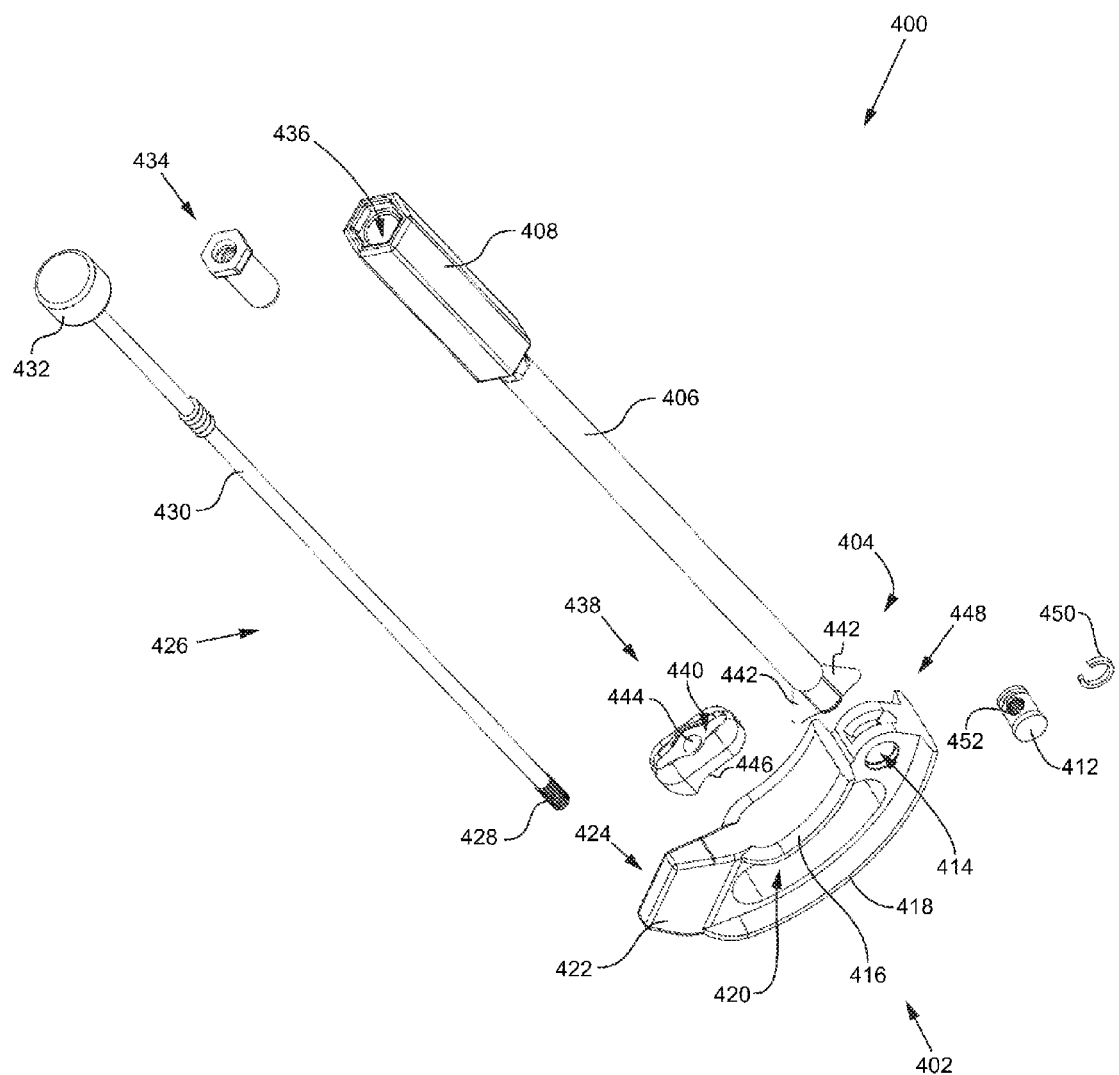
FIG. 15B is an isometric top and exploded view of the delivery tool and implant of FIG. 15A.
Figure 15C:
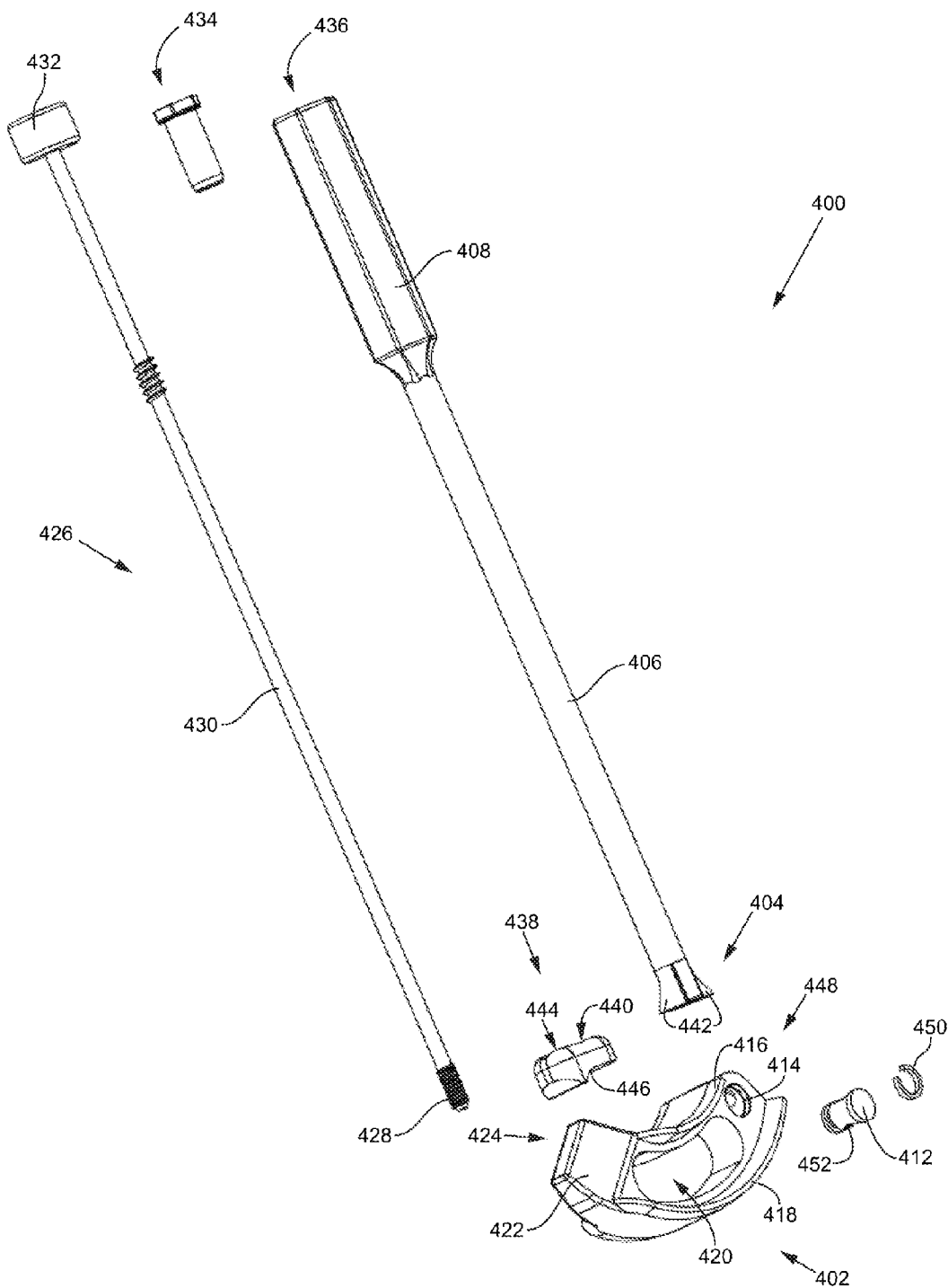
FIG. 15C is an isometric bottom and exploded view of the delivery tool and implant of FIG. 15A.

Referring to FIGS. 15B-15C, which are isometric top and bottom views of the delivery tool 400 in an exploded view, the remaining components of the delivery tool 400 are shown. More particularly, the delivery tool 400 further includes an implant retainer 426 having a threaded distal end 428, a shaft 430 extending proximally from the threaded distal end 428, and a proximal handle 432. The delivery tool 400 also includes a proximal insert 434 that is positioned within a proximal opening 436 of the handle 408.

Coupled between the distal end 402 of the delivery tool 400 and the implant 402 is a coupler 438 that includes a recess 440 on its top surface that matingly receives a pair of spreader members 442 on the distal end 404 of the delivery tool 400. As seen in the figures, the coupler 438 includes a bore 444 extending therethrough that is coaxially aligned with an internal passageway extending through the tubular shaft 406 when the spreader members 442 of the delivery tool 400 are matingly received in the recess 440 of the coupler 438. The bottom surface of the coupler 438 includes a curved bearing surface 446 that abuts against a proximal end 448 of the implant 402. As will be shown in later figures, the shape of the bottom surface of the coupler and the proximal end 448 of the implant are configured to limit the rotation of the implant 402.

In operation, once the proximal insert 434 is positioned within the proximal opening 436, the implant retainer 426 may be distally inserted into and through the tubular shaft 406 such that the threaded distal end 428 extends out a distal opening 448 of the tubular shaft 406. The coupler 438 may be engaged with the spreader members 442 and the threaded distal end 428 of the implant retainer 426 may extend through the bore 444. The cylindrical insert 412 may be positioned within the transverse bore 414 and a retainer ring 450 may secure the insert 412 within the bore 414. As seen in the figures, the cylindrical insert 412 includes a threaded bore 452 that is configured to threadably receive the threaded distal end 428 of the implant retainer 426 to thereby couple the implant 402 and the delivery tool 400.

Figure 15D:
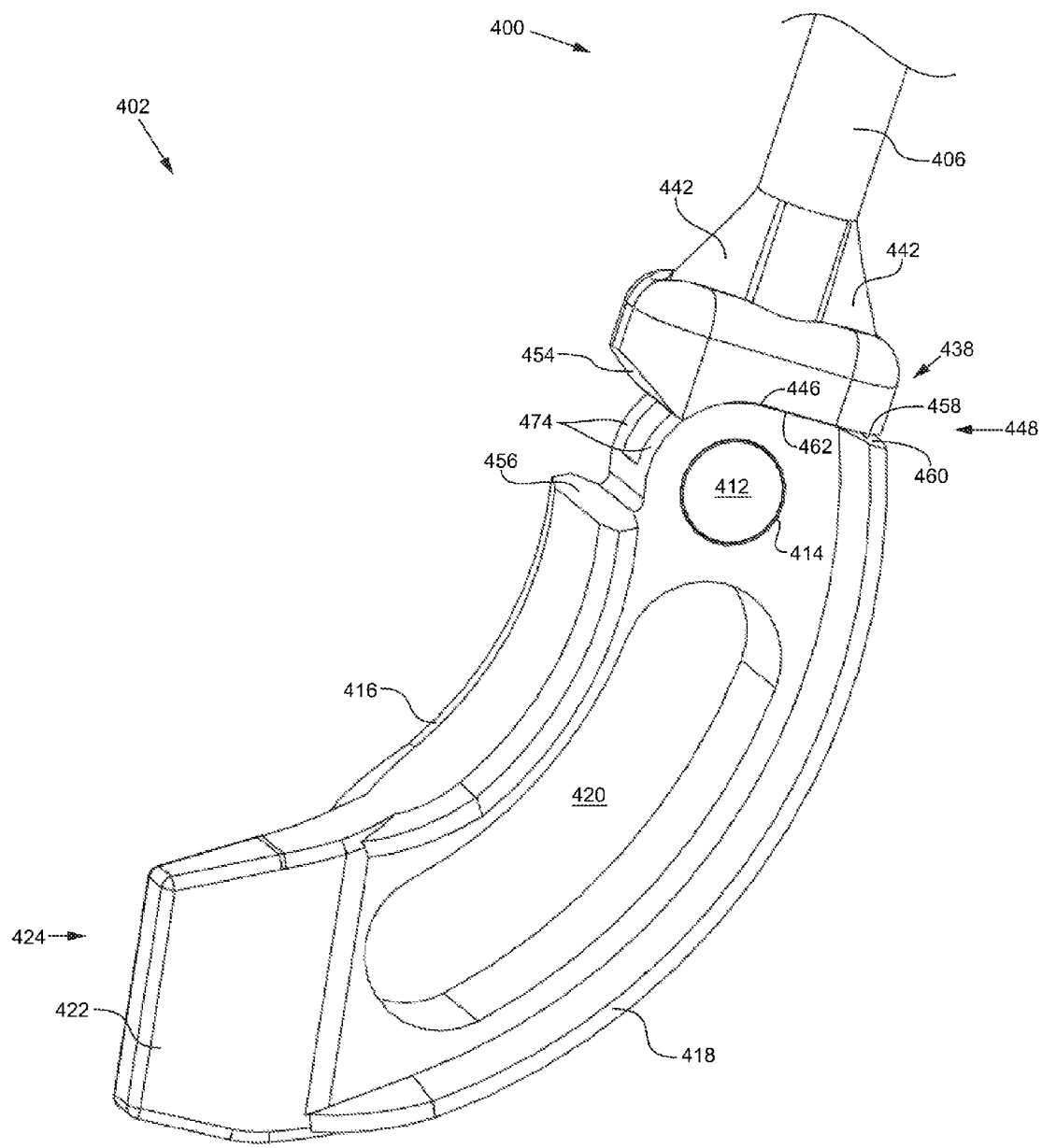
FIGS. 15D-15F are close-up views of the implant rotatably coupled with the delivery tool with the implant in various degrees of rotation relative to the delivery tool.
Figure 15E:
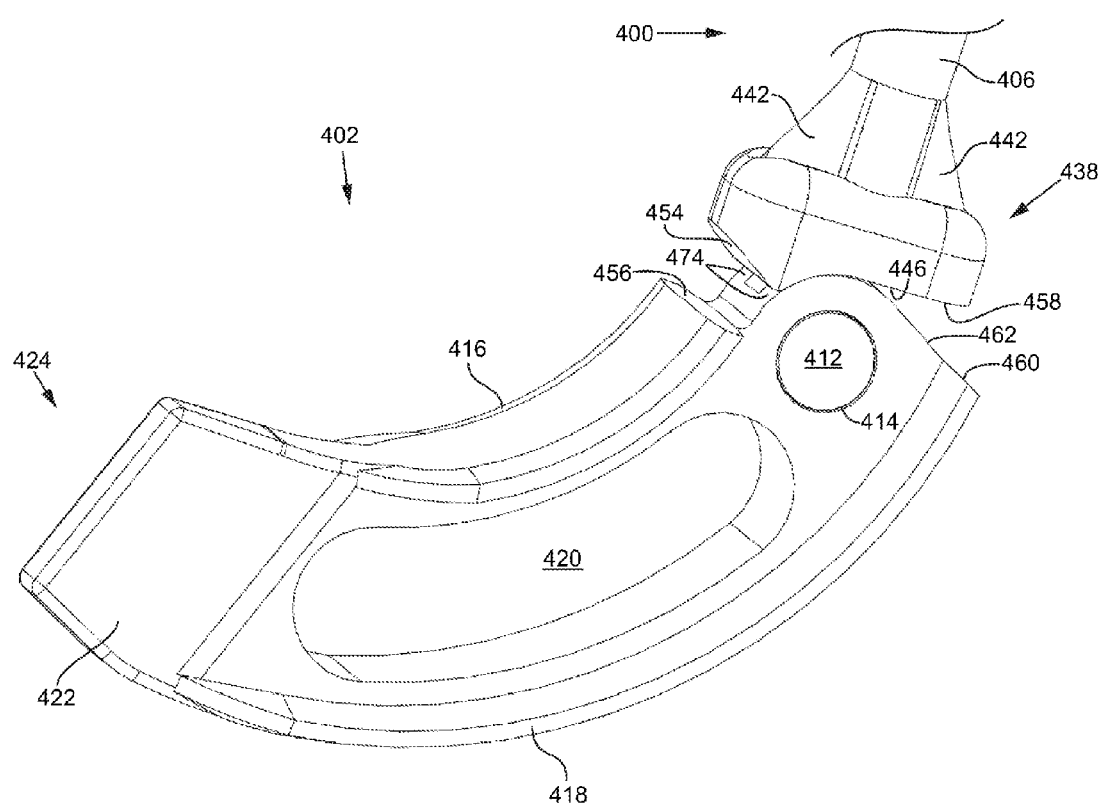
Figure 15F:
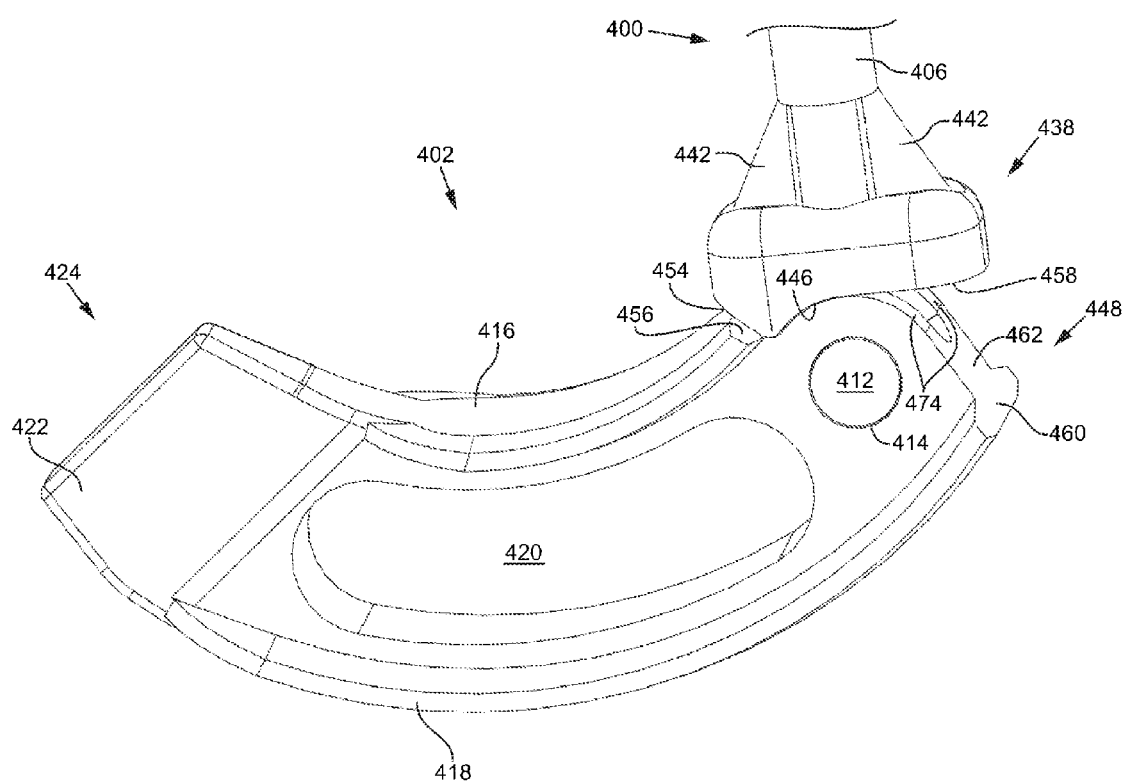

As illustrated in FIGS. 15D-15F, which are a close-up, isometric top views of the implant 402 coupled to the delivery tool 400 in different degrees of rotation, the curved bearing surface 446 of the coupler 438 matingly abuts against a proximal surface 462 of the proximal end 448 of the implant 402. The proximal surface 462 is defined on a proximal surface of each of a pair of bearing members 474. The pair of bearing members 474 includes a gap defined therebetween such that the threaded distal end 428 may extend through the gap to engage with the bore 452 of the cylindrical insert 412. As mentioned previously, the geometry of the bottom surface of the coupler 438 influences the amount of possible rotation of the implant 402 relative to the delivery tool 400. More particularly, in addition to the curved bearing surface 446, the bottom portion of the coupler 438 includes a first planar surface 454 that extends from the curved bearing surface 446. The first planar surface 454 acts as a stop feature and is configured to contact a proximal end surface 456 of the upper keel 416 when the implant 402 is rotated in a clockwise direction, as shown in FIGS. 15D-15F. Opposite the first planar surface 454 is a second planar surface 458 that also acts as a stop feature and is configured to contact a proximal end surface 460 of the lower keel 418 when the implant 402 is rotated in a counterclockwise direction, as shown in FIGS. 15D-15F. Thus, the total amount of rotation of the implant 402 relative to the delivery tool 400 is fixed between the first planar surface 454 contacting the proximal end surface 456 of the upper keel 416 and the second planar surface 458 contacting the proximal end surface 460 of the lower keel 418. As can be understood from the previous discussion, the same delivery tool 400 may be used with different couplers 438 (i.e., having differently shaped curved bottom surfaces and first and second planar surface 454, 458 arrangements) and corresponding implants 402 to facilitate different degrees of rotation between the implant 402 and the delivery tool 400. In this and other embodiments, the amount of rotation of the implant 402 relative to the delivery tool 400 may be between about 10 degrees and about 180 degrees. In certain embodiments, the rotation may be about 30, 50, or 90 degrees.

Figure 15G:
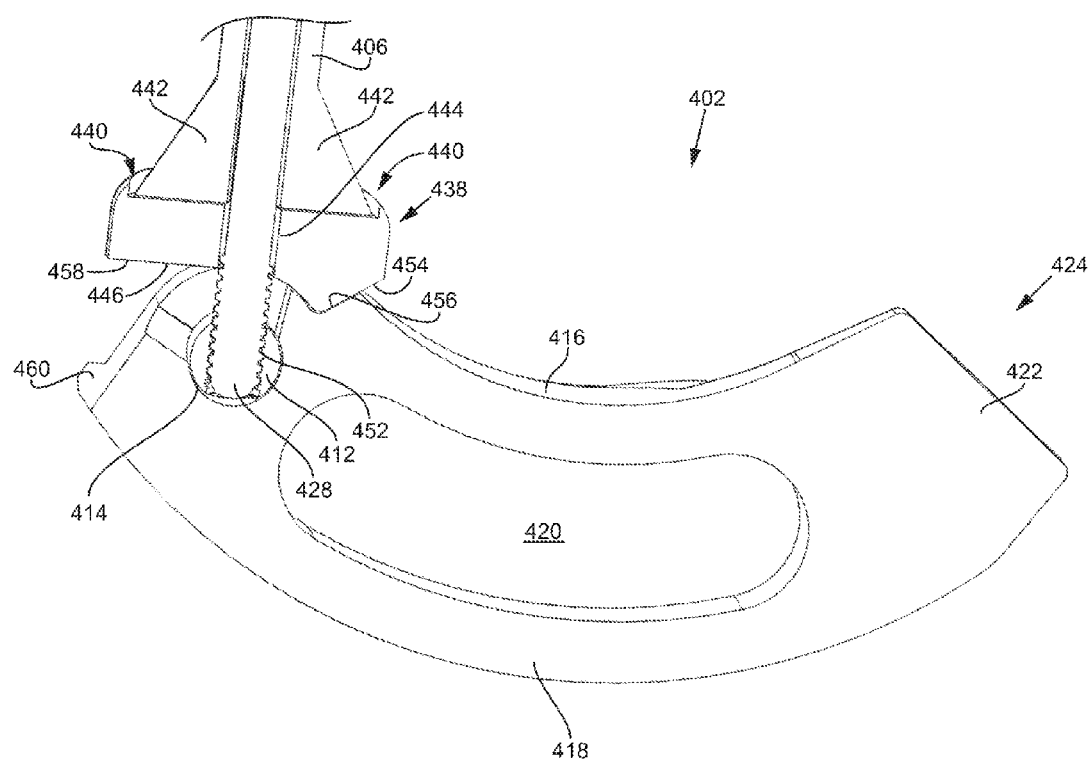
FIG. 15G is a side cross-sectional view of the implant rotatably coupled with the delivery tool with the cross-section along a longitudinal axis of the implant.
Figure 15H:
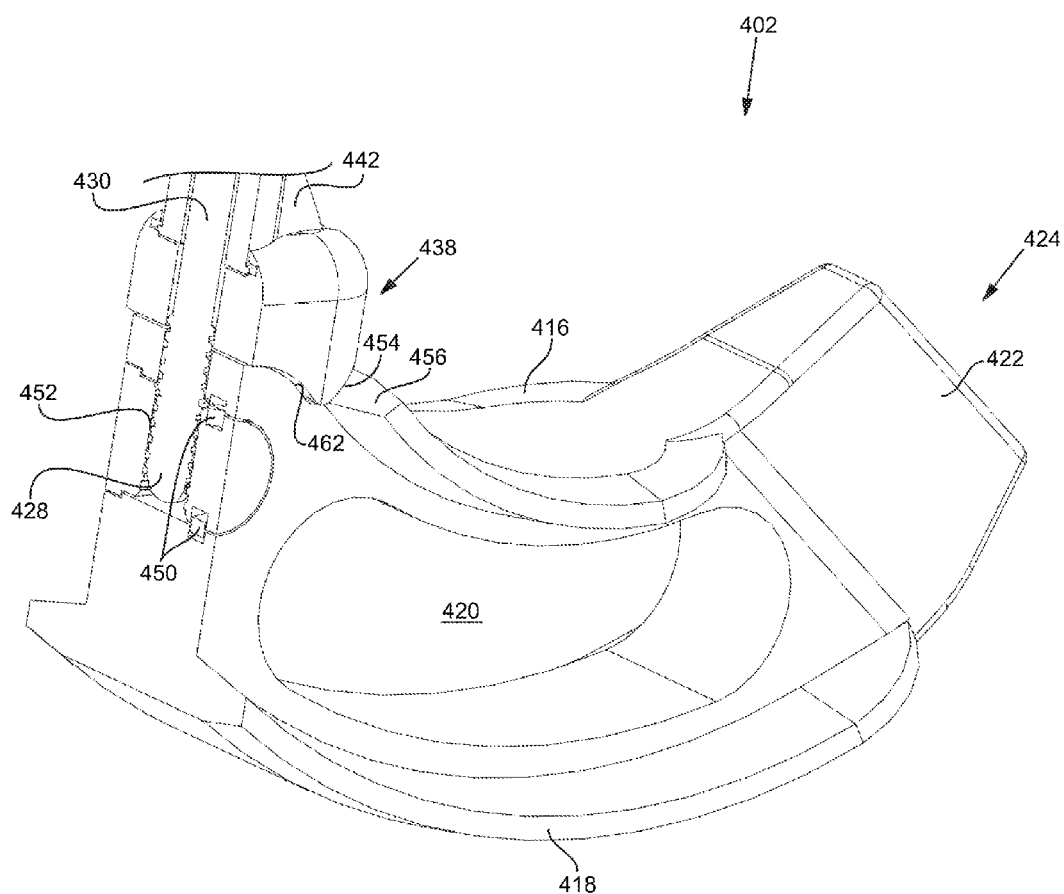
FIG. 15H is a side cross-sectional view of the implant rotatably coupled with the delivery tool with the cross-section along an axis perpendicular to the longitudinal axis of the implant.

Referring now to FIG. 15G, which is a cross-sectional view of FIG. 15F taken along a longitudinal axis of the implant 402, the first planar surface 454 abuts the proximal end surface 456 of the upper keel 416 such that further rotation is inhibited. As seen in the figure, the threaded distal end 428 extends through the tubular shaft 406 of the delivery tool 400 and through the bore 444 of the coupler 438 to threadably engage with the threaded bore 452 of the cylindrical insert 412. As seen in FIG. 15H, which is another cross-sectional view of FIG. 15F, except the cross-section in the present figure is perpendicular to the longitudinal axis of the implant 402 and bisecting the cylindrical insert 412, the retainer ring 450 supports a position of the cylindrical insert 412 within the implant 402 when before and after the implant retainer 426 is coupled with the insert 412.

Referring now another embodiment of an implant 402, reference is made to FIGS. 16A-16C. As seen in the figures, the implant 402 is similar to the implant 402 shown in FIGS. 15A-15E, except that the distal end 424 of the implant 402 includes an opening 464 such that the upper and lower keels 416, 418 are cantilevered off of the proximal end 448 of the implant 402 as opposed to coupled together by with a convergent distal tip. Additionally, the present embodiment of the implant 402 differs from that shown in FIGS. 15A-15E in that the proximal surface 462 of the proximal end 448 of the implant 402 allows for increased rotation of the implant 402 relative to the delivery tool 400 because the proximal surface 462 extends circumferentially further between the proximal end surface 456 of the upper keel 416 and the proximal end surface 460 of the lower keel 418. In this way, when the implant 402 is coupled with the delivery tool 400, the proximal surface 462 provides increased bearing contact with the curved bottom surface 446 of the coupler 438 such that the implant 402 can rotate further relative to the delivery tool 400 than in the previously described embodiment. In this and other embodiments, the amount of rotation of the implant 402 relative to the delivery tool 400 may be between about 10 degrees and about 200 degrees. In certain embodiments, the rotation may be about 30, 60, or 110 degrees.

As seen in FIG. 16C, which is a side view of the implant 402 shown in FIGS. 16A-16B, the upper and lower keels 416, 418 extend outwardly the proximal end 448 of the implant 402 and are separated by a rounded proximal wall 466. The keels 416, 418 are generally equidistant from each other from the rounded proximal wall 466 to their termination at the distal end 424 of the implant 402. As seen in FIGS. 16A-16C, inner and outer surfaces 468, 470 of the upper and lower keels 416, 418 are beveled along edges 472 that extend around the keels 416, 418. In the embodiment of FIGS. 16A-16C, the lower keel 418 extends a further distance, distally, from the rounded proximal wall 466 in order for the curvature of the top and bottom keels 416, 418 to match. In this and other embodiments, the curvature of the upper and lower keels 416, 418 are defined by an arc AR of about 80 degrees with a radius R1 of about 25 mm to 35 mm and a radius R2 of about 50 mm to 55 mm. In certain embodiments, the arc AR may be about 40, 50, 60, 70, 80, 90, 100, 110, or 120 degrees and may even be up to 180 degrees, radius R1 may be about 2, 2.5, 3 or 3.5 cm, and radius R2 may be about 4, 5, or 6 cm. A width of the keels may be about 1, 1.5, or 2 cm.

Figure 16D:
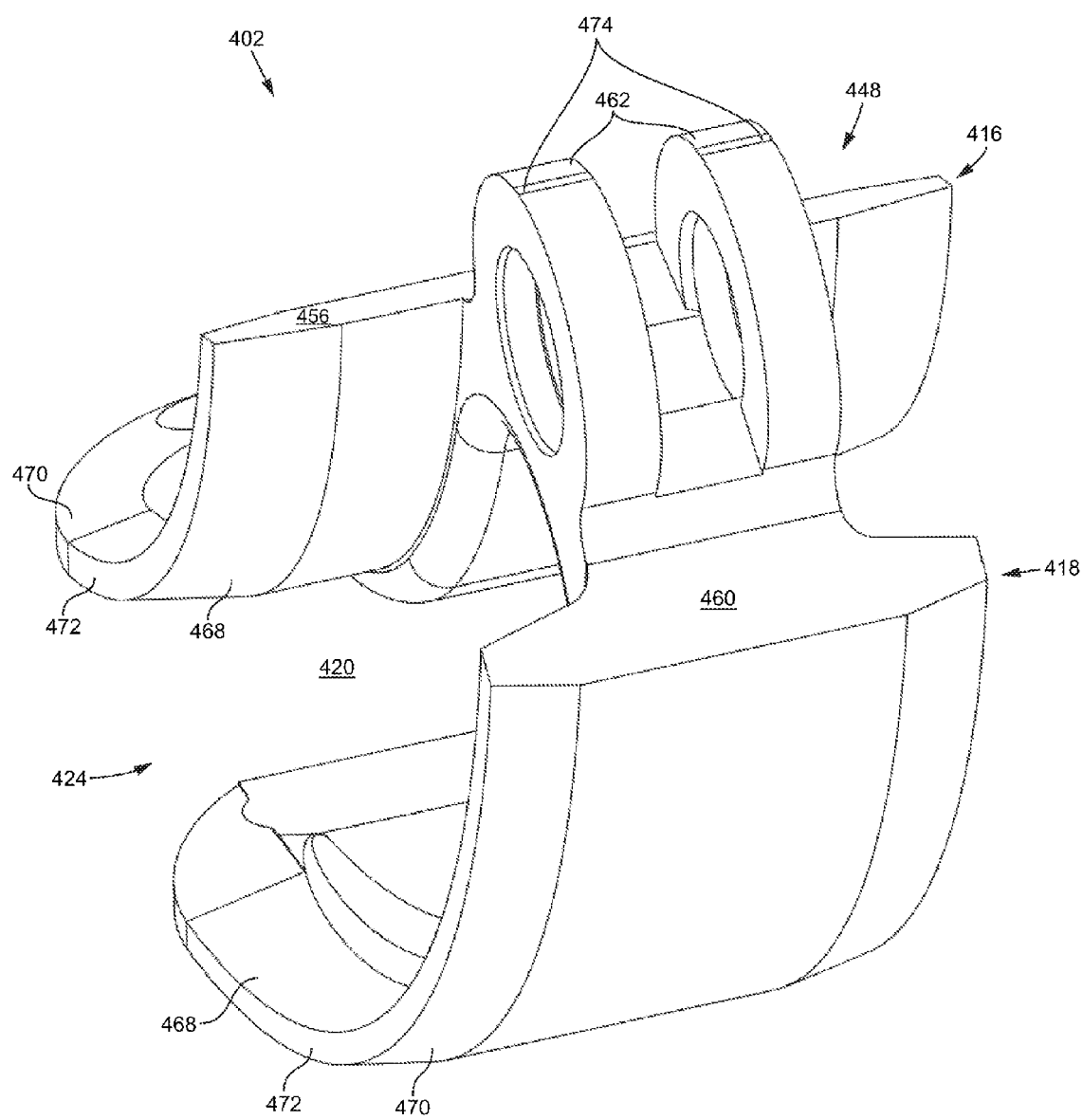
FIG. 16D is a back isometric view of the implant of FIG. 16A with wider upper keels and narrower lower keels.

While the keels 416, 418 of the implant 402 shown in FIGS. 16A-16C are of generally equal width, the upper and lower keels 416, 418 may be of different widths, as shown in FIG. 16D, which is an isometric view of the proximal end 448 of the implant 402. As seen in the figure, the upper keel 416 is wider than the lower keel 418. In certain embodiments, the upper keel 416 may be about 2 cm wide and the bottom keel 418 may be about 1 cm wide.

When implanted into a sacroiliac joint, the implant 402 is configured to extend non-transversely into the joint such that a portion of the upper keel 416 extends into the ilium and an opposite portion of the upper keel 416 extends into the sacrum. Similarly, a portion of the lower keel 418 extends into the ilium and an opposite portion of the lower keel 418 extends into the sacrum. In this way, the graft window 420 of the implant 402 lies within the plane of the joint such that bone growth may pass through the graft window 420, along with an anchor, to fuse the sacrum and ilium. In certain instances, it may be beneficial to deliver an implant having keels of different widths. And, since the sacrum and ilium are structurally thinner and generally less robust at the inferior boundary segment 3002, as seen in FIG. 11C, including an implant 402 with narrower keels at the bottom of the implant 402 may cause less material from the implant to extend into the sacrum and ilium along the thinner and less robust sections of the bones. In contrast, superior aspects of the sacrum and illium are thicker and more robust than portions of the sacrum and ilium at the inferior boundary segment 3002. Thus, the superior portions of the sacrum and ilium may be better suited to receive keels 416 that are relatively wider than keels 418 that are positioned near the inferior boundary segment 3002 of the joint.

C. Implants Having Angled and/or Asymmetrically Shaped End Caps

Figure 17A:
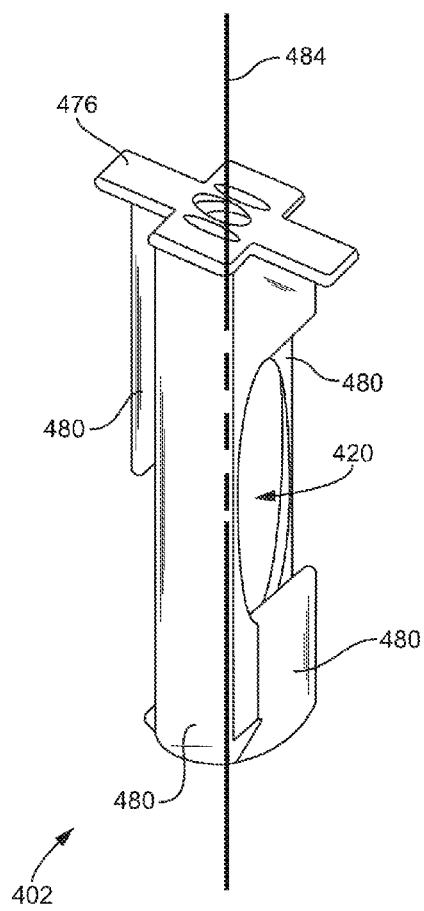
FIG. 17A is a side isometric view of a first embodiment of an implant with an angled end cap.
Figure 17B:
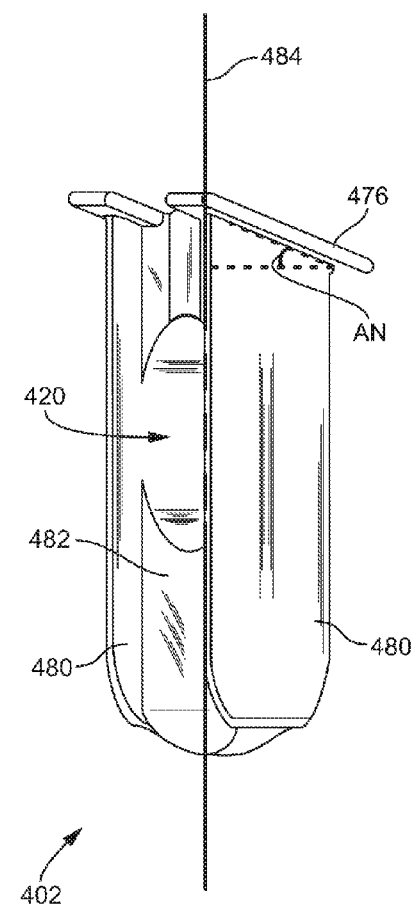
FIG. 17B is a side isometric view of a second embodiment of an implant with an angled end cap.
Figure 17C:
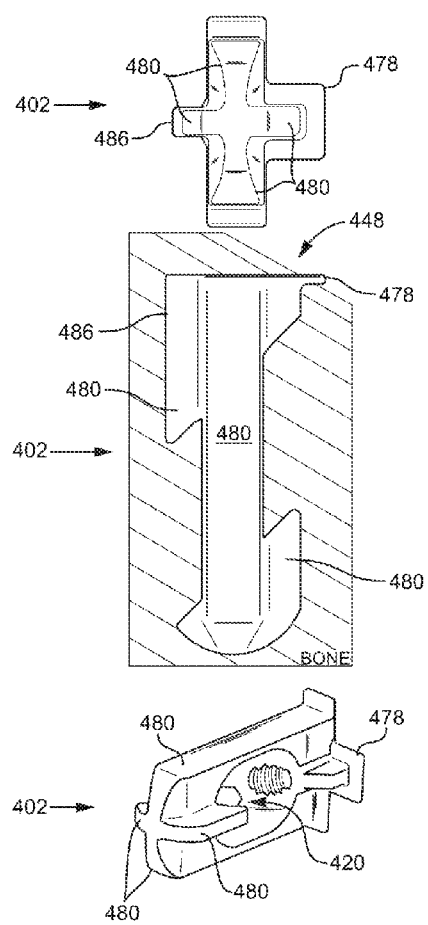
FIG. 17C is a series of views of a first embodiment of an implant with an asymmetric end cap.
Figure 17D:
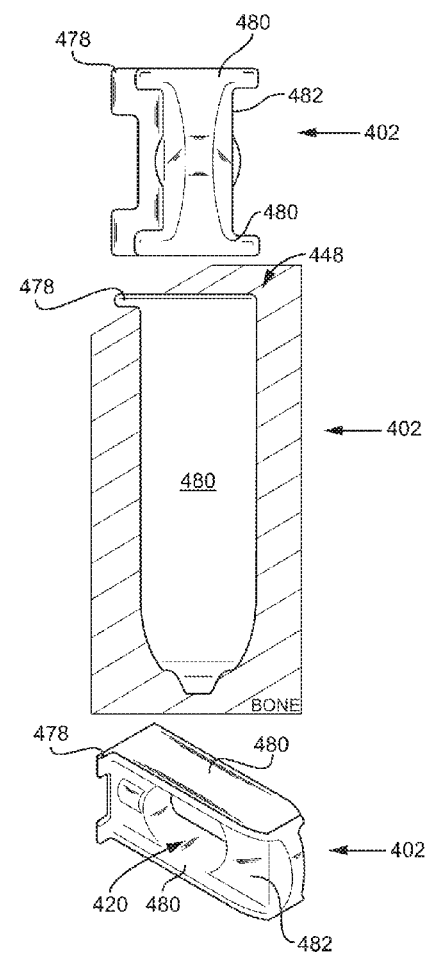
FIG. 17D is a series of views of a second embodiment of an implant with an asymmetric end cap.

Reference is now made to FIGS. 17A-17D, wherein FIGS. 17A-17B depict implants 402 with angled end caps 476 and FIGS. 17C-17D depict implants 402 with asymmetrically positioned end caps 478. First, reference is made to FIGS. 17A-17B. As seen in the FIG. 17A, the implant 402 includes a cross-shaped cross-section with a pair of keels 480 positioned generally perpendicular to each other. The implant 402 further includes a graft window 420 extending transversely across the implant 402 and intersecting the keels 480. As seen in FIG. 17B, the implant 402 includes a pair of keels 480 and a spanning member 482 extending between and generally perpendicular to the pair of keels 480. A graft window 420 extends transversely across the spanning member 482. In both embodiments of the implant 402, there is an angled end cap 476 that extends across the implant non-perpendicularly from a longitudinal axis 484 extending along a length of the implant 402. Such an orientation of an angled end cap 476 may be useful since, in certain instances, the sacroiliac joint is not perpendicularly aligned with the posterior surfaces of the sacrum and the ilium. As such, with an implant 402 having an angled end cap 476 that is non-perpendicularly aligned with the longitudinal axis 484 of the implant 402 may cause the end cap to lie flush with the posterior surfaces of the sacrum and the ilium. The angle AN, as seen in FIG. 17A, may be such that when the implant 402 is positioned non-transversely in the sacroiliac joint, the angled end cap 476 lies flush against the posterior surfaces of the sacrum and ilium. In certain embodiments, the angle AN may be about 15, 25, or 35, or be in a range of about 10 to about 50.

Reference is now made to FIGS. 17C-17D, which are the respective implants 402 shown in FIGS. 17A-17B, except the embodiments of the present discussion include asymmetrically positioned end caps 478. That is, the implants 402 include end caps 478 that do not extend over the entirety of the proximal end 448 of the implant 402. Instead, the end cap 478 only extends over a portion of the proximal end 448 of the implant. A purpose of the asymmetrically positioned end caps 478 is so that the end cap 478 will contact a posterior surface of either the sacrum or the ilium and, thus, prevent the implant 402 from further extending into the sacroiliac joint while allowing an opposite portion of the proximal end 448 of the implant to extend further into the joint.

As shown in FIG. 17C, the end cap 478 extends laterally over three of the four keels 480, but does not extend outward beyond a top surface 486 of one of the keels 480. As shown in FIG. 17D, the end cap 478 extends laterally from one half of the implant 402. In this way, when the implant 402, of either FIG. 17A or 17B, is delivered into the sacroiliac joint such that the graft window 420 is positioned within the plane of the joint such that an anchor may be received through the sacrum, ilium, and graft window 420, the asymmetrically positioned end cap 478 will inhibit further distal delivery of the implant 402 into the joint by the end cap 478 abutting either the posterior surface of the sacrum or ilium. It is noted that in the implants 402 of FIGS. 17A-17D, it may be desirable to utilize implants 402 that are specific to the procedure because the implants 402 cannot be rotated around the longitudinal axis 484 prior to implantation without changing the orientation of the angled or asymmetrically positioned end cap 478.

D. Curved Implants with Delivery Tooling Having a Gripping Implant Retainer

Figure 18A:
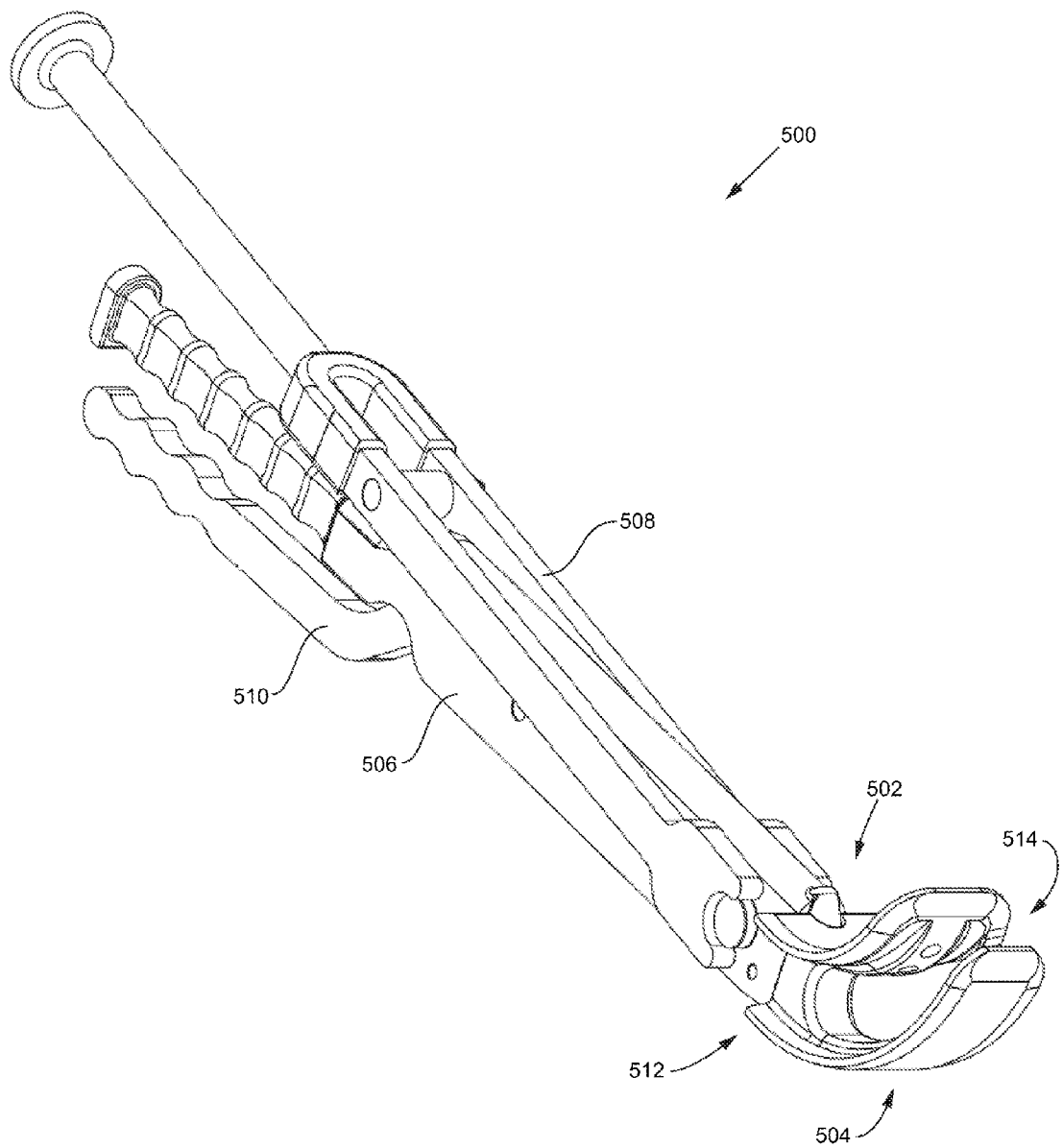
FIG. 18A is a front isometric view of a delivery tool coupled with an implant via a gripping mechanism.
Figure 18B:
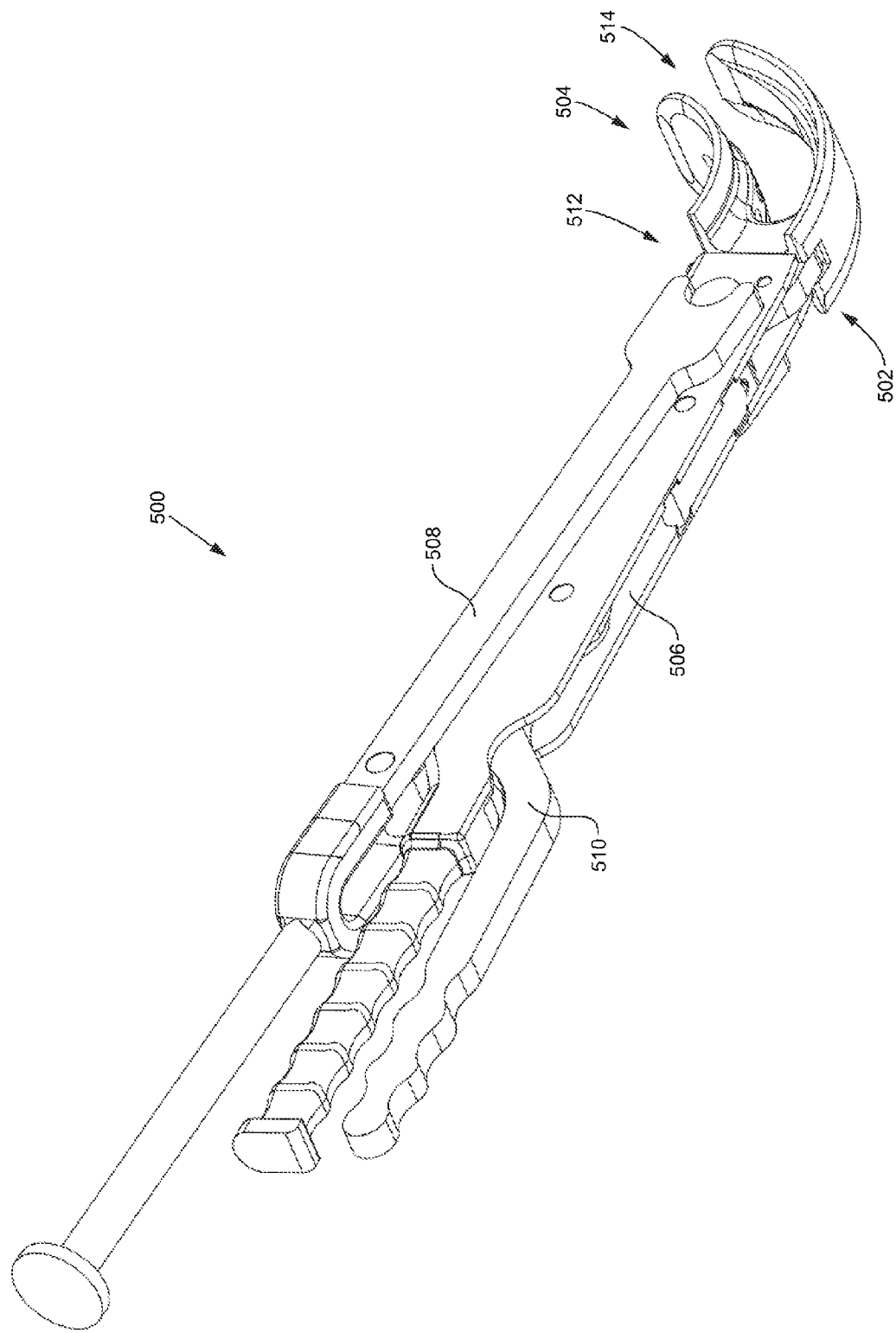
FIG. 18B is a back isometric view of the delivery tool and implant of FIG. 18A.

The following discussion will focus on FIGS. 18A-18L, which depict the various components of a delivery tool 500 having a gripping mechanism 502 coupling an implant 504 to the delivery tool 500. As illustrated in FIG. 18A-18B, which are respective front and back isometric views of the delivery tool 500, the tool 500 includes an implant arm 506, an impactor 508, and a lever assembly 510. The implant arm 506 and the lever assembly 510 work in conjunction with each other to grip a proximal end 512 of the implant 504. More particularly, the gripping mechanism 502 includes portions of the implant arm 506 and the lever assembly 510 that function to releasably couple with the implant 504. The implant 504 is curved along a longitudinal axis of the implant 504 and includes an opened distal end 514 as described previously with respect to FIGS. 16A-16D. This and other features of the implant 504 may be similar or different to previously described embodiments.

Figure 18C:
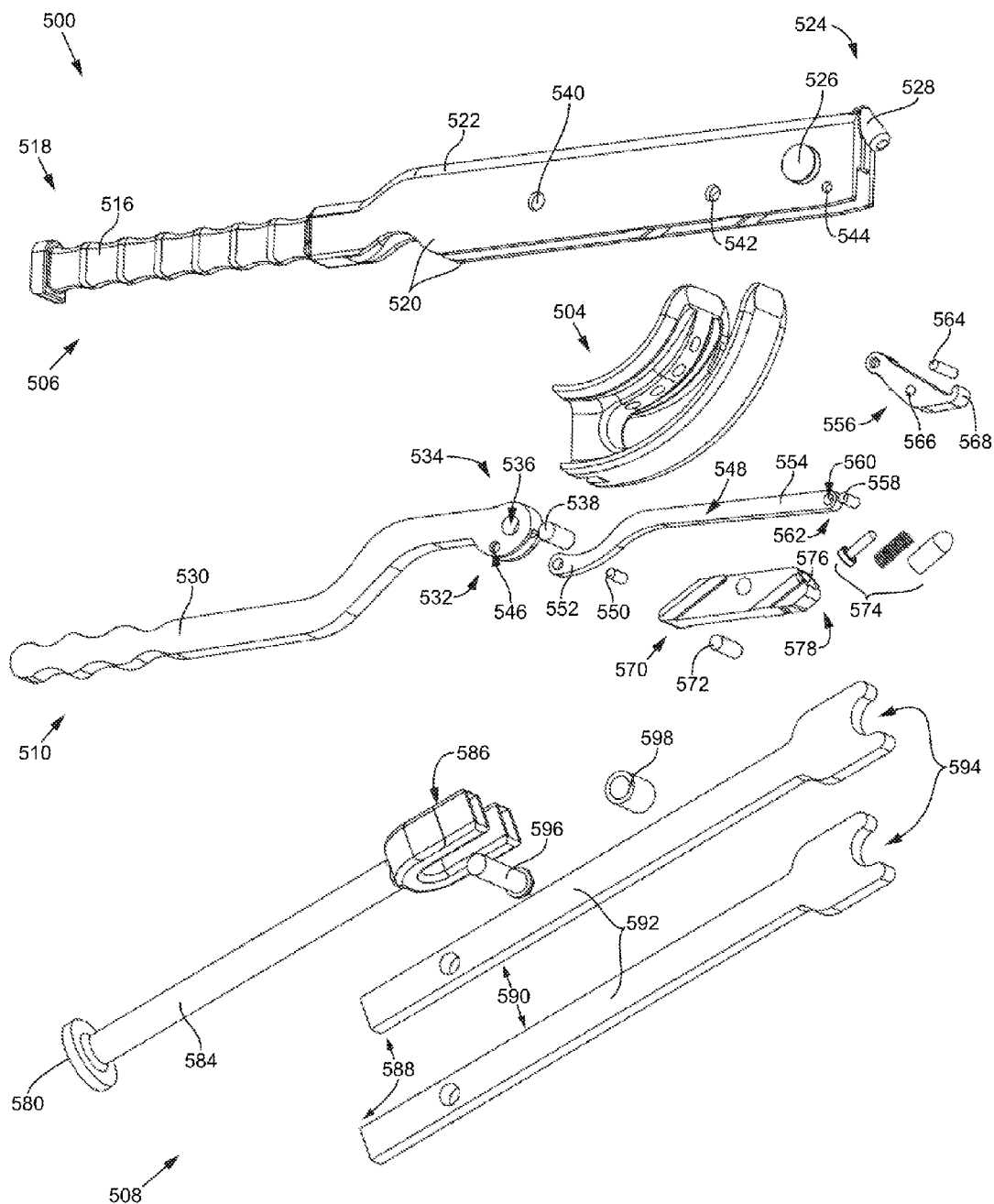
FIG. 18C is an isometric side and exploded view of the various components of the delivery tool and implant of FIG. 18A.
Figure 18D:
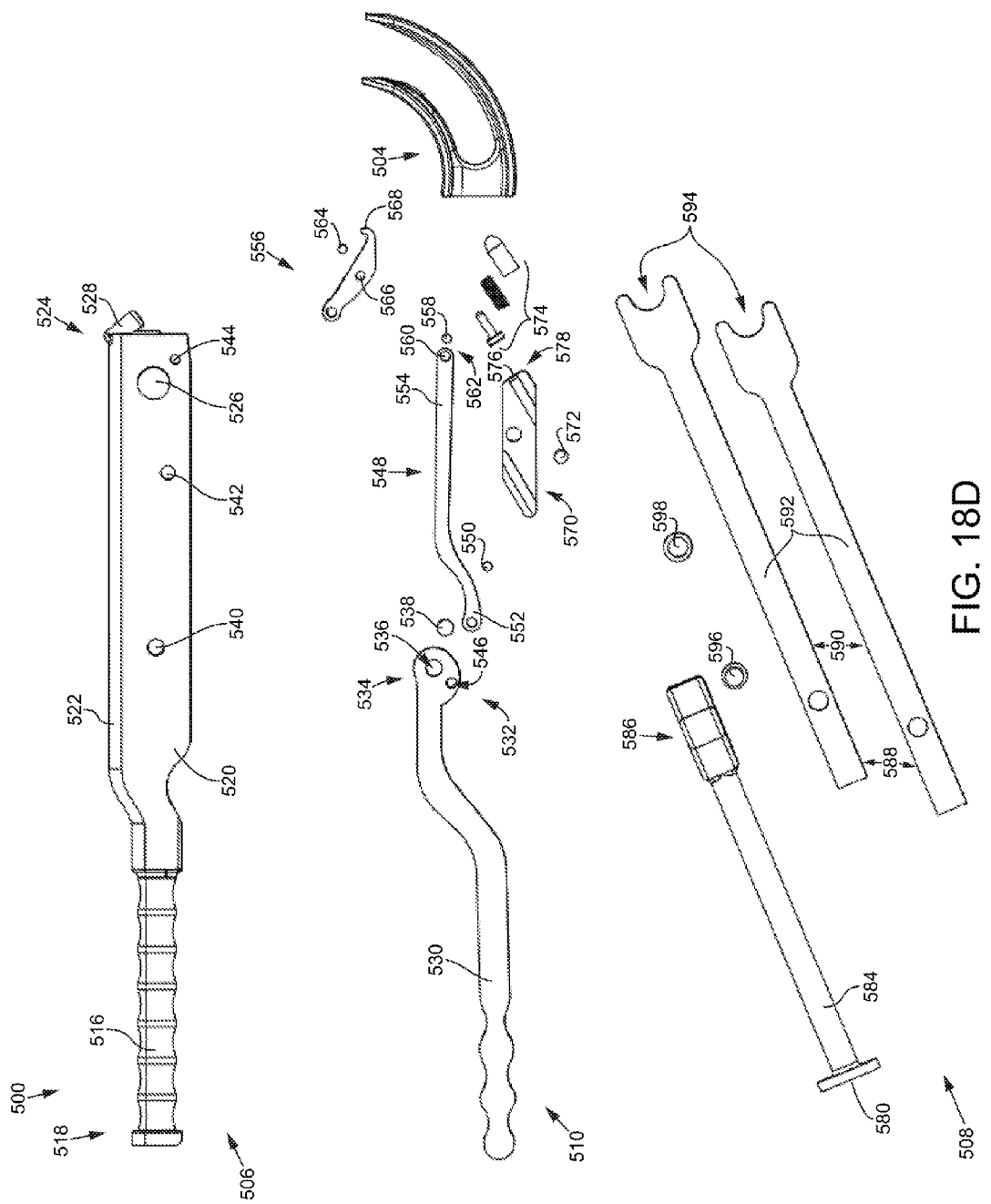
FIG. 18D is a side and exploded view of the various components of the delivery tool and implant of FIG. 18A.

Reference is now made to FIGS. 18C-18D, which are respective isometric side perspective and isometric side views of the delivery tool 500. Referring first to the implant arm 506, it includes a handle 516 at a proximal end 518 that is coupled to a pair of planar, plate-like members 520 that are coupled together by a top wall member 522. The plate-like members 520 and the top wall member 522 extend to a distal end 524 of the implant arm 506 and define an open interior space that houses a portion of the lever mechanism 510. The plate-like members 520 include a first, second, and third through holes 540, 542, 544 extending transversely across the plate-like member 520 and are configured to rotatably couple portions of the lever mechanism 510, as will be subsequently described. Near the distal end 524 of the implant arm 506 and extending outwardly from the plate-like members 520 are a pair of cylindrical protrusions 526 that are configured to be engaged with the impactor 508 to distally drive the delivery tool 500 and, thus, the implant 504 into a joint. At the extreme distal end 524 of the implant arm 506 is a fixed retainer member 528 that is cylindrically-shaped, although other shapes are possible for the fixed retainer member 528. Additionally, the fixed retainer member 528 may articulate, in which case the member would not be fixed. Continuing on, the fixed retainer member 528 is configured to be matingly received within a reciprocally shaped cavity in the proximal end 512 of the implant. The fixed retainer member 528 is a part of the gripping mechanism 502 and will be subsequently discussed in more detail.

Moving on to the lever mechanism 510, the mechanism includes a lever handle 530 that includes a cramming head 532 at a distal end 534 of the lever handle 530. The camming head 532 includes a first axle bore 536 extending generally through a central portion of the camming head 532. The camming head 532 is rotatably coupled to the implant arm 506 by a first shaft 538 (e.g., pin, rod, rivet) that extends through the first axle bore 536 and through the first through hole 540 to anchor the lever handle 530 to the implant arm 506. The camming head 532 further includes a second axle bore 546 positioned proximal-inferior of the first axle bore 536. The camming head 532 is rotatably coupled to a distal lever member 548 by a second shaft 550 extending through the second axle bore 546 in the camming head 532 and a through hole in the distal lever member 548. The distal lever member 548 includes a curved proximal section 552 and a straight distal section 554 that is rotatably coupled to a gripper member 556 by a third shaft 558 extending through a third axle bore 560 at the distal end 562 of the straight distal section 554 and a through hole on the gripper member 556.

The gripper member 556 is pivotally coupled to the implant arm 506 at the third through hole 544 by a fourth shaft 564 extending through a fourth axle bore 566 positioned in a central portion of the gripper member 556. The gripper member 556 includes a distal lip 568 that is configured to grip the proximal end 512 of the implant 504. In this way, translation of the distal lever member 548 causes the gripper member 556 to pivot about the fourth shaft 564 and, thus, pivot the distal lip 558 in a gripping motion to engage the proximal end 512 of the implant 504.

Positioned within the implant arm 506 is a lever retaining member 570 that is anchored to the second through hole 542 in the implant arm 506 via a fifth shaft 572. The lever retaining member 570 is positioned inferior of the straight distal section 554 of the distal lever member 548 and is configured to maintain a level orientation of the distal lever member 548 when the lever handle 530 is rotated about the first shaft 538. The level retaining member 570 includes a spring-biased pin 574 that is positioned in a recess 576 near a distal end 578 of the member 570 and is configured to support the straight distal section 554 in the level orientation.

Reference is now made to the impactor 508 in FIGS. 18C-18D. As seen in the figures, the impactor 508 includes an impact plate 580 at a proximal end 582 of the impactor 508. Moving distally from the impact plate 580 is a shaft 584 that couples to a tubular U-shaped member 586. A proximal portion 588 of impacting arms 590 are configured to be positioned within and secured to the U-shaped members 586. The impacting arms 590 include a shaft 592 that extends distally and terminates in a semi-circular bearing surface 594 that is configured to contact the cylindrical protrusions 526 on the implant arm 506. The impactor 508 also includes a sixth shaft 596 and a spacer 598 that couples between the pair of impacting arms 590 near the proximal portion 588 of the impacting arms 590.

Figure 18E:
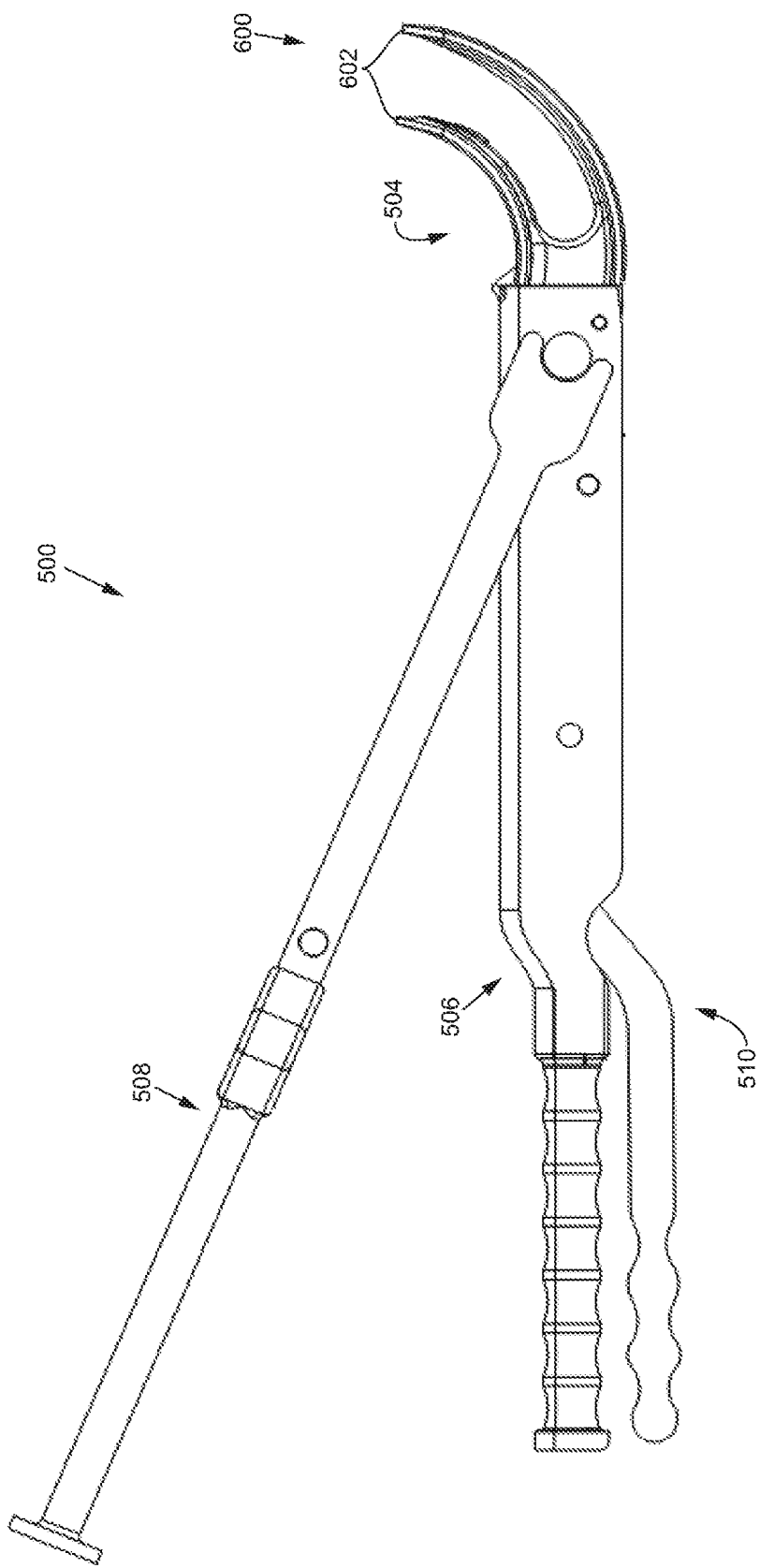
FIG. 18E is a side view of the delivery tool and implant of FIG. 18A with an impactor positioned superior of an implant arm.
Figure 18F:
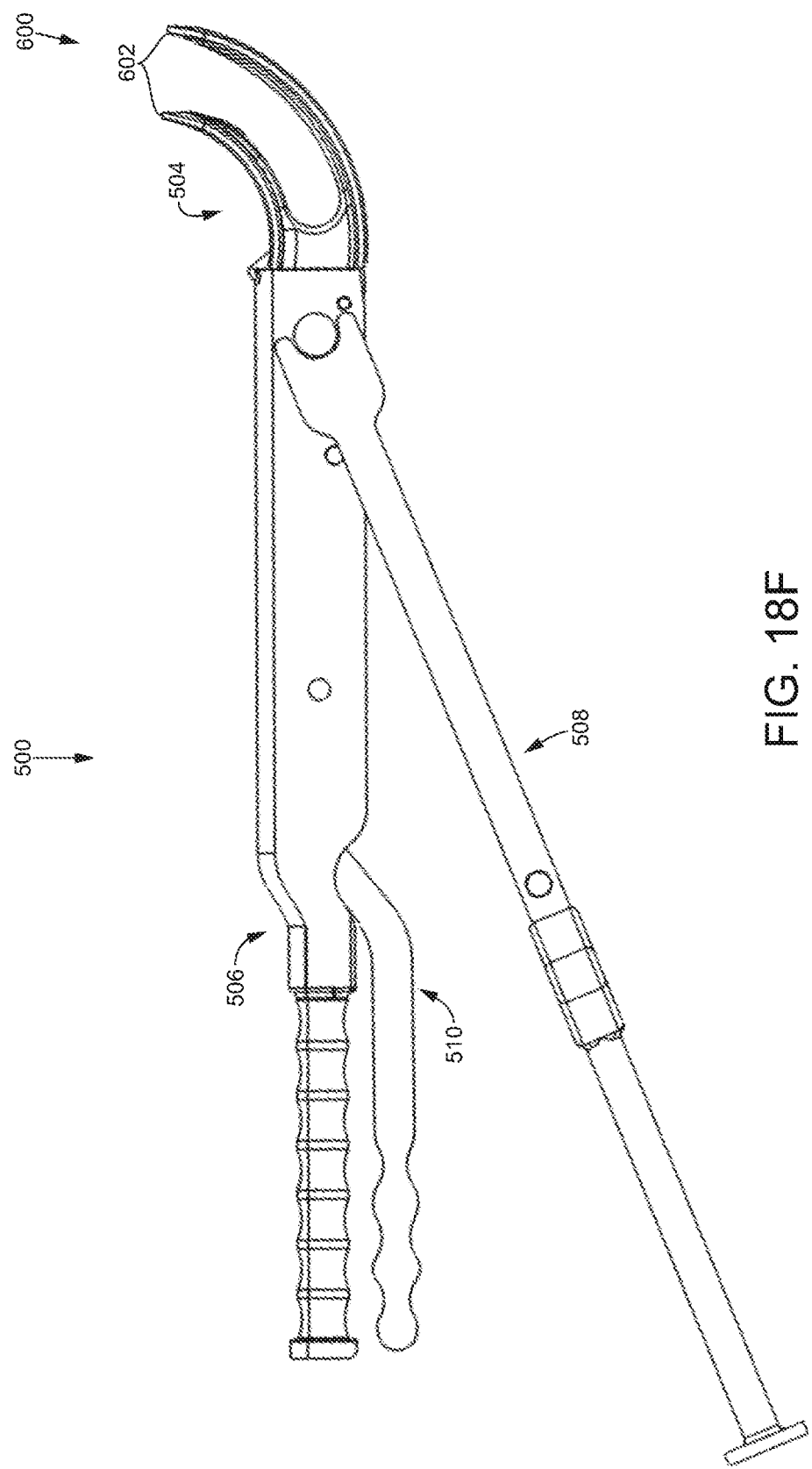
FIG. 18F is a side view of the delivery tool and implant of FIG. 18A with an impactor positioned inferior of the implant arm.

Turning now to FIGS. 18E-18F, which are side views of the delivery tool 500, the impactor 508 is positioned in various orientations relative to the implant arm 506. More particularly, in FIG. 18E, the impactor 508 is shown in a superior position relative to the implant arm 506, and, in FIG. 18F, the impactor 508 is shown in an inferior position relative to the implant arm 506. As seen in the figures, the impactor 508 may be used in these and other orientations to assist in driving the implant 504 into a patient's joint. For example, upon initial delivery of the distal end 600 of the implant into the joint, the surgeon may place the impactor 508 in an inferior position, as in FIG. 18F, because the impactor 508 is then in line with a trajectory of the distal tips 602 as they enter the joint. At other points in a surgical procedure, the surgeon utilize the impactor 508 in the superior position, as in FIG. 18E.

Figure 18G:
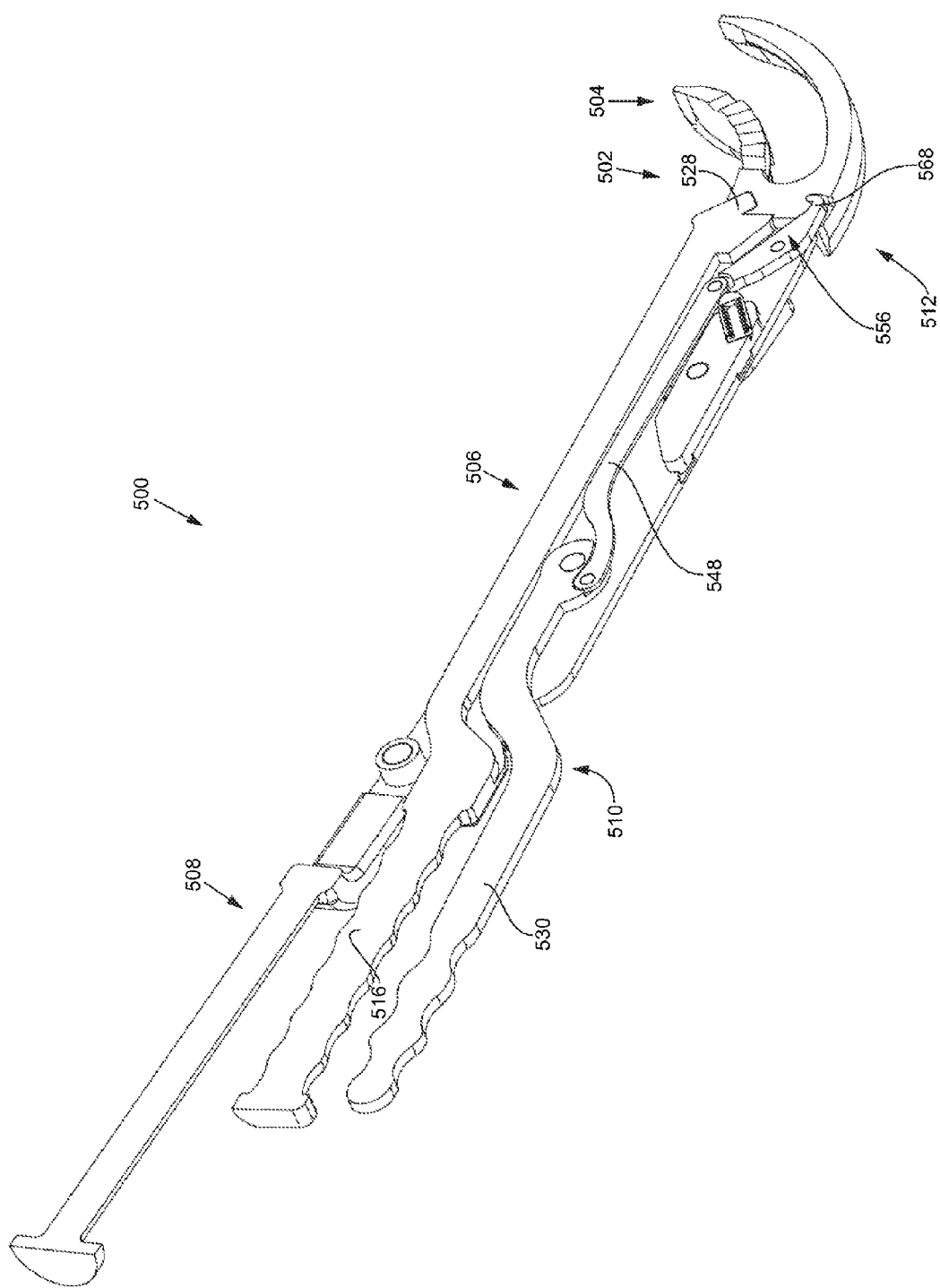
FIG. 18G is a side isometric and cross-sectional view of the delivery tool and implant where the cross-section is along a longitudinal axis of the delivery tool and implant and where the lever handle is in a closed position.

Reference is now made to FIG. 18G, which is an isometric side view of the delivery tool 500 with a cross section down a longitudinal axis of the tool 500. As seen in the figure, the implant 504 is locked within the gripping mechanism 502 by complementary action of the fixed retainer member 528 and the distal lip 568 of the gripping member 556. In this locked position, the lever handle 530 is generally parallel to the handle 516 of the implant arm 506, the distal lever member 548 is in a proximal-most position, and the gripping member 556 is pivoted in a counterclockwise-most direction to cause the distal lip 568 to retain the proximal end 512 of the implant 504 in abutting contact with the delivery tool 500.

Figure 18H:
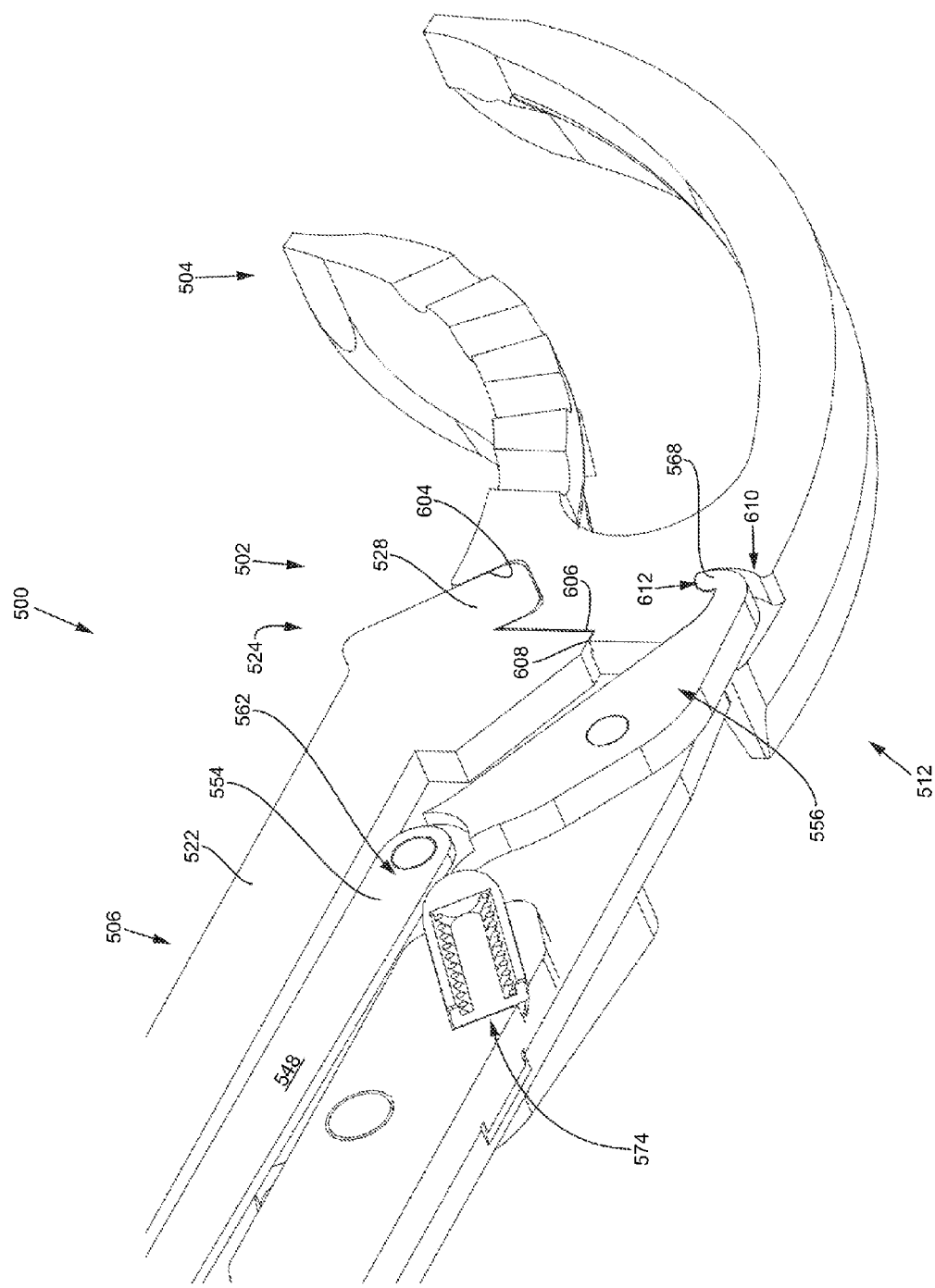
FIG. 18H is a close-up view of the gripping mechanism shown in FIG. 18G.

As seen in FIG. 18H, which is a close-up view of the gripping mechanism 102 shown in FIG. 18G, the implant 504 includes a cylindrically shaped recess 604 on a top portion of the proximal end 512 of the implant 504 that is configured to receive the fixed retaining member 528. The cylindrically shaped recess 604 extends into the proximal end 512 of the implant 504 at an approximate 45 degree angle. Inferior to the cylindrically shaped recess 604 is a notch 606 that is configured to receive a corresponding corner edge 608 of the distal end 524 of the implant arm 506. At a bottom portion of the proximal end 512 of the implant 504 is an elongated recess 610 having a superiorly and proximally extending terminal end 612. In this way, the distal lip 568 of the gripping mechanism 556 may extend in the elongated recess 610 and grasp the superiorly and proximally extending terminal end 612 upon closure of the lever handle 530, which causes counterclockwise pivoting of the gripping member 556 and gripping of the implant 504. Also, as shown in FIG. 18H, the spring-biased pin 574 urges the distal end 562 of the straight distal section 554 into a parallel orientation with the top wall 522 of the implant arm 506. The spring-biased pin 574 may also function as a stop feature to inhibit further counterclockwise pivoting of the gripping member 556.

Figure 18I:
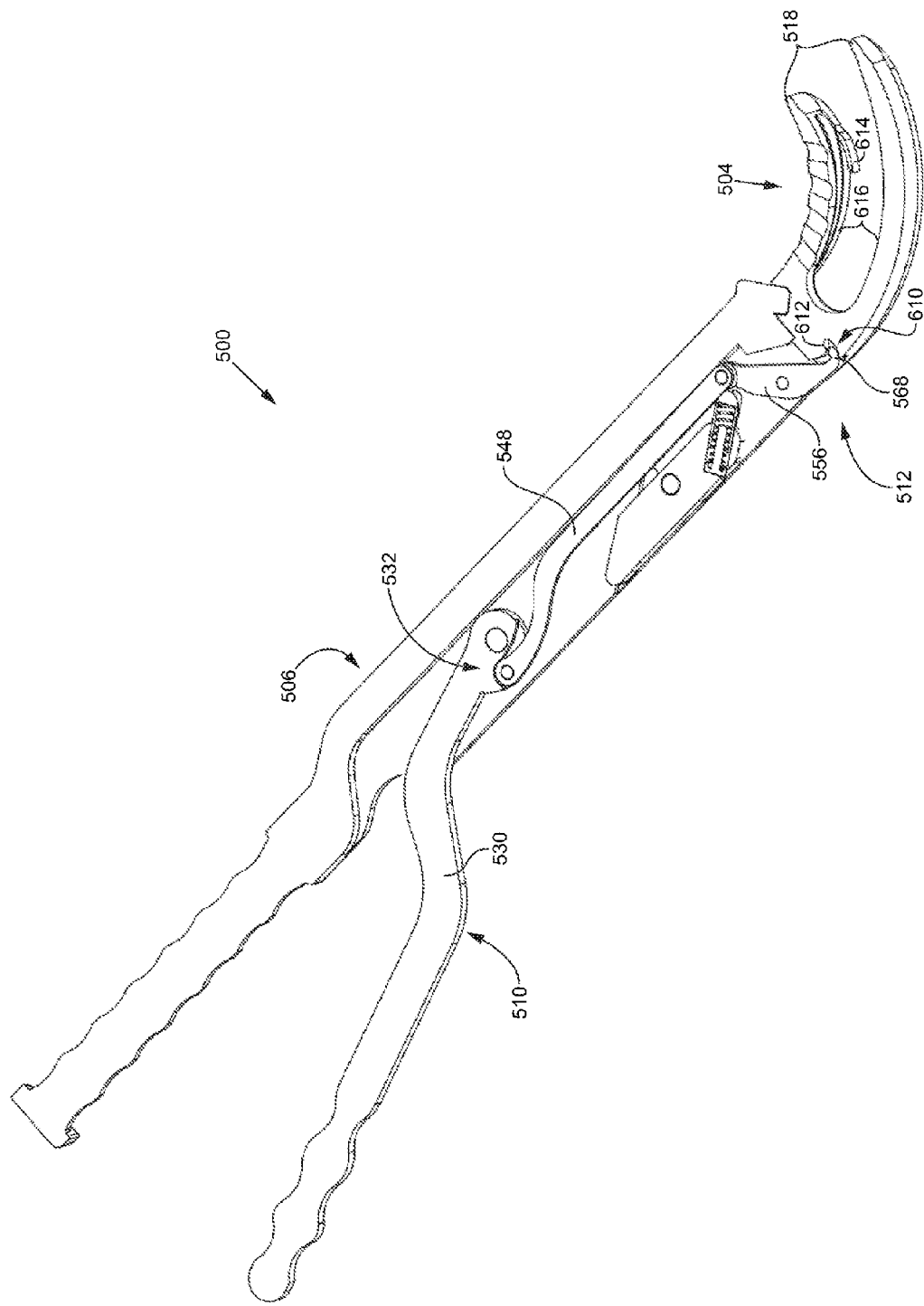
FIG. 18I is a side isometric and cross-sectional view of the delivery tool and implant where the cross-section is along a longitudinal axis of the delivery tool and implant and where the lever handle is in an opened position.

Referring now to FIG. 18I, which depicts a cross-sectional side view of the delivery tool 500, the lever handle 530 is opened by counterclockwise rotation of the lever handle 530. As seen in the figure, as the lever handle 530 is rotated, the camming head 532 rotates, which causes the distal lever member 548 to translate distally. The distal movement of the distal lever member 548 causes the gripping member 556 to pivot clockwise and, thus, release the distal lip 568 from its grip on the terminal end 612 of the elongated recess 610 on the bottom portion of the proximal end 512 of the implant 504.

Figure 18J:
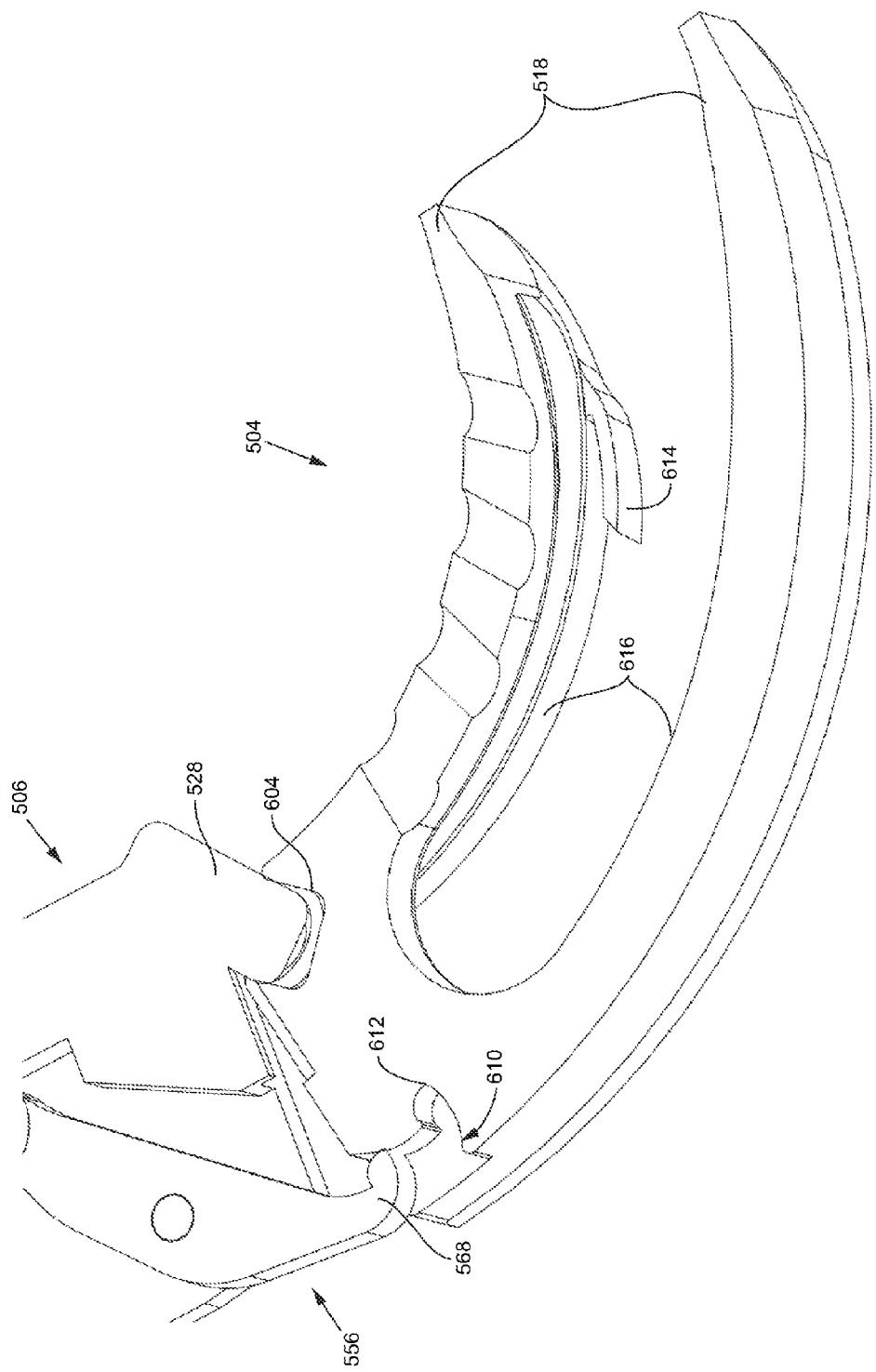
FIG. 18J is a close-up view of the implant coupled with the delivery tool shown in FIG. 18I.
Figure 18L:
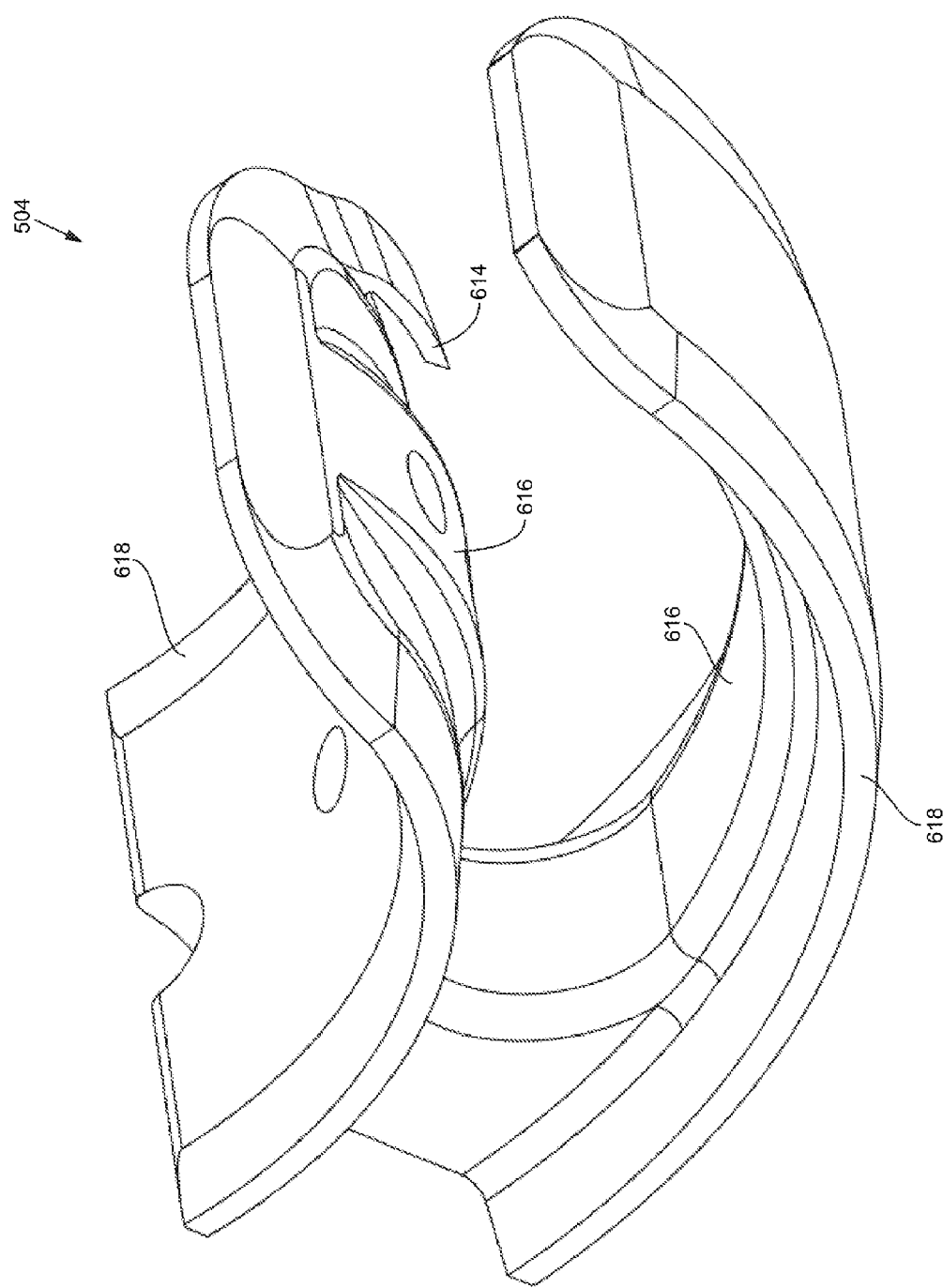
FIG. 18L is an isometric front view of the implant showing an anti-migration element.

As the distal lip 568 further releases from the elongated recess 610, as seen in FIG. 18J, the implant 504 pivots relative to the distal end 524 of the implant arm 506 to release the fixed retainer member 528 from engagement with the cylindrical recess 604. As the implant 504 is fully released from coupling with the gripping mechanism 102, as shown in FIG. 18K, the lever handle 530 is in a fully opened position. The delivery tool 500 is then ready to releasably couple with the implant 504, if desired, by positioning the fixed retainer member 528 within the cylindrical recess 604 of the proximal end 512 of the implant 504 and closing the lever handle (i.e., clockwise rotation), which will cause the distal lip 568 of the gripper mechanism 556 to pivot counterclockwise and grip the superiorly and proximally extending terminal end 612 of the elongated recess 610 of the implant 504. At that point, the impactor 508 (not shown) may be used and positioned in a superior or inferior position relative to the implant arm 506.

As illustrated in FIGS. 18I-18L, the implant 504 may include anti-migration elements 614 on inner walls 616 of the keels 618. The anti-migration elements 614 may include ramped structures, surface deformities, or any other feature to inhibit proximal, or other, migration of the implant 504 once implanted into the joint. Multiple anti-migration elements 614 may positioned on the inner walls 616 of the keels 618. Additionally, the anti-migration elements 614 may be positioned on outer walls of the keels 618 or on the outer and inner walls 616 of the keels 618.

E. Alternative Implant Embodiments

Reference is now made to FIGS. 19A-19F, which depict various views of an implant 700 for use with delivery tools described herein, among other delivery tools. Initially referring to FIGS. 19A-19B, which are respective isometric top and bottom views of the implant 700, the implant 700 includes a top planar keel member 702 and a bottom planar keel member 704 that are coupled together at a proximal end 706 of the implant 700 by a tubular member 708 defining a bore 710 therein. The top planar keel member 702 includes a sacrum section 712 and an ilium section 714 that are separated by an elastically deformable structural element 716. Similarly, the bottom planar keel member 704 includes a sacrum section 718 and an ilium section 720 that is separated by an elastically deformable structural element 722. In this or other embodiments, the structural elements 716, 722 may be inelastically deformable.

Figure 19A:
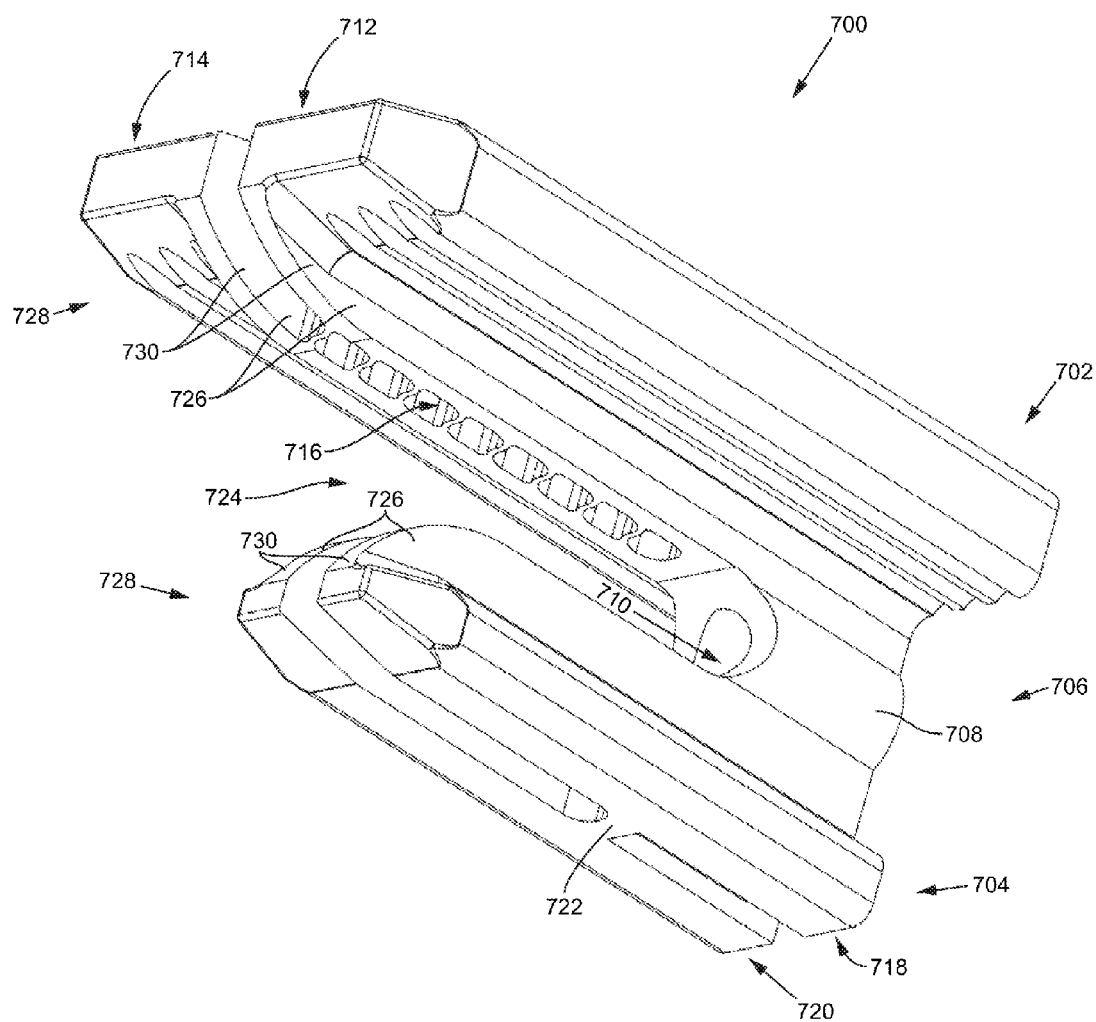
FIG. 19A is an isometric front and bottom view of another implant embodiment.
Figure 19B:
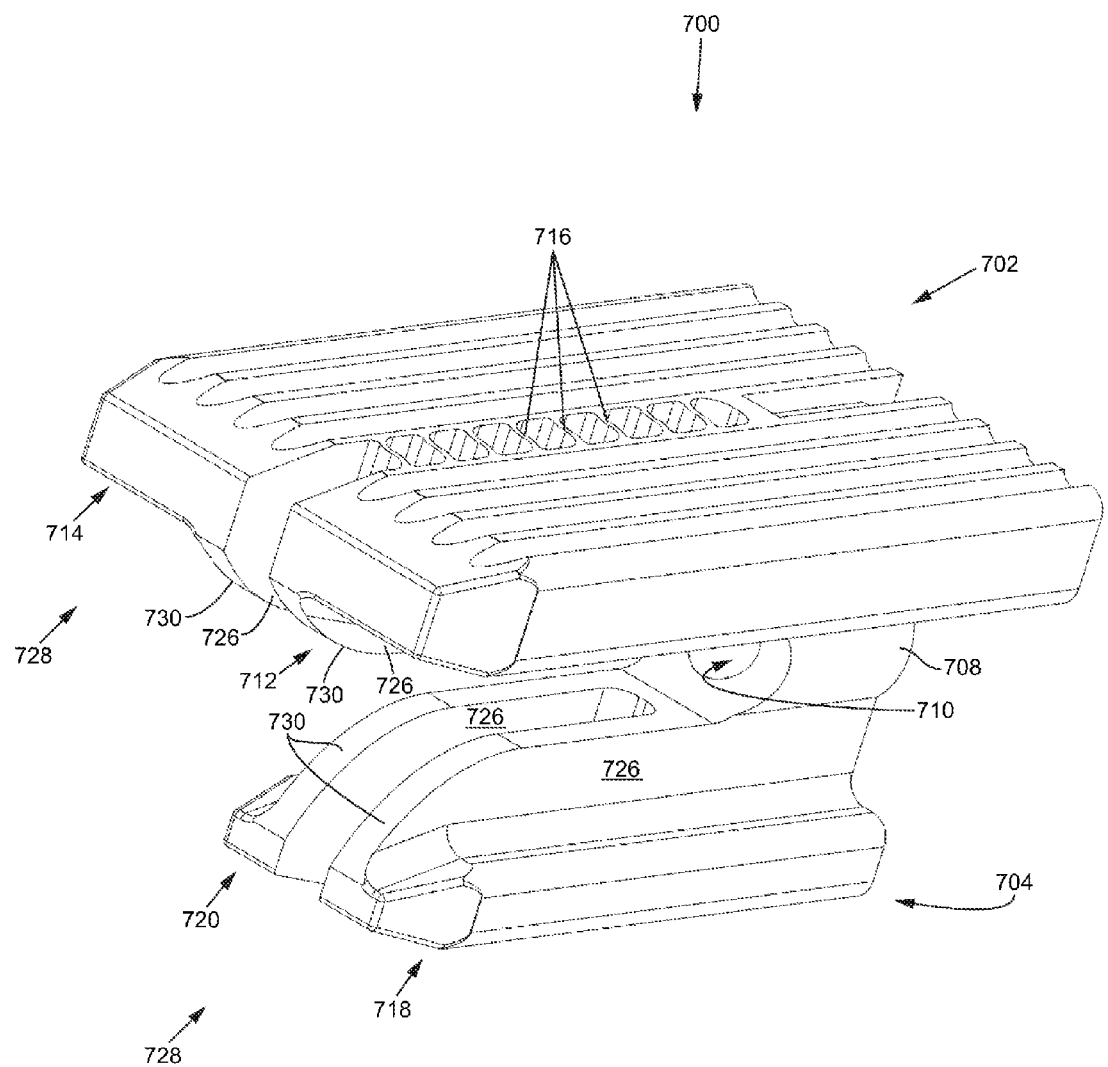
FIG. 19B is an isometric front and top view of the implant shown in FIG. 19A.

Still referring to FIGS. 19A-19B, the top planar keel member 702 extends distally further than the bottom planar keel member 704. A graft or anchor window 724 is formed distal of the tubular member 708 and in between inner surfaces of the top and bottom planar keel members 702, 704. Projecting inward from the inner surfaces of the top and bottom planar keel members 702, 704 are generally perpendicular flanges 726 the run the length of the members 702, 704. At a distal end 728 of the keel members 702, 704, the flanges 726 include a rounded taper 730.

Figure 19C:
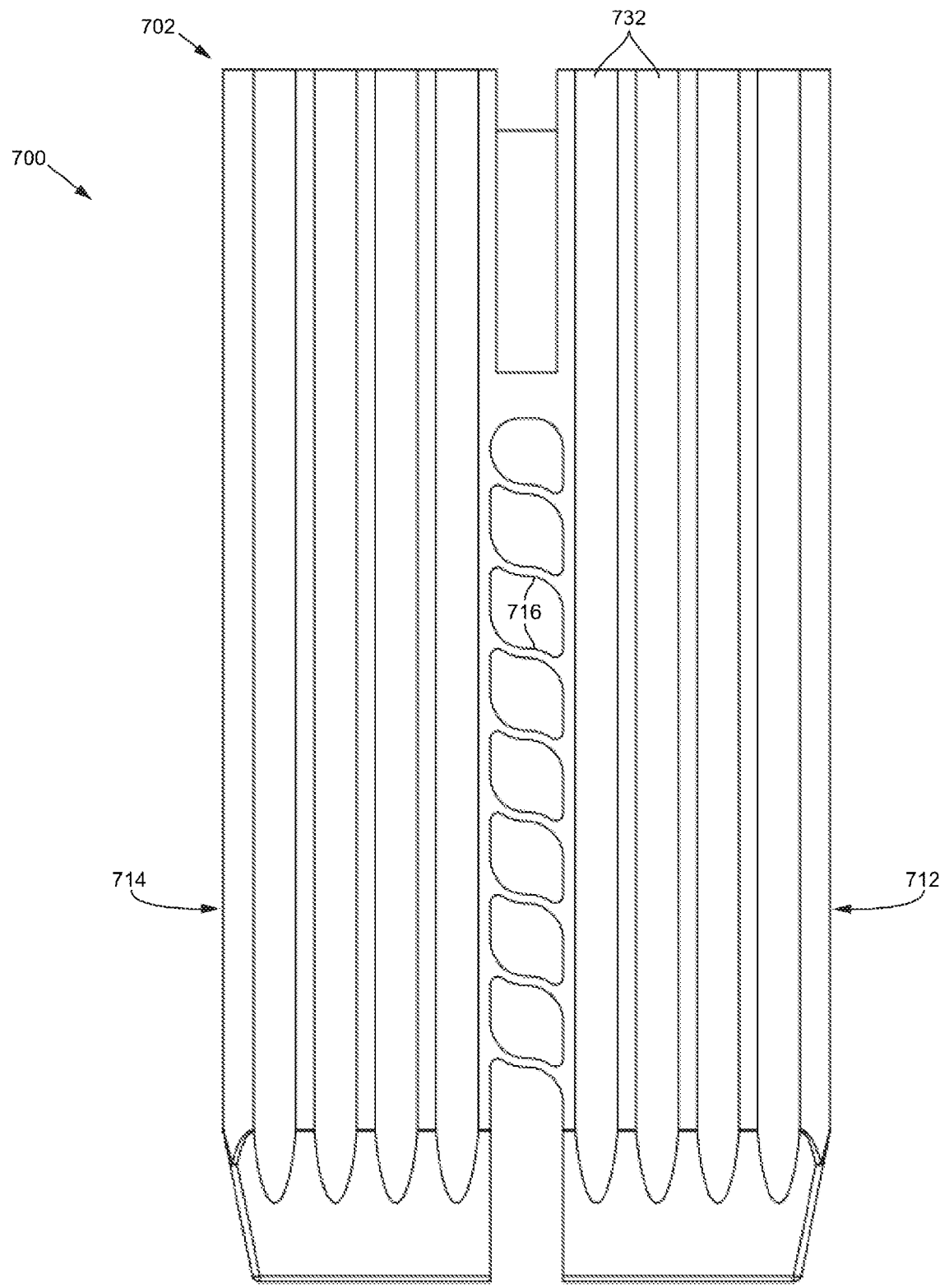
FIG. 19C is a top view of the implant shown in FIG. 19A.
Figure 19D:
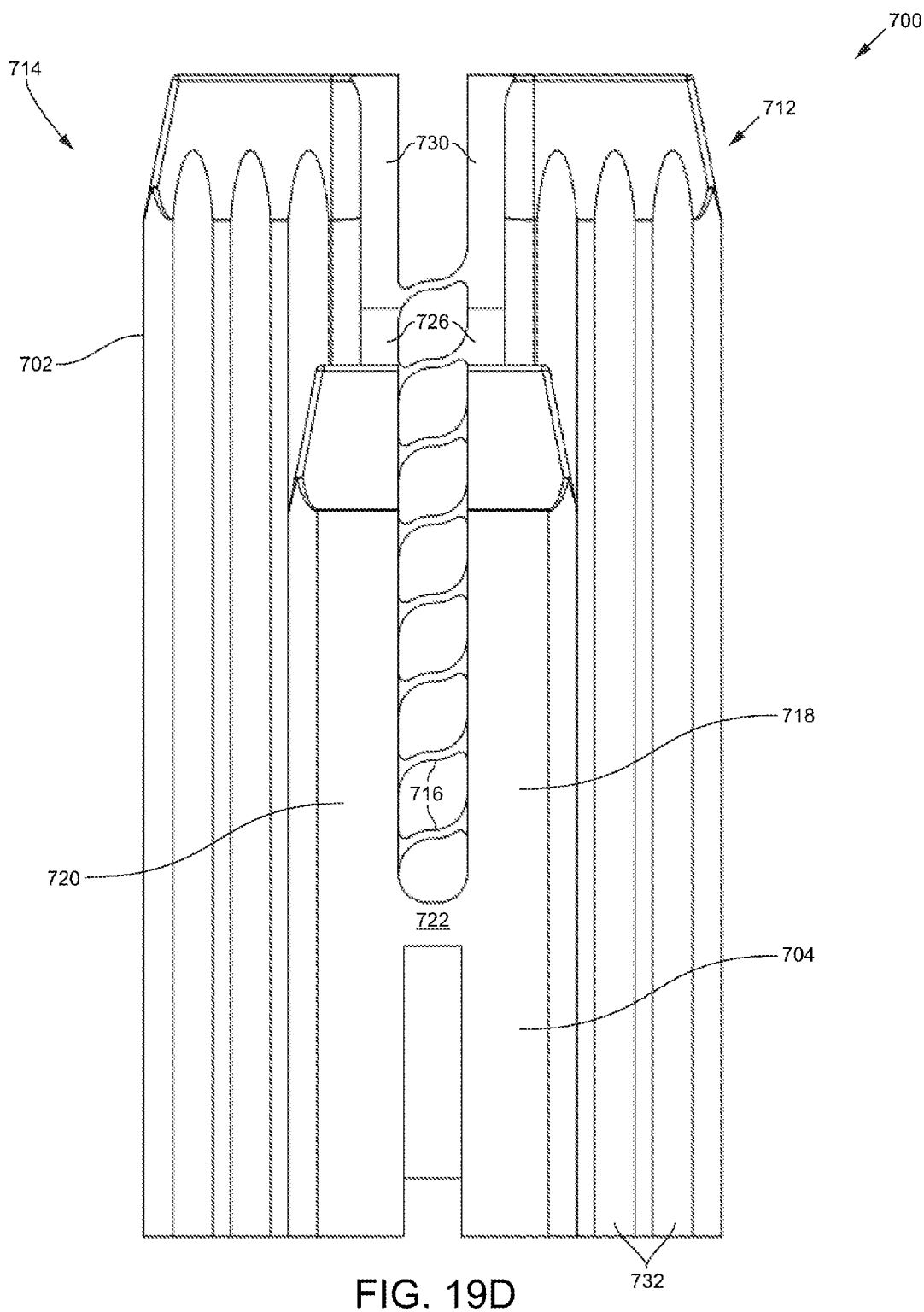
FIG. 19D is a bottom view of the implant shown in FIG. 19A.
Figure 19E:
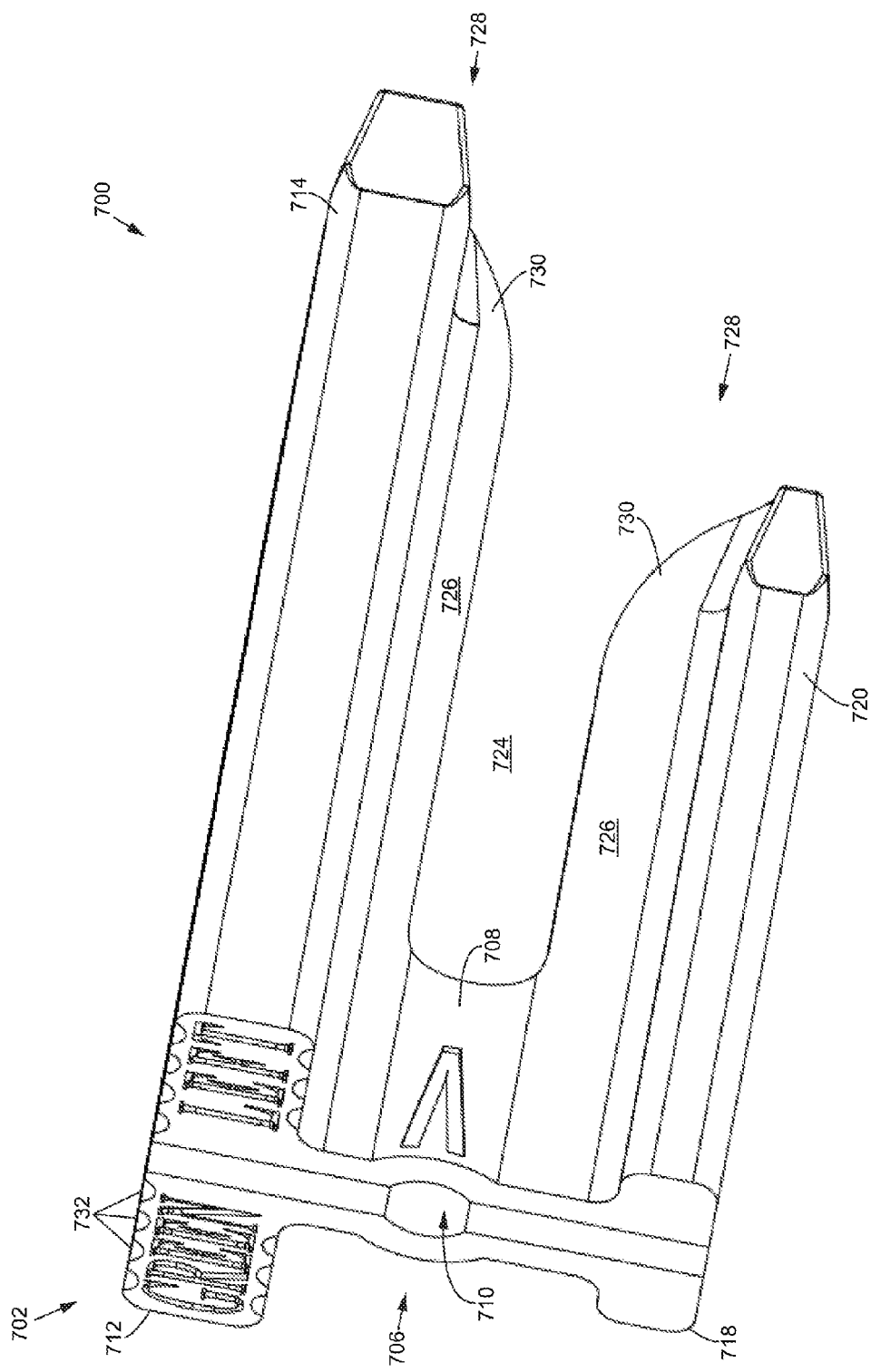
FIG. 19E is an isometric side and back view of the implant shown in FIG. 19A.
Figure 19F:
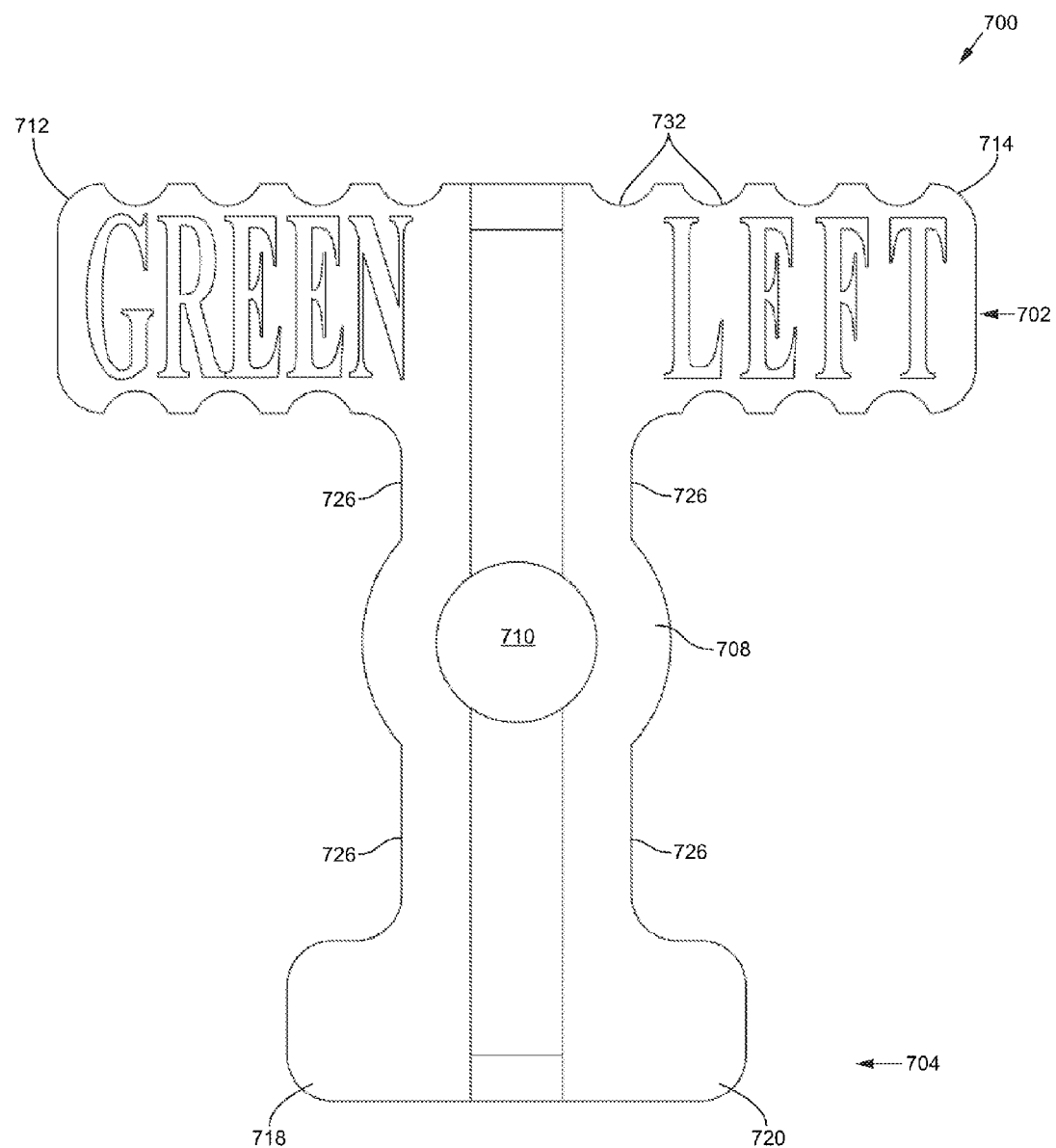
FIG. 19F is a back view of the implant shown in FIG. 19A.

As illustrated in FIGS. 19C-19D, which are respective top and bottom views of the implant 700, the implant 700 is symmetric about the sacrum sections 712, 718 and ilium sections 714, 720. And, when delivered into the sacroiliac joint such that the sacrum sections 712, 718 are positioned within the sacrum and the ilium sections 714, 720 are positioned within the ilium, the deformable structural elements 716, 722 lie in the plane of the joint. In this way, inward pressure from the sacrum or ilium can cause deformation of the deformable structural elements 716, 722 and, thus, provide some "give" to the implant 504 without driving apart the sacrum or ilium. As seen in these figures, the top and bottom planar keel members 702, 704 include longitudinally extending cylindrical grooves 732 extending the length of the implant 700. FIG. 19E depicts a back isometric view of the implant 700 illustrating the features previously described. And, FIG. 19F depicts a back view of the implant 700 further illustrating the features described herein.

The foregoing merely illustrates the principles of the embodiments described herein. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the embodiments described herein and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A method of fusing a sacroiliac joint, the method comprising:
   a) providing a joint implant comprising:
      i) a body extending between an implant proximal end and an implant distal end; and
      ii) a graft window extending non-parallel through the body and extending proximally from the implant distal end to define at least a portion of an opened distal end;
   b) providing a delivery tool comprising:
      i) an implant arm extending between a proximal implant arm end and a distal implant arm end, the distal implant arm end releasably coupled to the implant proximal end of the joint implant;
      ii) an anchor am extending between a proximal anchor arm end and a distal anchor arm end, the distal anchor arm end releasably coupled to a proximal end of an anchor element; and
      iii) a positioning arm coupling the implant arm and the anchor arm such that when coupled a delivery arrangement automatically exists such that the anchor element and the joint implant align in a trajectory such that the anchor element will be received within the graft window upon convergence of the anchor element and the joint implant, the implant arm being configured to rotate relative to the positioning arm about a longitudinal axis of the implant arm within a fixed range of rotation;
   c) delivering the anchor element transversely through the sacroiliac joint; and
   d) subsequent to step c), delivering the joint implant non-transversely into the sacroiliac joint such that the anchor element is positioned within the graft window of the joint implant, the joint implant in an orientation within the sacroiliac joint such that the body and the graft window are a generally within a plane defined by the sacroiliac joint.

2. The method of claim 1, wherein prior to step d) rotating the implant arm about the longitudinal axis and within the fixed range of rotation to select a final implant trajectory that will result in delivery of the joint implant into the sacroiliac joint in the orientation.

3. The method of claim 1, wherein the fixed range of rotation is about 60 degrees of rotation.

4. The method of claim 1, wherein the fixed range of rotation is between about 25 degrees and about 70 degrees.

5. The method of claim 1, wherein the body of the joint implant further comprises a first keel, a second keel opposite the first keel, and a spanning member coupling and extending between the first and second keels at the implant proximal end, wherein the graft window is defined between the first and second keels and the spanning member.

6. The method of claim 5, wherein the body of the joint implant further comprises a pair of wing members coupled with the spanning member and extending generally perpendicularly from a surface of the spanning member that extends between the first and second keels.

7. The method of claim 6, wherein the surface of the spanning member is a planar surface.

8. The method of claim 1, further comprising uncoupling the distal implant arm end from the implant proximal end by rotationally engaging a proximal portion of an implant retainer, the implant retainer extending through a passageway that extends through the implant arm and defining the distal implant arm end that releasably couples with the implant proximal end.

9. The method of claim 1, further comprising uncoupling the distal anchor arm end from the proximal end of the anchor element by rotationally engaging a proximal portion of an anchor retainer, the anchor retainer extending through a passageway that extends through the anchor arm and defining the distal anchor arm end that releasably couples with the proximal end of the anchor element.

10. The method of claim 1, wherein the implant arm includes a cam mechanism and the positioning arm includes a channel, wherein the cam mechanism includes a cam-shape that is configured to only partially rotate within the channel to define the fixed range of rotation.

11. The method of claim 1, wherein in step d) a distal-most depth of delivery of the joint implant is fixed so as to inhibit contact between a surface of the joint implant and the anchor element.

12. The method of claim 11, wherein a proximal portion of the implant arm includes a stop feature that is configured to contact the positioning arm when the distal-most depth is reached.

13. A method of fusing a sacroiliac joint, the method comprising:
  a) delivering an anchor element transversely through the sacroiliac joint; and
  b) subsequent to step a), delivering a joint implant non-transversely into the sacroiliac joint such that the anchor element and the joint implant are positioned in a pre-determined relationship relative to each other, wherein the pre-determined relationship is provided by a delivery tool comprising:
    i) an implant arm including a proximal implant arm end and a distal implant arm end, the distal implant arm end releasably coupled to the joint implant;
    ii) an anchor arm including a proximal anchor arm end and a distal anchor arm end, the distal anchor arm end releasably coupled to the anchor element; and
    iii) a positioning arm coupling the implant arm and the anchor arm such that when coupled a delivery arrangement automatically exists such that the anchor element and the joint implant align in a trajectory such that the anchor element and the joint implant will not contact each other during delivery of the joint implant non-transversely into the sacroiliac joint, the implant arm being configured to displace relative to the positioning arm within a fixed range of displacement, the displacement comprising at least one of rotation or translation.

14. The method of claim 13, wherein the joint implant comprises: a body extending between an implant proximal end and an implant distal end; and a graft window extending non-parallel through the body and extending proximally from the implant distal end to define at least a portion of an opened distal end.

15. The method of claim 14, wherein upon delivery of the joint implant non-transversely into the sacroiliac joint, the anchor element is positioned within the graft window of the joint implant, the joint implant being in an orientation within the sacroiliac joint such that the body and the graft window are a generally within a plane defined by the sacroiliac joint.

16. The method of claim 14, wherein the trajectory is such that the anchor element will be received within the graft window upon convergence of the anchor element and the joint implant, the implant arm being configured to rotate relative to the positioning arm about a longitudinal axis of the implant arm within a fixed range of rotation.

17. The method of claim 14, wherein upon delivery of the joint implant non-transversely into the sacroiliac joint, the anchor element is positioned outside the graft window of the joint implant, the joint implant being in an orientation within the sacroiliac joint such that the body and the graft window are a generally within a plane defined by the sacroiliac joint.

18. The method of claim 14, wherein the body of the joint implant further comprises a first keel, a second keel opposite the first keel, and a spanning member coupling and extending between the first and second keels at the implant proximal end, wherein the graft window is defined between the first and second keels and the spanning member.

19. The method of claim 18, wherein the body of the joint implant further comprises a pair of wing members coupled with the spanning member and extending generally perpendicularly from a surface of the spanning member that extends between the first and second keels.

20. The method of claim 13, wherein upon delivery of the joint implant non-transversely into the sacroiliac joint, the anchor element is positioned adjacent the joint implant, the joint implant being in an orientation within the sacroiliac joint such that a body of the joint implant is generally within a plane defined by the sacroiliac joint.

21. The method of claim 20, wherein the joint implant comprises: the body extending between an implant proximal end and an implant distal end; and a graft window extending non-parallel through the body and extending proximally from the implant distal end to define at least a portion of an opened distal end.

22. The method of claim 13, wherein upon delivery of the joint implant non-transversely into the sacroiliac joint, the anchor element is positioned adjacent the joint implant.

23. The method of claim 22, wherein the joint implant comprises: a body extending between an implant proximal end and an implant distal end; and a graft window extending non-parallel through the body.

24. The method of claim 23, wherein the body of the joint implant further comprises a first keel, a second keel opposite the first keel, and a spanning member coupling and extending between the first and second keels at the implant proximal end, wherein the graft window is defined between the first and second keels and the spanning member.

25. The method of claim 22, wherein the joint implant comprises: a body extending between an implant proximal end and an implant distal end; and a first keel extending along the body between the implant proximal end and the implant distal end.

* * * * *

UNITED STATES PATENT AND TRADEMARK OFFICE
CERTIFICATE OF CORRECTION

PATENT NO. : 9,717,539 B2  
APPLICATION NO. : 14/567956  
DATED : August 1, 2017  
INVENTOR(S) : Donner et al.

Page 1 of 1

It is certified that error appears in the above-identified patent and that said Letters Patent is hereby corrected as shown below:

In the Claims

In Claim 1, Column 38, Line 14, replace "am" with --arm--.

Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*